(12) United States Patent
McLeod et al.

(10) Patent No.: US 6,699,654 B1
(45) Date of Patent: Mar. 2, 2004

(54) ANTIMICROBIAL AGENTS DIAGNOSTIC REAGENTS, AND VACCINES BASED ON UNIQUE APICOMPLEXAN PARASITE COMPONENTS

(76) Inventors: Rima L. W. McLeod, 5729 Kimbark, Chicago, IL (US) 60637; Craig W. Roberts, 17 Kirklee Circus, Kirklee, Glasgow, G12 OTW Scotland (GB); Fiona Roberts, 17 Kirklee Circus, Kirklee, Glasgow, G12 OTW Scotland (GB); Jennifer J. Johnson, 13 Penny Ct., Bolingbrook, IL (US) 60440; Laurens Mets, 814 Sheridan Rd., Wilmette, IL (US) 60091

( * ) Notice: Subject to any disclaimer, the term of this patent is extended or adjusted under 35 U.S.C. 154(b) by 0 days.

(21) Appl. No.: 09/103,331

(22) Filed: Jun. 23, 1998

(51) Int. Cl.$^7$ .............................. C12Q 1/68; G01N 33/53
(52) U.S. Cl. ................................ 435/4; 435/6; 435/7.1
(58) Field of Search ................................... 435/4, 6, 7.1

*Primary Examiner*—Sean McGarry
(74) *Attorney, Agent, or Firm*—Alice O. Martin; Barnes & Thornburg

(57) ABSTRACT

This invention relates uses of components of plant-like metabolic pathways not including psbA or PPi phosphofructokinase and not generally operative in animals or encoded by the plastid DNA, to develop compositions that interfere with Apicomplexan growth and survival. Components of the pathways include enzymes, transit peptides and nucleotide sequences encoding the enzymes and peptides, or promoters of these nucleotide sequences to which antibodies, antisense molecules and other inhibitors are directed. Diagnostic and therapeutic reagents and vaccines are developed based on the components and their inhibitors.

9 Claims, 16 Drawing Sheets

Fig. 9(1)

```
                                                        CT  CAT CTT CTC GGT TTC   17
ACT TTT CTT TGA GTG CCT GTG TGA GAG ACG GTC GTC GCA ACA AGA ATC   65
TCC TCC GCT CAC GCC TTT CCT CAC AGT CCT GTT TTT CCT CCA GCT GTC  113
ACA CAT CCC GCT CGT TCC GCT GCA TCT CCT CAC ATT TCT TGC AGT CAG  161
ATG TCT TCC TAT GGA GCC GCT CTG CGC ATA CAC ACT TTC GGT GAA TCT  209
 M   S   S   Y   G   A   A   L   R   I   H   T   F   G   E   S   16
CAC GGC TCA GCC GTT GGG TGT ATA ATC GAC GGG CTG CCT CCT CGC CTC  257
 H   G   S   A   V   G   C   I   I   D   G   L   P   P   R   L   32
CCT CTT TCT GTC GAA GAT GTT CAG CCT CAA TTA AAT CGC AGA AGA CCC  305
 P   L   S   V   E   D   V   Q   P   Q   L   N   R   R   R   P   48
GGC CAA GGG CCT CTC TCG ACG CAG CGG AGA GAG AAA GAT CGA GTC AAC  353
 G   Q   G   P   L   S   T   Q   R   R   E   K   D   R   V   N   64
ATA CTC TCC GGT GTT GAA GAC GGA TAT ACA CTC GGT ACT CCC CTG GCG  401
 I   L   S   G   V   E   D   G   Y   T   L   G   T   P   L   A   80
ATG CTC GTC TGG AAT GAA GAC CGG CGG CCC CAG GAC TAC CAC GCC CTC  449
 M   L   V   W   N   E   D   R   R   P   Q   D   Y   H   A   L   96
GCG ACA GTC CCG CGT CCA GGT CAC GGG GAT TTC ACC TAC CAT GCA AAG  497
 A   T   V   P   R   P   G   H   G   D   F   T   Y   H   A   K  112
TAC CAC ATT CAC GCG AAA AGC GGG GGC GGT CGG AGC AGC GCG CGG GAG  545
 Y   H   I   H   A   K   S   G   G   G   R   S   S   A   R   E  128
ACT TTG GCG CGC GTC GCC GCT GGA GCA GTC GTT GAG AAG TGG CTA GGC  593
 T   L   A   R   V   A   A   G   A   V   V   E   K   W   L   G  144
ATG CAC TAC GGC ACC AGC TTC ACA GCT TGG GTC TGT CAG GTT GGT GAT  641
 M   H   Y   G   T   S   F   T   A   W   V   C   Q   V   G   D  160
GTC TCT GTG CCC CGA TCG CTC CGA AGA AAG TGG GAG CGG CAG CCG CCA  689
 V   S   V   P   R   S   L   R   R   K   W   E   R   Q   P   P  176
ACT CGC CAA GAC GTC GAT CGC CTT GGC GTG GTC CGC GTG AGC CCA GAT  737
 T   R   Q   D   V   D   R   L   G   V   V   R   V   S   P   D  192
GGA ACC ACA TTT CTC GAC GCG AAC AAC CGC CTT TAC GAC GAG CGA GGA  785
 G   T   T   F   L   D   A   N   N   R   L   Y   D   E   R   G  208
GAG GAA CTC GTC GAG GAG GAA GAC AAA GCC AGG CGT CGG CTT CTT TTC  833
 E   E   L   V   E   E   E   D   K   A   R   R   R   L   L   F  224
GGA GTC GAC AAC CCG ACG CCA GGA GAA ACA GTG ATT GAG ACC AGG TGC  881
 G   V   D   N   P   T   P   G   E   T   V   I   E   T   R   C  240
CCG TGC CCC TCC ACA GCT GTT CGC ATG GCT GTG AAA ATC AAC CAG ACC  929
 P   C   P   S   T   A   V   R   M   A   V   K   I   N   Q   T  256
CGA TCT CTG GGC GAT TCG ATT GGC GGA TGC ATC TCC GGT GCA ATC GTG  977
 R   S   L   G   D   S   I   G   G   C   I   S   G   A   I   V  272
CGG CCA CCG CTG GGC CTC GGC GAG CCG TGT TTC GAC AAA GTG GAG GCG 1025
 R   P   P   L   G   L   G   E   P   C   F   D   K   V   E   A  288
GAG CTG GCG AAG GCG ATG ATG TCG CTC CCT GCT ACG AAA GGG TTT GAG 1073
 E   L   A   K   A   M   M   S   L   P   A   T   K   G   F   E  304
ATT GGC CAG GGC TTT GCG AGT GTC ACG TTG CGA GGC AGC GAG CAC AAC 1121
 I   G   Q   G   F   A   S   V   T   L   R   G   S   E   H   N  320
GAC CGC TTC ATT CCC TTC GAG AGA GCG TCG TGT TCA TTC TCG GAA TCA 1169
 D   R   F   I   P   F   E   R   A   S   C   S   F   S   E   S  336
GCC GCG AGC ACG ATC AAG CAT GAA AGA GAT GGG TGT TCA GCT GCT ACA 1217
```

| | | | | | | | | | | | | | | |
|---|---|---|---|---|---|---|---|---|---|---|---|---|---|---|
| A | A | S | T | I | K | H | E | R | D | G | C | S | A | A | T | 352
| CTC | TCA | CGG | GAG | CGA | GGG | AGT | GAC | GGT | AGA | ACA | ACT | TCT | CGA | CAT | GAA | 1265
| L | S | R | E | R | A | S | D | G | R | T | T | S | R | H | E | 368
| GAG | GAG | GTG | GAA | AGG | GGG | CGG | GAG | CGC | ATA | CAG | CGC | GAT | ACC | CTC | CAT | 1313
| E | E | V | E | R | G | R | E | R | I | Q | R | D | T | L | H | 384
| GTT | ACT | GGT | GTA | GAT | CAG | CAA | AAC | GGC | AAC | TCC | GAA | GAT | TCA | GTT | CGA | 1361
| V | T | G | V | D | Q | Q | N | G | N | S | E | D | S | V | R | 396
| TAC | ACT | TCC | AAA | TCA | GAG | GCG | TCC | ATC | ACA | AGG | CTG | TCG | GGA | AAT | GCT | 1409
| Y | T | S | K | S | E | A | S | I | T | R | L | S | G | N | A | 416
| GCC | TCT | GGA | GGT | GCT | CCA | GTC | TGC | CGC | ATT | CCA | CTA | GGC | GAG | GGA | GTA | 1457
| A | S | G | G | A | P | V | C | R | I | P | L | G | E | G | V | 432
| CGG | ATC | AGG | TGT | GGA | AGC | AAC | AAC | GCT | GGT | GGA | ACG | CTC | GCA | GGC | ATT | 1505
| R | I | R | C | G | S | N | N | A | G | G | T | L | A | G | I | 448

ACA TCA GGA GAG AAC ATT TTT TTT CGG GTG GCC TTC AAG CCT GTT TCT  1553

| T | S | G | E | N | I | F | F | R | V | A | F | K | P | V | S | 464
|---|---|---|---|---|---|---|---|---|---|---|---|---|---|---|---|---|
| TCC | ATC | GGC | TTG | GAA | CAA | GAA | ACT | GCA | GAC | TTT | GCT | GGT | GAA | ATG | AAC | 1601
| S | I | G | L | E | Q | E | T | A | D | F | A | G | E | M | N | 480
| CAG | CTA | GCT | GTG | AAA | GGC | CGC | CAC | GAT | CCC | TGC | GTC | CTT | CCG | CGA | GCC | 1649
| Q | L | A | V | K | G | R | H | D | P | C | V | L | P | R | A | 496
| CCT | CCT | CTG | GTT | GAG | AGC | ATG | GCT | GCC | CTT | GTG | ATT | GGC | GAT | CTG | TGC | 1697
| P | P | L | V | E | S | M | A | A | L | V | I | G | D | L | C | 512
| CTC | CGC | CAG | CGC | GCC | CGG | GAA | GGG | CCG | CAC | CCC | CTT | CTC | GTC | CTT | CCT | 1745
| L | R | Q | R | A | R | E | G | P | H | P | L | L | V | L | P | 528
| CAA | CAC | AGT | GGT | TGC | CCA | TCT | TGC | TGA | GCT | CTA | CCT | TGT | TCC | AAA | AAC | 1793
| Q | H | S | G | C | P | S | C | * | | | | | | | | 536

TTG TGC ATA CGG GGT ACA CCA GGT TCC TCA CAA GGA GAA TCG TGA GGC  1841

GGT GAC TGG CCA GCG CCA CAG ATT GCT GTT CAT GCA CAA GAA AGA AAA  1889

CAG CGC ATT TCC GCC ACA ACC CAG CTG CAT GAA GTT GCT GGA TAT CGT  1937

TCC GGC GGT GCT CGG CCT TCT TCT CTA CGC TCG CGA TGA TAC GTC GCG  1985

AGC TTC ATC AAG CTC CTT TTG CAT TGT TAG TGG CTC CCA ACA GAA CCC  2033

TTT GTG GAA GGG AAT CTG GTC TCA CGC TTG CAG GAG AGA GTT CGC CTT  2081

TGT TCA CGA AAT AAC GAA GCC AAG CAG CTC AGT TGC ATT CAG CCT GCA  2129

CAC AGT TGC ATT CAG CCT GCA CAC TAA ACA CGG GCG AAA TCG TCG CGT  2177

GAT ATG TAG TTC TTC GGT TGT CAC GGT GAT TGT CGT CGT GTT TGA ACA  2225

ACT AAA CGT TTC TAA TGC TGG ATC TTA AAA AAA AAA AAA AAA AAA AAA  2273

AAA AAA AAA AAA AAA AAA AAA AAA AAA AAA AAA AAA AAA  2312

```
T.gondii        ------------------------------------------------MSSYGAALRIH  11
Synechocystis   ------------------------------------------------MGNTFGSLFRIT 12
S.lycopersicum  MASSMLTKQFLGAPFSSFGSGQQPSKLCSSNLRFPTHRSQPKRLEIQAAGNTFGNYFRVT 60
N.crassa        ------------------------------------------------MSTFGHYFRVT 11
H.influenza     ----------------------------------------------MAGNTIGQLFRVT 13
S.cerevisae     ------------------------------------------------MSTFGKLFRVT 11

T.gondii        TFGESHGSAVGCIIDGLPPRLPLSVEDVQPQLNRRRPGQGPLSTQRREKDRVNILSGVED  71
Synechocystis   TFGESHGGGVGVIIDGCPPRLEISPEEIQVDLDRRRPGQSKITTPRKEADQCEILSGVFE  72
S.lycopersicum  TFGESHGGGVGCIIDGCPPRLPLSESDMQVELDRRRPGQSRITTPRKETDTCKISSGTAD 120
N.crassa        TYGESHCKSVGCIVDGVPPGMELTEDDIQPQMTRRRPGQSAITTPRDEKDRVIIQSGTEF  71
H.influenza     TFGESHGIALGCIVDGVPPNLELSEKDIQPDLDRRKPGTSRYTTPRREDDEVQILSGVFE  73
S.cerevisae     TYGESHCKSVGCIVDGVPPGMSLTEADIQPQLTRRRPGQSKLSTPRDEKDRVEIQSGTEF  71

T.gondii        GYTLGTPLAMLVWNEDRRPQDYH--ALATVPRPGHGDFTYHAKYHIHAKSGGGRSSARET 129
Synechocystis   GKTLGTPIAILVRNKDARSQDYN--EMAVKYRPSHADATYEAKYGIRNWQGGGRSSARET 130
S.lycopersicum  GLTTGSPIKVEVPNTDQRGNDYS--EMSLAYRPSHADATYDFKYGVRSVQGGGRSSARET 178
N.crassa        GVTLGTPIGMLVMNEDQPPKDYGNKTMDIYPRPSHADWTYLEKYGVKASSGGGRSSARET 131
H.influenza     GKTTGTSIGMIIKNGDQRSQDYG--DIKDRFRFGHADFTYQQKYGIRDYRGGGRSSARET 131
S.cerevisae     GKTLGTPIAMMIKNEDQRPHDYS--DMDKFPRPSHADFTYSEKYGIKASSGGGRASARET 129

T.gondii        LARVAAGAVVEKWLGMHYGTSFTAWVCQVGDVSVPRSLRRKWEROQPPTRQDVDRLGVVRV 189
Synechocystis   IGRVAAGAIAKKILAQFNGVEIVAYVKSIQDIEA-------------------------- 164
S.lycopersicum  IGRVAAGAVAKKILKLYSGTEILAYVSQVHNVVLP------------------------- 213
N.crassa        IGRVAAGAIAEKYLKPRYGVEIVAFVSSVGSEHLFPPTAEHPSPST-------------- 177
H.influenza     AMRVAAGAIAKKYLREHFGIEVRGFLSQIGNIKIAP------------------------ 167
S.cerevisae     IGRVASGAIAEKFLAQNSNVEIVAFVTQIGEIKMNR------------------------ 165

T.gondii        SPDGTTFLDANNRLYDERGEELVEEEDKARRRLLFGVDNPTPGETVIETRCPCPSTAVRM 249
Synechocystis   -------TVDSNTVTLEQVESN---------------------IVRCPDEECAEKM    192
S.lycopersicum  -----EDLVDNQIVTLEQIESN---------------------IVRCPNPEYAEKM    243
N.crassa        ---NPEFLKLVNSITRETVDSFL---------------------PVRCPDAEANKRM   210
H.influenza     --------QKVGQIDWEKVNSN---------------------PFFCPDESAVEKF    194
S.cerevisae     DSFDPEFQHLLNTITREKVDSMG---------------------PIRCPDASVAGLM   201

T.gondii        AVKIHQTRSLGDSIGGCISGAIVRPPLGLGEPCFDKVEAELAKAMMSLPATKGFEIGQGF 309
Synechocystis   IERIDQVLRQKDSIGGVVECAIRNAPKGLGEPVFDKLEADLAKAMMSLPATKGFEFGSGF 252
S.lycopersicum  IGAIDYVRVRGDSVGGVVTCIVRNVPRGLGTPVFDKLEAELAKACMSLPATKGFEFGSGF 303
N.crassa        EDLITKFRDNHDSIGGTVTCVIRNVPSGLGEPAFDKLEAMLAHAMLSIPATKGFEVGSGF 270
H.influenza     DELIRELKKEGDSIGAKLTVIAENVPVGLGEPVFDRLDADLAHALMGINAVKGVEIGDGF 254
S.cerevisae     VKEIEKYRGNKDSIGGVVTCVVRNLPTGLGEPCFDKLEAMLAHAMLSIPASKGFEIGSGF 261
```

```
T.gondii        ASVTLRGSEHNDRFIPFERASCSFSESAASTIKHERDGCSAATLSRERASDGRTTSRHEE  369
Synechocystis   AGTLLTGSQHNDEYYLDEAGEWR-------------------------------------  275
S.lycopersicum  AGTFMTGSEHNDEFFMDEHDQIR-------------------------------------  326
N.crassa        GGCEVPGSIHNDPFVSAENTEIPPSVAASGAARNGI------------------------  306
H.influenza     AVVEQRGSEHRDEMTPNGFESNH-------------------------------------  277
S.cerevisae     QGVSVPGSKHNDPFYFEKETNR--------------------------------------  283

T.gondii        EVERGRERIQRDTLHVTGVDQQNGNSEDSVRYTSKSEASITRLSGNAASGGAPVCRIPLG  429
Synechocystis   ------------------------------------------------------------
S.lycopersicum  ------------------------------------------------------------
N.crassa        ------------------------------------------------------------
H.influenza     ------------------------------------------------------------
S.cerevisae     ------------------------------------------------------------

T.gondii        EGVRIRCGSNNAGGTLAGITSGENIFFRVAFKPVSSIGLEQETADFA-GEMNQLAVKGRH  488
Synechocystis   ------TRTNRSGGVQGGISNGEPIIMRIAFKPTATIGQEQKTVSNI-GEETTLAAKGRH  328
S.lycopersicum  ------TKTNRSGGIQGGISNGEIINMRVAFKPTSTIARKQHTVSRD-KHETELIARGRH  379
N.crassa        PRPKLTTKTNFSGGIQGGISNGAPIYFRVGFKPAATIGQEQTTATYDGTSEGVLAAKGRH  366
H.influenza     ----------AGGILGGISSGQPIIATIALKPTSSITIPGRSINLN-GEAVEVVTKGRH  325
S.cerevisae     ----LRTKTNNSGGVQGGISNGENIYFSVPFKSVATISQEQKTATYD-GEEGILAAKGRH  338

T.gondii        DPCVLPRAPPLVESMAALVIGDLCLRQRAREGPHPLLVLPQHSGCPSC-----------  536
Synechocystis   DPCVLPRAVPMVEAMAALVLCDHLLRFQAQCKTL-------------------------  362
S.lycopersicum  DPCVVPRAVPMVEAMVALVLVDQLMTQYAQCMLFPVNLTLQEPLQPSTTKSA--------  431
N.crassa        DPSVVPRAVPIVEAMAALVIMDAVLAHEARVTAKSLLPPLKQTINSGKDTVGNGVSENVQ  426
H.influenza     DPCVGIRAVPIAEAMVAIVLLDHLLRFKAQCK---------------------------  357
S.cerevisae     DPAVTPRAIPIVEAMTALVLADALLIQKARDFSRSVVH---------------------  376

T.gondii        ------
Synechocystis   ------
S.lycopersicum  ------
N.crassa        ESDLAQ  432
H.influenza     ------
S.cerevisae     ------
```

Fig. 10(2)

Transit Peptide Wx Zea Mays    MAALATSQLVATRAGLGVPDASTFRRGAAQGLRGARASAAADTLSM-RTS-ARAAPRHQQQARRGRFPSLVVCASAGMNVVFV
(SEQ ID NO: 44)

Homologous Portion of T. gondii AroC    SCSFSESAASTIKHERDGCSAATLSRERASDGRFTSRHEEEVERG
(SEQ ID NO: 43)

Mature protein starts here

Processing site

Fig. 11

McLeod et al.

Fig. 12 (1)

```
                                                              CT CGA GTT      6
TTT TTT TTT TTT TTT TTT TTG ATA CAT AAT AAT CAA GAG TTC TTT ATA             56
CTA ACA GAC TTA TTT AAT GTA TTA TTT TTG GTA AAC AAA AAA AAC ATT            104
ATG AGC ACA TAT GGG ACT TTA TTA AAA GTA ACA TCC TAC GGA GAA AGT            152
 M   S   T   Y   G   T   L   L   K   V   T   S   Y   G   E   S             16
CAT GGG AAA GCT ATT GGG TGT GTG ATC GAT GGG TTT TTA TCC AAT ATA            200
 H   G   K   A   I   G   C   V   I   D   G   F   L   S   N   I             32
GAA ATA AAT TTT GAT TTA ATA CAA AAA CAA TTA GAT AGA CGA AGA CCA            248
 E   I   N   F   D   L   I   Q   K   Q   L   D   R   R   R   P             48
AAT CAA TCA AAA CTA ACT AGT AAT AGA AAC GAA AAA GAT AAA CTT GTT            296
 N   Q   S   K   L   T   S   N   R   N   E   K   D   K   L   V             64
ATA CTT TCA GGA TTT GAT GAA AAT AAA ACA TTA GGT ACA CCT ATT ACA            344
 I   L   S   G   F   D   E   N   K   T   L   G   T   P   I   T             80
TTT TTA ATA TAT AAT GAA GAT ATT AAA AAA GAA GAT TAT AAT TCT TTT            392
 F   L   I   Y   N   E   D   I   K   K   E   D   Y   N   S   F             96
ATA AAT ATT CCT AGA CCA GGA CAT GGA GAT TAT ACC TAT TTT ATG AAA            440
 I   N   I   P   R   P   G   H   G   D   Y   T   Y   F   M   K            112
TAT CAT GTT AAA AAT AAA AGT GGA AGT AGT AGA TTT TCT GGA AGA GAA            488
 Y   H   V   K   N   K   S   G   S   S   R   F   S   G   R   E            128
ACA GCC ACA AGA GTT GCT GCT GGG GCG TGC ATT GAA CAA TGG CTT TAT            536
 T   A   T   R   V   A   A   G   A   C   I   E   Q   W   L   Y            144
AAA TCT TAT AAT TGT TCT ATT GTT AGT TAT GTA CAT TCA GTT GGG AAT            584
 K   S   Y   N   C   S   I   V   S   Y   V   H   S   V   G   N            160
ATA AAG ATA CCT GAA CAA GTC AGC AAA GAA TTG GAA AAT AAA AAT CCA            632
 I   K   I   P   E   Q   V   S   K   E   L   E   N   K   N   P            176
CCC TCA AGA GAT TTA GTA GAT TCT TAT GGA ACC GTT AGA TAT AAT GAA            680
 P   S   R   D   L   V   D   S   Y   G   T   V   R   Y   N   E            192
AAA GAA AAA ATA TTT ATG GAT TGT TTT AAT AGA ATA TAT GAT ATG AAT            728
 K   E   K   I   F   M   D   C   F   N   R   I   Y   D   M   N            208
GCT TCT ATG TTA AAA ACT GAT GAA TAT AAT AAA AAC ACA TTG ACT ATT            776
 A   S   M   L   K   T   D   E   Y   N   K   N   T   L   T   I            224
CCT TCA ATA GAT AAC ACG TAT ATA AAT GTA AAA ACT AAT GAA TGT AAT            824
 P   S   I   D   N   T   Y   I   N   V   K   T   N   E   C   N            240
ATA AAT CAG GTT GAT AAT AAT CAT AAC AAT TAT ATT AAT GAT AAG GAT            872
 I   N   Q   V   D   N   N   H   N   N   Y   I   N   D   K   D            256
AAC ACT TTT AAT AAT TCT GAA AAA TCG GAT GAA TGG ATT TAT TTA CAA            920
 N   T   F   N   N   S   E   K   S   D   E   W   I   Y   L   Q            272
ACA AGA TGT CCA CAT CCA TAT ACT GCT GTA CAA ATT TGT TCT TAT ATT            968
 T   R   C   P   H   P   Y   T   A   V   Q   I   C   S   Y   I            288
TTG AAA CTA AAA AAT AAA GGA GAT AGT GTT GGG GGT ATT GCT ACA TGC           1016
 L   K   L   K   N   K   G   D   S   V   G   G   I   A   T   C            304
ATT ATA CAA AAT CCT CCT ATA GGT ATT GGA GAA CCT ATT TTT GAC AAA           1064
 I   I   Q   N   P   P   I   G   I   G   E   P   I   F   D   K            320
TTG GAA GCT GAG CTA GCC AAA ATG ATT TTA TCT ATT CCA CCC GTG AAA           1112
 L   E   A   E   L   A   K   M   I   L   S   I   P   P   V   K            336
```

```
GGA ATA GAA TTC GGG AGT GGA TTT AAT GGT ACA TAT ATG TTT GGC TCA   1160
 G   I   E   F   G   S   G   F   N   G   T   Y   M   F   G   S    352
ATG CAT AAT GAT ATC TTC ATA CCT GTA GAA AAT ATG TCT ACA AAA AAA   1208
 M   H   N   D   I   F   I   P   V   E   N   M   S   T   K   K    368
GAA AGT GAT TTA TTA TAT GAT GAT AAA GGT GAA TGT AAA AAT ATG TCT   1256
 E   S   D   L   L   Y   D   D   K   G   E   C   K   N   M   S    384
TAT CAT TCA ACG ATT CAA AAT AAT GAG GAT CAA ATA TTA AAT TCA ACT   1304
 Y   H   S   T   I   Q   N   N   E   D   Q   I   L   N   S   T    400
AAA GGA TTT ATG CCT CCT AAA AAT GAC AAG AAT TTT AAT AAT ATT GAT   1352
 K   G   F   M   P   P   K   N   D   K   N   F   N   N   I   D    416
GAT TAC AAT GTT ACG TTT AAT AAT AAT GAA GAA AAA TTA TTA ATT ACA   1400
 D   Y   N   V   T   F   N   N   N   E   E   K   L   L   I   T    432
AAA ACA AAT AAT TGT GGT GGG ATT TTA GCT GGC ATT TCA ACA GGA AAC   1448
 K   T   N   N   C   G   G   I   L   A   G   I   S   T   G   N    448
AAT ATT GTT TTT AGA TCA GCA ATC AAA CCT GTA TCA TCA ATA CAA ATA   1496
 N   I   V   F   R   S   A   I   K   P   V   S   S   I   Q   I    464
GAA AAA GAA ACA AGT GAT TTT TAT GGA AAT ATG TGT AAC TTG AAA GTT   1544
 E   K   E   T   S   D   F   Y   G   N   M   C   N   L   K   V    480
CAA GGG AGA CAT GAT AGC TGT ATT TTA CCA AGA TTA CCA CCC ATT ATT   1592
 Q   G   R   H   D   S   C   I   L   P   R   L   P   P   I   I    496
GAA GCA TCT TCT TCA ATG GTT ATA GGA GAT TTA ATA TTA CGA CAA ATA   1640
 E   A   S   S   S   M   V   I   G   D   L   I   L   R   Q   I    512
TCA AAG TAT GGA GAT AAA AAG TTG CCA ACA TTG TTT AGG AAT ATG TAA   1688
 S   K   Y   G   D   K   K   L   P   T   L   F   R   N   M   *    527
CAT AAT GAT TTT GTA ATC CTC AAT TAA AAT GAA AAA TTA TAA AAT ATA   1736

TAT TTT ATA TAT ATA TAT AAA ATA TAT ATA TAT ATA TAT AAA ATA TAA   1784

ATA TAT GTA TAA TAA TTC AAT TTG CGC AAT CGA TCA AAA TAC ATT TCG   1832

TCT AC                                                            1837
```

Fig. 12(2)

ANTIMICROBIAL AGENTS DIAGNOSTIC REAGENTS, AND VACCINES BASED ON UNIQUE APICOMPLEXAN PARASITE COMPONENTS

This application claims priority from PCT/US97/12497 filed Jul. 18, 1997 which claims priority from U.S. Ser. No. 08/773,302 filed Dec. 23, 1996.

The U.S. government may have rights in this patent by means of partial support under: NIH NIAID TMP R01 AI 16945; NIH NIAID TMP R01 AI 27530.

This invention relates uses of components of plant-like metabolic pathways not including psbA or PPi phosphofructokinase and not generally operative in animals or encoded by the plastid DNA, to develop compositions that interfere with Apicomplexan growth and survival. Components of the pathways include enzymes, transit peptides and nucleotide sequences encoding the enzymes and peptides, or promoters of these nucleotide sequences to which antibodies, antisense molecules and other inhibitors are directed. Diagnostic and therapeutic reagents and vaccines are developed based on the components and their inhibitors.

BACKGROUND

Apicomplexan parasites cause the serious diseases malaria, toxoplasmosis, cryptosporidiosis, and eimeriosis. Malaria kills more than 2 million children each year. Toxoplasmosis is the major opportunistic brain infection in AIDS patients, causes loss of life, sight, hearing, cognitive and motor function in congenitally infected infants, and considerable morbidity and mortality in patients immunocompromised by cancer, transplantation, autoimmune disease and their attendant therapies. Cryptosporidiosis is an untreatable cause of diarrhea in AIDS patients and a cause of epidemics of gastrointestinal disease in immunocompetent hosts. Eimeria infections of poultry lead to billions of dollars in losses to agricultural industries each year. Other Apicomplexan infections, such as babesiosis, also cause substantial morbidity and mortality. Although there are some methods for diagnosis and treatment of Apicomplexan caused diseases, some of these treatments are ineffective and often toxic to the subject being treated.

The tests available to diagnose Apicomplexan infections include assays which isolate the parasite, or utilize light, phase, or fluorescence microscopy, ELISAs, agglutination of parasites or parasite components to detect antibodies to parasites, or polymerase chain reaction (PCR) to detect a parasite gene. Most of the assays utilize whole organisms or extracts of whole organisms rather than recombinant proteins or purified parasite components. In many instances, the available assays have limited ability to differentiate whether an infection was acquired remotely or recently, and are limited in their capacity to diagnose infection at the outpatient or field setting.

The primary antimicrobial agents used to treat toxoplasmosis are pyrimethamine (a DHFR inhibitor) and sulfadiazine (a PABA antagonist). The use of pyrimethamine is limited by bone marrow toxicity which can be partially corrected by the concomitant administration of folinic acid. *T. gondii* cannot utilize folinic acid but mammalian cells can. Another problem is that pyrimethamine is potentially teratogenic in the first trimester of pregnancy. The use of sulfonamides is limited by allergy, gastrointestinal intolerance, kidney stone formation and Stevens-Johnson syndrome.

There are a small number of antimicrobial agents utilized less frequently to treat toxoplasmosis. These include clindamycin, spiramycin, azithromycin, clarithromycin and atovaquone. Usefulness of these medicines for treatment of toxoplasmosis is limited by toxicities including allergy and antibiotic-associated diarrhea, (especially *Clostridium difficile* toxin associated colitis with clindamycin use). Lesser or uncertain efficacy of macrolides such as spiramycin, azithromycin, and clarithromycin also limits use of these antimicrobial agents. Atovaquone treatment of toxoplasmosis may be associated with lack of efficacy and/or recrudescent disease. There are no medicines known to eradicate the latent, bradyzoite stage of *T. gondii*, which is very important in the pathogenesis of toxoplasmosis in immunocompromised individuals or those with recurrent eye disease.

Medicines used to treat malaria include quinine sulfate, pyrimethamine, sulfadoxine, tetracycline, clindamycin, chloroquine, mefloquine, halofantrine, quinidine gluconate, quinidine dihydrochloride, quinine, primaquine and proguanil. Emergence of resistance to these medicines and treatment failures due to resistant parasites pose major problems in the care of patients with malaria. Toxicities of mefloquine include nausea, vomiting, diarrhea, dizziness, disturbed sense of balance, toxic psychosis and seizures. Melfoquine is teratogenic in animals. With halofantrene treatment, there is consistent, dose-related lengthening of the PR and Qt intervals in the electrocardiogram. Halofantrene has caused first degree heart block. It cannot be used for patients with cardiac conduction defects. Quinidine gluconate or dihydrochloride also can be hazardous. Parenteral quinine may lead to severe hypoglycemia. Primaquine can cause hemolytic anemia, especially in patients whose red blood cells are deficient in glucose 6-phosphate dehydrogenase. Unfortunately, there are no medicines known to be effective in the treatment of cryptosporidiosis.

To more effectively treat Apicomplexan infections, there is an urgent need for discovery and development of new antimicrobial agents which are less toxic than those currently available, have novel modes of action to treat drug resistant parasites that have been selected by exposure to existing medicines, and which are effective against presently untreatable parasite life cycle stages (e.g., *Toxoplasma gondii* bradyzoites) and presently untreatable Apicomplexan parasites (e.g., *Cryptosporidium parvum*). Improved diagnostic reagents and vaccines to prevent these infections are also needed.

Information available on Apicomplexan parasites has not yet provided keys to solutions to health problems associated with the parasites. Analogies to other organisms could provide valuable insights into the operations of the parasite. There are reports of Apicomplexan parasites having plastids, as well as the nuclear encoded proteins, tubulin, calmodulin, PPi phosphofructokinase and enolase, which are reported to be similar in part to, or homologous with, counterparts in plant-like, lower life forms and higher plants. There are reports of a plastid genome and components of a protein synthetic system in a plastid-like organelle of Apicomplexans. Plasmodium and *T. gondii* plastid DNA sequences were reported to have homologies to algal plastid DNA sequences. The plastid membrane of *T. gondii* was reported to be composed of multiple membranes that appear morphologically similar to those of plant/algal chloroplasts, except for the presence of two additional membranes in the *T. gondii* plastid, suggesting that it may have been an ancient algal endosymbiont. Some of these Apicomplexan proteins such as tubulin, calmodulin and enolase with certain plant-like features also are found in animals, and therefore may appear in the host as well as the parasite. A homologue to a gene, psbA encoding a plant protein important for photosynthesis, also was said to be present in Apicomplexans.

Certain herbicides have been reported to inhibit the growth of Apicomplexans. The herbicides which affect growth of Apicomplexans are known to affect plant microtubules or a plant photosynthetic protein. In addition, a compound, salicylhydroxamic acid, (SHAM), had been found to inhibit *Plasmodium falciparum* (malaria) and *Babesia microti.*

Techniques of medicinal chemistry and rational drug design are developed sufficiently to optimize rational construction of medicines and their delivery to sites where Apicomplexan infections occur, but such strategies have not yet resulted in medicines effective against Apicomplexans. Rational development of antimicrobial agents has been based on modified or alternative substrate competition, product competition, change in enzyme secondary structure, and direct interference with enzyme transport, or active site. Antisense, ribozymes, catalytic antibodies, disruption of cellular processes using targeting sequences, and conjugation of cell molecules to toxic molecules are newly discovered strategies employed to interrupt cellular functions and can be utilized to rationally develop novel antimicrobial compounds, but they have not yet been utilized to design medicines effective against Apicomplexans. Large scale screening of available compounds with recombinant enzymes is used to identify potentially effective antimicrobial agents.

Reagents to diagnose Apicomplexan parasite infections have been developed targeting components of Apicomplexans or immune responses to the parasites, using ELISA, western blot, and PCR technologies, but improved diagnostic reagents, especially those that establish duration of infection or that can be used in outpatient settings are needed to diagnose Apicomplexan infections. No vaccines to prevent Apicomplexan infections are available for humans and only a live vaccine prepared for prevention of toxoplasmosis in sheep is available for livestock.

To summarize, Apicomplexan parasites cause substantial morbidity and mortality, and treatments against the parasites are suboptimal or non-existent. Improved antimicrobial compounds that attack Apicomplexan parasites are needed. Because the diseases Apicomplexan parasites cause in some instances are due to recrudescence of latent parasites, an especially pressing clinical problem is that there are no effective antimicrobial agents effective for treatment of these latent parasite life cycle stages, especially in sequestered sites such as the brain or eye. New approaches and drug targets are required. Better in vitro and in vivo assays for candidate compounds are also needed. Better diagnostic and therapeutic methods, reagents and vaccines to prevent these infections are needed.

SUMMARY OF THE INVENTION

This invention relates uses of components of plant-like metabolic pathways (not usually associated with animals, not encoded in the plastid genome, and not including psbA or PPi phosphofructokinase) to develop compositions that interfere with Apicomplexan growth and survival. Components of the pathways include enzymes, transit peptides and nucleotide sequences encoding the enzymes and peptides, or promoters of these nucleotide sequences, to which antibodies, antisense molecules and other inhibitors are directed. Diagnostic and therapeutic reagents and vaccines are developed based on the components and their inhibitors. Attenuation of live parasites through disruption of any of these components or the components themselves provide vaccines protective against Apicomplexans.

Transit peptides are used to identify other proteins and their organelle targeting sequences that enter and exit from unique Apicomplexan organelles. The identified components are potential for production of medicines, reagents and assays, and vaccines. The protein which includes the transit peptide is not necessarily an enzyme in a biochemical pathway.

The methods and compositions of the present invention arise from the inventors' discovery that metabolic pathways, and targeting signals similar to those found in plants and algae, especially, but not exclusively those encoded within the nucleus, are present in Apicomplexan parasites. These plant-like pathways in Apicomplexan parasites are targetable by inhibitors, as measured by determining whether the inhibitors, either singly or in combination, are effective in inhibiting or killing Apicomplexan parasites in vitro and/or in vivo.

The present invention includes new methods and compositions to treat, diagnose and prevent human and veterinary disease due to Apicomplexan infections. The invention is based on applications and manipulations of components of algal and higher plant-like metabolic pathways discovered in Apicomplexan parasites. "Plant-like" means that products of the pathways, enzymes and nucleotide sequences encoding enzymes in the pathways, are homologous or similar to products, enzymes and nucleotide sequences known in plants, wherein plants include algae. As used herein, "plant-like" excludes metabolic pathways generally operative in or identical to those in animals and pathways involving psbA or phosphofructokinase and those encoded by the plastid genome. The limits of a "pathway" are defined as they are generally known to those of skill in the art. Methods to detect plant counterparts in Apicomplexan include: a) immunoassays using antibodies directed to products and enzymes known in plants, b) hybridization assays using nucleotide probes that hybridize to specific sequences in plants; c) determining homologies of Apicomplexan nucleotide or protein sequences with plant nucleotide or protein sequences; and/or d) substrate tests for specific enzymatic activity.

The "plant-like" pathways of the present invention are identified by:

a) identification of metabolic pathways characteristic of plants but not generally present in animals;
b) identification and characterization of Apicomplexan enzymes, nucleic acids and transit sequences as components similar or homologous to those in a);
c) identification and development of compounds (inhibitors) which abrogate the effect of the components of the pathways in vitro and in vivo, singly or in a plurality, against one or more types of Apicomplexan parasites and in conjoint Apicomplexan, bacterial and fungal infections.

The identified pathways are then used for:

a) rational design or selection of compounds more active than the known compounds (inhibitors), with good absorption following oral administration, with appropriate tissue distribution and without toxicity or carcinogenicity;
b) testing of such rationally designed compounds alone and together for safety, efficacy and appropriate absorption and tissue distribution in vitro and in vivo;
c) development and testing of diagnostic reagents and assays;
d) development and testing of live attenuated and component based vaccines.

By locating new targets in Apicomplexan pathways, doors now are open for development of more effective antimicrobial agents to treat Apicomplexan parasites in humans and agricultural animals. In addition, enzymes in these plant-like pathways provide improved diagnostic tests for diseases caused by Apicomplexans. Vaccines against infectious diseases caused by Apicomplexan parasites are derived from the novel compositions of the invention.

A method for inhibiting an Apicomplexan parasite, includes selecting the metabolic pathway of the present invention and interfering with the operation of the pathway in the parasite. The Apicomplexan parasite is preferably selected from the group that includes Toxoplasma, Plasmodium, Cryptosporidia, Eimeria, Babesia and Theileria. The pathway may utilize a component encoded by an Apicomplexan nuclear gene.

Suitable metabolic pathways or components include a) synthesis of heme from glutamate and tRNA glu by the plant-like, heme synthesis (5 carbon) pathway (hereinafter the "heme synthesis pathway");

b) synthesis of C4 acids (succinate) by the breakdown of lipids into fatty acids and then acetyl CoA, and their use in the glyoxylate cycle (hereinafter the "glyoxylate cycle");

c) synthesis of chorismate from phosphoenolpyruvate and erythrose 4 phosphate by the shikimate pathway (hereinafter the "shikimate pathway");

d) synthesis of tetrahydrofolate from chorismate by the shikimate pathway;

e) synthesis of ubiquinone from chorismate by the shikimate pathway;

f) electron transport through the alternative pathway with use of the alternative oxidase (hereinafter the "alternative oxidase pathway");

g) transport of proteins into or out of organelles through the use of transit sequences;

h) synthesis of aromatic amino acids (phenylalanine, tyrosine and tryptophan) from chorismate by the shikimate pathway;

i) synthesis of the menaquinone, enterobactin and vitamin K1 from chorismate by the shikimate pathway;

j) synthesis of the branched chain amino acids (valine, leucine and isoleucine) from pyruvate and ketobutyrate by the plant-like branched chain amino acid synthesis pathway;

k) synthesis of the "essential" (i.e., not synthesized by animals) amino acids, histidine, threonine, lysine and methionine by the use of plant-like amino acid synthases;

l) synthesis of linoleneic and linoleic acid;

m) synthesis of amylose and amylopectin with starch synthases and Q (branching) enzymes and their degradation;

n) synthesis of auxin growth regulators from indoleacetic acid derived from chorismate;

o) synthesis of isoprenoids (diterpenes, 5 carbon units with some properties of lipids) such as giberellins and abscidic acid by the mevalonic acid to giberellin pathway.

The interfering compositions are selected from the group consisting of enzyme inhibitors including competitors; inhibitors and competitive or toxic analogues of substrates, transition state analogues, and products; antibodies to components of the pathways; toxin conjugated antibodies or components of the pathways; antisense molecules; and inhibitors of transit peptides in an enzyme. In particular, the interfering compositions include gabaculine, 3-NPA, SHAM, 8-OH-quinoline, NPMG. Interfering with the operation of the metabolic pathway is also accomplished by introducing a plurality of compositions to the pathway, wherein each of the compositions singly interferes with the operation of the metabolic pathway. In certain instances, the plurality of compositions inhibits the parasite to a degree greater than the sum of the compositions used singly, that is, exhibits a synergistic effect. Embodiments of a plurality of compositions include gabaculine and sulfadiazine; NPMG and sulfadiazine; SHAM and gabaculine; NPMG and pyrimethamine; NPMG and cycloguanil (which inhibits Apicomplexan DHFR [TS]), and other inhibitors and competitors of interrelated cascades of plant-like enzymes. Wherein the effect of inhibitors together is greater than the sum of the effects of each alone, the synergistic combination retards the selection of emergence of resistant organisms and is more effective than the individual components alone.

In various embodiments, the interfering composition acts on a latent bradyzoite form of the parasite, or multiple infecting Apicomplexan parasites simultaneously, or on conjoint infections with other pathogenic microorganisms which also utilize the plant-like metabolic pathway.

A method of determining the effectiveness of a composition in reducing the deleterious effects of an Apicomplexan in an animal, include: a) identifying a composition that inhibits growth or survival of an Apicomplexan parasite in vitro by interfering with a plant-like metabolic pathway and b) determining a concentration of the composition in an animal model that is non-toxic and effective in reducing the survival of the parasite in the animal host and/or the deleterious effects of the parasite in the animal.

Developing a lead compound that inhibits an Apicomplexan parasite is accomplished by a) identifying a plant-like metabolic pathway in an Apicomplexan parasite and b) identifying a composition that interferes with the operation of the pathway as a lead compound.

A composition which inhibits a specific life cycle stage of an Apicomplexan parasite by interfering with a plant-like metabolic pathway that utilizes a component encoded by a nuclear gene includes gabaculine; a composition including an enzyme in a metabolic pathway in an Apicomplexan parasite that is selectively operative in a life-cycle stage of the parasite includes the enzymes alternative oxidase, and UDP glucose starch glycosyl transferase. A composition comprising SHAM and 8-OH-quinoline inhibits the alternative oxidase in the latent bradyzoite form of an Apicomplexan parasite.

A method to identify a plant-like gene encoding a component of a plant-like metabolic pathway in an Apicomplexan parasite is a) obtaining a strain of E. coli that is deficient for a component of the metabolic pathway, said deficiency causing the strain to require supplemented media for growth; b) complementing the E. coli with a gene or portion of the gene encoding a component of the metabolic pathway in the Apicomplexan parasite; and c) determining whether the complemented E. coli is able to grow in unsupplemented media, to identify the gene.

Another method for identifying a plant-like gene product of a metabolic pathway in an Apicomplexan parasite is a) contacting the parasite with a gene probe; and b) determining whether the probe has complexed with the parasite from which the identity of the gene product is inferred.

A method for identifying a plant-like gene product of a metabolic pathway in an Apicomplexan parasite also includes: a) cloning and sequencing the gene; and b) determining whether the gene is homologous to a plant gene which encodes a plant enzyme with the same function.

A method for identifying a plant-like gene product in a metabolic pathway in an Apicomplexan parasite is a) contacting the parasite or its enzyme with a substrate for the plant-like enzyme; b) measuring enzyme activity; c) determining whether the enzyme is operative; and d) inhibiting activity of the enzyme in vitro with an inhibitor.

Identifying a gene or gene product in an Apicomplexan parasite which possesses an organelle transit sequence which transports a protein, wherein the protein is not necessarily an enzyme in a metabolic pathway, but is identified because it has a characteristic organelle transit sequence is also within the scope of the invention.

The invention also relates to a diagnostic reagent for identifying the presence of an Apicomplexan parasite in a subject, where the subject includes a domestic or livestock animal or a human. The reagent may include all or a portion of a component of the plant-like pathway, an antibody specific for an enzyme that is a component of a plant-like metabolic pathway in the parasite, or all or part of a nucleotide sequence that hybridizes to a nucleic acid encoding a component of the pathway. A diagnostic assay that identifies the presence of an Apicomplexan parasite or specific life-cycle stage of the parasite may use the diagnostic reagents defined herein.

A diagnostic reagent for identifying the presence of an Apicomplexan parasite, includes an antibody specific for an enzyme that is part of a plant-like metabolic pathway.

A diagnostic assay for the presence of an Apicomplexan parasite in a biological sample includes: a) contacting the sample with an antibody selective for a product of a plant-like metabolic pathway that operates in an Apicomplexan parasite; and b) determining whether the antibody has complexed with the sample, from which the presence of the parasite is inferred. Alternatively, the assay is directed towards a nucleotide sequence. In both these cases, appropriate antibody or nucleotide sequences are selected to distinguish infections by different Apicomplexans.

An aspect of the invention is a vaccine for protecting livestock animals, domestic animals or a human against infection or adverse consequences of infection by an Apicomplexan parasite. The vaccine may be produced for an Apicomplexan parasite in which a gene encoding a component of a plant-like metabolic pathway in the parasite is manipulated, for example, deleted or modified. When the gene is deleted or modified in the live vaccine, the component of the pathway may be replaced by the presence of the product of an enzymatic reaction in tissue culture medium. The vaccine strain can then be cultivated in vitro to make the vaccine.

A vaccine for protecting animals against infection by an Apicomplexan parasite is based on an Apicomplexan parasite in which the parasite or a component of a metabolic pathway in the parasite is used.

The vaccine may use a component of the pathway that is operative at a particular life stage of the parasite. A suitable component is the AroC gene from T. gondii or P. falciparum.

A method of treatment for an infection in a subject by an Apicomplexan parasite includes the following steps: a) obtaining an inhibitor of a plant-like metabolic pathway in an Apicomplexan parasite; and b) administering an effective amount of the inhibitor to the subject.

BRIEF DESCRIPTIONS OF DRAWINGS

FIGS. 1A–C illustrates the heme synthesis pathway and the effect of GSAT in T. gondii.

FIG. 1A diagrams the heme synthesis pathway. FIGS. 1B and 1C show that uptake of tritiated uracil by tachyzoites (RH strain) is inhibited by gabaculine, an inhibitor of GSA aminotransferase. P/S=pyrimethamine and sulfadiazine. Note that ALA synthase is also present in T. gondii and constitutes an alternative pathway for heme synthesis.

FIGS. 2A–B shows unique lipid degradation in the glyoxylate cycle in T. gondii.

FIG. 2A is a schematic representation of the glyoxylate cycle. FIG. 2B shows uptake of tritiated uracil by tachyzoites (RH strain) is inhibited by 3-NPA (0.005 to 5 mg: G/ML). Note this inhibitor also effects succinate dehydrogenase, so its inhibitory effect does not unequivocally support presence of the glyoxylate pathway.

FIG. 3A is a schematic representation of a pathway which demonstrates alternative oxidase as an alternative pathway for generation of energy in Apicomplexan parasites. FIG. 3B shows that uptake of tritiated uracil by tachyzoites (RH strain) is inhibited by SHAM.

FIG. 4A is a schematic representation of the pathway for conversion of shikimate to chorismate in T. gondii. The inhibitor of EPSP synthase is NMPG. FIG. 4B shows uptake of tritiated uracil by tachyzoites (RH strain) is inhibited by NPMG. Toxicity of NPMG was assessed by its ability to prevent growth of human foreskin fibroblasts (HFF) after 4 days, as measured by tritiated thymidine uptake and microscopic evaluation. FIG. 4C shows product rescue of NPMG's inhibitory effect on EPSP synthase by PABA. The effect of PABA on sulfadiazine is similar, but the effect on pyrimethamine, as predicted reduces the enzyme to the levels that were present when media alone was utilized, as measured by the uracil uptake.

| S = | sulfadiazine |
| PYR = | pyrimethamine |
| PABA = | para amino benzoic acid. |

FIG. 4D shows functional and enzymatic evidence for the shikimate pathway in T. gondii with inhibition of EPSP synthase enzyme activity by 1 mM glyosate. Squares, without glyphosate. Circles, with glyphosate. FIG. 4E shows evidence for the shikimate pathway in P. falciparum with functional evidence for the shikimate pathway in P. falciparum. Glyphosate inhibition of in vitro growth of asexual erythrocytic forms and PABA and folate antagonism of growth inhibition. Effect of NPMG on C. parvum was not abrogated by PABA. This suggests that either uptake of PABA by C. parvum differs or effect of NPMG is on a different branch from the shikimate pathway in C. parvum.

Figure 8:
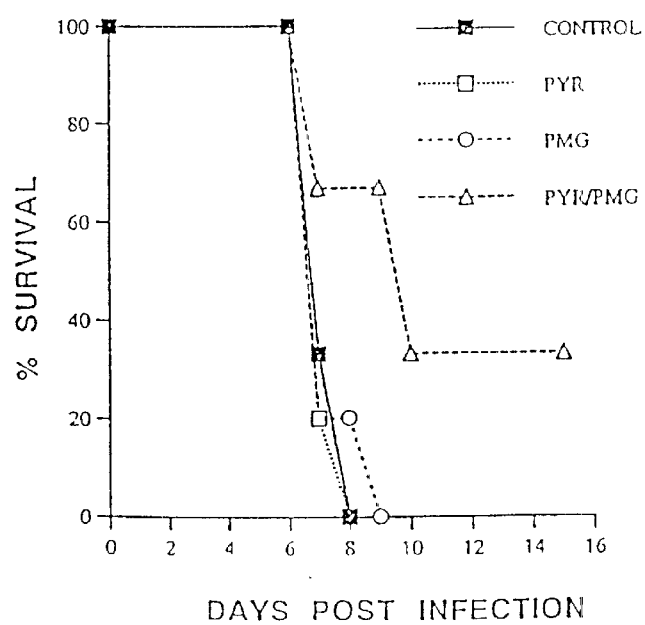

FIG. 8 shows the effect of NPMG, pyrimetharnine, and pyrimethamine plus NPMG on survival of mice following intraperitoneal infection with 500 tachyzoites of the RH strain of T. gondii. Dosage of NPMG was 200 mg/kg/day and pyrimethamine was 12.5 mg/kg/day).

FIG. 9 shows nucleotide (SEQ ID NO: 1) and deduced amino acid (SEQ ID NO: 2) sequences of T. gondii chorismate synthase cDNA. The asterisk indicates the stop codon.

FIG. 10 shows results of CLUSTAL X alignments of the deduced amino acid sequences of the putative *T. gondii,* chorismate synthase (SEQ ID NO: 2) with the corresponding sequences from Synechocystis, (SEQ ID NO:38) *S. cerevisiae,* (SEQ ID NO: 39) *S. lycopersicum,* (SEQ ID NO: 40) *N. crassa* (SEQ ID NO: 41) and *H. influenza* (SEQ ID NO: 42). Dashes were introduced to maximize alignment. Amino acids which are identical in all 6 organisms are underlined. The percent identity of the chorismate synthase from each organism with the *T. gondii* protein was calculated to be as follows: Synechocystis (51.4%), *S. cerevisiae* (49.6%), *S. lycopersicum* (47.2%), *N. crassa* (45.0%) and *H. influenza* (44.5%). The large internal regions in the *T. gondii* sequence which have no counterparts in the chorismate synthases of other organisms, were not included in this calculation.

FIG. 11 shows the transit sequences of (SEQ ID NO: 44) *Zea mays* and *T. gondii* chorismate synthases (SEQ LD NO: 43). The sequences of the transit peptide directing the transport of the wx+protein into maize amyloplasts and chloroplasts and the portion of the *T. gondii* chorismate synthase sequence which is homologous are aligned. The amino acid sequence is given in one letter code. * indicates an identical amino acid in the Wx *Zea mays* and *T. gondii* sequences. • indicates homologous amino acids in the Wx *Zea mays* and *T. gondii* sequences.

The transit sequence in the Wx *Zea mays* protein (UDP-glucose-starch-glycosyl transferase) begins at amino acid number 1 and ends at amino acid number 72. The portion (amino acids 359 to 430) of *P. falciparum* AroC which corresponds to the novel internal sequence of the *T. gondii* AroC which includes the amino acids homologous to the maize protein, is as follows: IPVENMSTKK-ESDLLYDDKGECKNMSYHSTIQNNEDQILNSTKGFM-PPKNDKNFNNIDDYNVTFNNNEEKLL (SEQ ID NO:5). The *T. gondii* portion of the AroC (chorismate synthase) sequence which demonstrates 30% homology begins at amino acid number 330 and ends at amino acid number 374. The first (single) arrow indicates the processing site of *Zea may* UDP glucose glycosyl transferase transit peptide and the second (double) arrow indicates the location at which the mature protein begins.

FIG. 12 shows *P. falciparum,* chorismate synthase, cDNA (SEQ ID NO: 3) and deduced amino acid (SEQ ID NO: 4) sequences.

DESCRIPTION OF THE PREFERRED EMBODIMENT

This invention uses components of plant-like interrelated metabolic pathways that are essential for growth or survival of Apicomplexan parasites. The pathways are generally not operative in animals and do not include psbA or PPi phosphofructokinase and are not encoded in the plastid. Components include enzymes, products, targetting peptides, nucleotide sequences encoding the enzymes or peptides, and promoters, as targets for specific inhibitors. Use of these pathways provide a rational and novel framework to discover, characterize and develop medicines, diagnostic reagents and vaccines for Apicomplexan parasites.

Medicines, diagnostic reagents and vaccines are based upon interrelated plant-like enzyme cascades involved in the synthesis or metabolism or catabolism of Apicomplexan nucleic acids, amino acids, proteins, carbohydrates or lipids, energy transfer and unique plant-like properties of these enzymes which are shared with, and provide a basis for, discovery of other parasite proteins which have unique organelle targeting signals or unique promoter regions of the genes which encode the proteins. Synergistic combinations of inhibitors of the enzymes or proteins or nucleic acids which encode them are particularly useful in medicinses.

To select pathways for use in the invention:

a) plant textbooks and the published literature are reviewed for properties characteristic of plants, but generally not animals, databases such as Genbank or the Apicomplexan ESTs are reviewed to identify homologous Apicomplexan and plant-like genes; and b) Western, northern and southern analyses, PCR, and ELISAs are used to recognize, or are based upon, for example, plant proteins and genes, to determine whether components of the pathways are present in Apicomplexans;

c) cloning, isolation and sequencing of genes and creation of gene constructs are used to identify Apicomplexan plant-like genes and their functions;

d) assays of enzyme activity are used to determined the operation of plant-like systems;

e) functions of parasite enzymes or part of a parasite enzyme are demonstrated by complementation of a yeast or bacteria deficient in the enzyme, or product rescue, or other methods to demonstrate enzyme activity;

f) activity of compounds, (i.e., inhibitors) known to abrogate effect of the plant-like enzyme, protein, or nucleic acid which encodes them in vitro and in vivo, are tested singly or in a plurality, for ability to abrogate the enzyme activity and against Apicomplexan parasites alone or together, and in conjoint Apicomplexan, bacterial and fungal infections, The general compositions of this invention are:

A. Inhibitory compounds based on:
  a) targeting proteins by
    (i) substrate competition and transition state analogues
    (ii) product competition
    (iii) alteration of active site directly or by modification of secondary structure or otherwise altering function of the active site
    (iv) interfering with protein function with antibody
    (v) targeting an organelle or protein within an organelle using a toxic compound linked to a targeting sequence.
  b) targeting nucleic acids encoding proteins (antisense, ribozymes)
  c) targeting a component of the protein or nucleic acid (as above)

B. Diagnostic reagents (genes, proteins, antibodies) in ELISAs, western blots, DNA, RNA assays C. Vaccines (live knockout, live mutated, components—genes, proteins, peptides, parts of genes constructs, etc.)

Specific examples of components of plant-like Apicomplexan pathways are in Table 1. Compounds known to inhibit these enzymes or properties in Apicomplexans and/or other microorganisms are listed in Table 1, as are novel ways to target them in Apicomplexans.

TABLE 1A

Apicomplexan plant-like metabolic pathways, components and inhibitors

| Function | Gene name | Enzyme or property | Known inhibitors of enzymes or property | Basis for novel inhibitor |
|---|---|---|---|---|
| HEME SYNTHESIS | HemL | glutamate-1-semialdehyde aminotransferase (GSAT) | 3-amino-2,3-dihydrobenzoic acid (Gabaculine); 4-amino-5-hexynoic acid; 4-amino-5-fluoropentanoic acid; 4-amino-5-hexynoic acid (γ acetylenic GABA); 2-amino-3-butanoic acid (vinyl glycine); 2-amino-4-methoxy-trans-3-butanoic; 4-amino-5-fluoropentanoic acid | S, AS, R |
| | GltX | glutamyl-tRNA synthase | — | |
| | HemA | glutamyl-tRNA reductase | — | |
| SHIKIMATE PATHWAY | | | | |
| Chorismate synthesis | AroA | 3-enolpyruvylshikimate phosphate synthase (3-phosphoshikimate-1 carboxyvinyltransferase) | N-(phosphonomethyl) glycine (glyphosphate), sulfosate, EPSP synthase inhibitors 4 and 5, hydroxymaonate inhibitors of EPSP synthase** | S, AS, R |
| | AroB | dehydroquinate synthase (5-dehydroquinate dyhdrolase) | | |
| | AroC | chorismate synthase 5-enolpyruvylshikimate 3-phosphate phospholyase) | — | |
| | AroC-ts | AroC transit sequence | | |
| | AroD | dehydroquinate dehydratase | — | |
| | AroE | shikimate dehydrogenase | — | |
| | AroF | 3-deoxy-d-arabino-heptulosonate 7 phosphate synthase | — | |
| | AroG | chorismate mutase (7-phospho-2-dehydro-3-deoxy-arabino-heptulate aldolase) | — | |
| | AroH | 3-deoxy-d-arabino-heptulosante 7 phosphate synthase | — | |
| | AroI | shikimate 3-phosphotransferase (shikimate kinase) | — | |
| Ubiqinone synthesis | UbiA | 4-hydroxybenzoate octaprenyltransferase | — | S, AS, R |
| | UbiB | 3-oxtaprenyl-4-hydroxybenzoate carboxylyase | — | |
| | UbiC | chorismate synthase | — | |
| Tyrosine synthesis | TyrA | prephenate dehydrogenase | — | S, AS, R |
| | TyrB | aromatic acid aminotransferase (aromatic transaminase) | — | |
| | TyrC | cyclohexadienyl dehydrogenase | — | |
| Tryptophan synthesis | TrpA | tryptophan synthase alpha sub unit | — | S, AS, R |
| | TrpB | tryptophan synthase beta sub unit | — | |
| | TrpC | indole-3-glycerol phosphate synthase (anthranilateisomerase) (indoleglycerol phosphate synthase) | — | |
| | TrpD | anthranilate phosphorbosyltransferase | — | |
| | TrpE | anthranilate synthase component I | — | |
| | TrpF | phosphoribosyl anthranilate isomerase | — | |
| | TrpG | anthranilate synthase component II | — | |
| Phenylalinine Synthesis | PheA | Prephenate dehydratase (phenol 2-mono-oxygenase), chorismate mutase | — | S, AS, R |
| | PheB | Catechol 1,2-deoxygenase (phenol hydroxylase) | — | |
| | PheC | Cyclohexadienyl dehydrataseU | — | |
| Folate Synthesis | pabA | 4-amino-4-deoxy chorismate synthase II, amidotransferase | — | S, AS, R |

TABLE 1A-continued

Apicomplexan plant-like metabolic pathways, components and inhibitors

| Function | Gene name | Enzyme or property | Known inhibitors of enzymes or property | Basis for novel inhibitor |
|---|---|---|---|---|
| | pabB | 4-amino-4-deoxy chorismate synthase I, binding component | — | |
| | pabC | 4-amino4-deoxy chorismate lyase | — | |
| Menaquinone, enterobactin synthesis | Enta | Isochorismate synthase | — | S, AS, R |
| | Entb | 2,3 dihydro 2,3 dihydroxy benzoate dehydrogenase | — | |
| | Enfc | 2,3 dihydro 2,3 dihydroxy benzoate synthetase | — | |
| ORGANELLE TRANSIT | AroC-ts | Transport into plastid, organelle targeting | — | S, AS, R |
| ALTERNATIVE RESPIRATION | AOX | Alternative oxidase | 8-hydroxyquinoline, 3-hydroxyquinone, salicylhydroxamic acid, monoctone, benzhydroaxamic acid, m-Chlorohydroxamic acid, propylgallate, disulfuram, and others | S, AS, R,D |
| GLYOXYLATE CYCLE | MS | Malate synthase | — | S, AS, R |
| | ICL | Isocitrate lyase | 3NPA, itaconic acid, 3 nitro propanol | |

Key:
S, modified substrate competitor;
AS, antisense;
R, ribozyme; Directed at active site,
D; None known, —
*EPSP synthase inhibitor 4 refers to 3-(phosphonooxy)-4-hydroxy-5-[N-(phosphonomethyl-2-oxoethyl)amino-1-cyclohexene-1-carboxylic acid (3α, 4α, 5β), compound with diethyl ethanamide. EPSP synthase inhibitor 5 refers to shortened R phosphonate.
**A new, aromatic analogue of the EPSP synthase enzyme reaction intermediate 1 has been identified, which contains a 3-hydroxymalonate moiety in place of the usual 3-phosphate group. This simplified inhibitor was readily prepared in five steps from ethyl 3,4-dihydroxybenzoate. The resulting tetrahedral intermediate mimic is an effective, competitive inhibitor versus S3P with an apparent K(i) of 0.57 +/− 0.06 muM. This result demonstrates that 3-hydroxymalonates exhibit potencies comparable to aromatic inhibitors containing the previously identified 3-malonate ether replacements and can thus function as suitable 3-phosphate mimics in this system. These new compounds provide another example in which a simple benzene ring can be used effectively in place of the more complex shikimate ring in the design of EPSP synthase inhibitors. Furthermore, the greater potency of the tetraheral intermediate mimic versus the glycolate derivative and the 5-deoxy analog, again confirms the requirement for multiple anionic charges at the dihydroxybenzoate 5-position in order to attain effective inhibition of this enzyme.
The following were identified: inhibition of *Toxoplasma gondii* (Tg), *Plasmodium falciparum* (Pf), and *Cryptosporidium parvum* (Cp) EPSP synthase by N-phosphonomethylglycine (NPMG); Tg and Pf chorismate synthase (AroC) cDNA and deduced amino acid sequences; a novel sequence in the Tg chorismate synthase gene (AroC-ts) a portion of which is homologous with the plastid transit sequence of *Zea mays* (sweet corn). The Pf chorismate synthase (AroC) also has a corresponding novel and unique internal region. Cp, *Eimeria bovis* (Eb) genomic DNA which hybridizes with Tg AroC (chorismate synthase). Inhibition of Tg in vitro by NPMG abrogated by para-aminobenzoate (PABA). Inhibition of Pf in vitro by NPMG abrogated by PABA and folate. Inhibition of Tg EPSP synthase activity by NPMG in vitro. Synergism of NPMG with pyrimethamine, with sulfadiazine and with SHAM for Tg in vitro; Synergy of NPMG with pyrimethamine against Tg in vivo; SHAM and 8-hydroxyquinoline inhibited Tg, Pf, Cp in vitro; reactivity of Tg protein of ~66Kd with 5 antibodies (monoclonal and polyclonal to *VooDoo lily* and *T. brucei* alternative oxidases) and reduction to monomer similar to *VooDoo lily* and *T. brucei* alternative oxidases on a reducing gel; Identification of Tg cDNA and genomic DNA PCR products using primers based on conserved sequences in other alternative oxidases which are probed and sequenced; Tg, Pf, Cp inhibited by high concentrations of gabaculine. Reactivity of Tg protein of ~40Kd with 3 antibodies to GSAT (polyclonal α soybean, barley and synechococcus GSATs and not preimmune sera). Reactivity of Cp protein of ~40Kd with a barley GSAT. Inhibition of Tg, Pf, Cp in vitro by 3NPA; Reactivity of Tg protein with polyclonal antibodies to cotton malate synthase and cotton isocitrate lyase but not preimmune sera. In screening Tg cDNA library α GSAT antibody reactive clones are identified and are sequenced. Tg chorismate synthase and dehydroquinase enzymatic activities are demonstrated.

TABLE 1B

Components of Plant-Like Metabolic Pathways and Inhibitors

| Function | Gene name | Enzyme or property | Known inhibitors of enzyme or property | Basis for novel inhibitor |
|---|---|---|---|---|
| BRANCHED-CHAIN AMINO ACID SYNTHESIS (VALINE, LEUCINE, | ahas | acetyhydroxy acid synthase | Imidazolinones imazquin = 2-[4,5-dihydro-4-methyl-4-(1-methylethyl)-5-oxo-1H-imidazol-2-yl]-3-quinolinecarboxylic acid; imazethapyr = 2-[4,5-dihydro-4-methyl-4-(1-methylethyl)-5-oxo- | S, AS, R |

TABLE 1B-continued

Components of Plant-Like Metabolic Pathways and Inhibitors

| Function | Gene name | Enzyme or property | Known inhibitors of enzyme or property | Basis for novel inhibitor |
|---|---|---|---|---|
| ISOLEUCINE) | | | 1H-imidazol-2-yl]-3-pyridinecarboxylic acid; imazapyr = ( )-2-[4,5-dihydro-4 methyl-4-(1-methylethyl)-5-oxo-1H-imidazol-2-yl[-3-pyridinecarboxylic acid, Sulfonylureas chlorimuron = 2-[[[[(4-chloro-6-methoxy-2-pyrimidinyl)amino]carbonyl]amino] sulfonyl]benzoic acid; chlorsulfuron = 2-chloro-N-[[(4-methoxy-6-methyl-1,3,5-triazin-2-yl) amino]carbonyl]benzene sulfonamide; nicosulfurn = 2-[[[[(4,6-dimethoxy-2-pyrimidinyl) amino]carbonyl] amino]sulfonyl]-N,N-dimethyl-3-pyridinecarboxamide; primisulfuron = 2-[[[[(4,6-bis(difluoromethoxy)-2-pyrimidinyl) amino]carbonyl] amino]sulfonyl]benzoic acid; thifensulfuron = 3-[[[[(4-methoxy-6-methyl-1,3,5-triazin-2-yl) amino] carbonyl]amino]sulfonyl]-2-thiophene-carboxylic acid; tribenuron = 2-[[[[(4-methoxy-6-methyl-1,3,5-triazin-2-yl)methylamino]carbonyl]amino] sulfonyl]benzoic acid; sulfometuron = 2-[[[[(4,6-dimethyl-2-pyrimidinyl) amino]carbonyl] amino]sulfonyl]benzoic acid; metsulfuron = 2-[[[[(4-methoxy-6-methyl-1,3,5-triazin-2-yl)amino]carbonyl]amino]sulfonyl] benzoic acid; halosulfuron = , Sulfonanilides flumetsulam = N-(2,6-difluorophenyl)-5 methyl[1,2,4]triazolo[1,5-a]pyrimidine-2-sulfonamide | |
| | Kar | Keto-acid reducto isomerase | HOE 704 | |
| | ipd | isopropylmalate dehydrogenase | O-oisobutenyl oxalhydroxamate | |
| SYNTHESIS OF ADDTIONAL "ESSENTIAL" AMINO ACIDS (e.g. histidine, methionine, lysine, threonine) | | | | S, A, R,D |
| Histidine synthesis | gpd+ | glycerol phosphate dehydratase | phosphon c acid derivatives of 1,2,4 triazole | |
| methionine synthesis | ms+ | methionine synthesis+ | — | |
| lysine synthesis | ls+ | lysine synthesis+ | inhibitors of lysine synthesis+. | |
| Threonine synthesis | ts+ | threonine synthesis + | — | |
| GLUTAMINE GLUTAMATE SYNTHESIS | gs+ gts+ | glutamine synthase, glutamate synthetase* | glufosinate = 2-amino-4-hydroxy methyl phosphinyl, butaonic acid — | S, AS, R, D |
| LIPID SYNTHESIS | acc+ | acetyl co A carboxylase | Arloxyphenoxypro-pionates fenoxaprop = ( )-2-[4-[(6-chloro-2-benzoxazolyl)oxy] phenoxy]propanoic acid; fluazifop-P = (R)-2-[4-[[5-(trifluoromethyl)-2-pyridinyl]oxy]phenoxy]propanoic acid | S, AS, R ,D |

TABLE 1B-continued

Components of Plant-Like Metabolic Pathways and Inhibitors

| Function | Gene name | Enzyme or property | Known inhibitors of enzyme or property | Basis for novel inhibitor |
|---|---|---|---|---|
| | | | quizalofop = ( )-2-[4-[(6-chloro-2-quinoxalinyl)oxy]phenoxy] propanoic acid, Cyclohexanediones clethodim = (E,E)-( )-2-[1-[[(3-chloro-2-propenyl)oxy]imino] propyl]-5-[2-(ethylthio)propyl]-3-hydroxy-2-cyclohexen-1-one; sethoxydim = 2-[1-(ethoxyimino) butyl]-5-[2-(ethylthio)propyl]3-hydroxy-2-cyclohexen-1-one | |
| | ps | palmitic synthase | | |
| | oas | oleic acid synthase | | |
| | las | linoleic acid synthase | | |
| | licas | linoleneic acid synthase | | |
| STARCH SYNTHESIS | wx, gbss, sss | UDP glucose starch glucosyl transferase (a starch synthase) other starch synthases | — | S, AS, R |
| | be, glgB, lgc, sbeI, II, III | Q or branching enzyme | — | |
| AUXIN GROWTH REGULATORS | — | Auxin analogue | Phenoxyaliphatic acid (2,4-D = (2,4-dichlorophenoxy) acetic acid; 2,4-DB = 4-(2,4-dichlorophenoxy) butanoic acid; MCPP = ; MCPA = (4-chloro-2-methylphenoxy) acetic acid; 2,4-DP = ) Benzoic acids dicamba = 3,6-dichloro-2-methoxybenzoic acid, Picolinic acids [Pyridines] picloram = 4-amino-3,5,6-trichloro-2-pyridinecarboxylic acid; clopyralid = 3,6-dichloro-2-pyridinecarboxylic acid; triclopyr = [(3,5,6-trichloro-2-pyridinyl)oxy]acetic acid; fluroxypry = [(4-amino-3,5-dichloro-6-fluoro-2-pyridinyl) oxy]acetic acid; | S, AS, R |
| | ias | indoleacetic acid synthase | — | |
| GIBBERELLIN SYNTHESIS | coaps | copalylpyrophosphate synthase | Phosphon D, Amo-1618 | S, AS, R |
| | ks | kaurene synthase | Cycocel | |
| | kox | kaurene oxidase | Phosphon D, | |
| | kaox | kaurene acid oxidase | Ancymidol, Paclobutrazol | |
| | gas | giberellic acid synthase | — | |

Key:
S, modified substrate competitor;
AS, antisense;
R, ribozyme;
D, direct inhibitor, alteration of target. These are suitable because they are unique to Apicomplexans. Unique to Apicomplexans means that either they do not exist in animals (e.g., acetohydroxyacid synthase, linoleic acid synthase, starch-amylose or amylopectin synthase, Q or branching enzyme, UDP glucose, starch glycosyl transferase or have unique antigenic or biochemical properties distinct from those of animals (e.g. acetylco A carboxylase).
*Also present in animals
+Other enzymes in these pathways unique to Apicomplexans.

TABLE 1B-continued

Components of Plant-Like Metabolic Pathways and Inhibitors

| Function | Gene name | Enzyme or property | Known inhibitors of enzyme or property | Basis for novel inhibitor |
|---|---|---|---|---|

+Enzymes involved in the synthesis of these essential amino acids include the following:
Lysine: homocitrate synthase, homocitrate dehydrase (Euglena, fungi); aspartokinase, aspartate semialdehyde dehydrogenase, dihydropicolinate synthase, dihydropicolinate reductase, $\Delta^1$ piperideine-2,6-dicarboxylate transferase, N-succinyl-ϵ-keto-α-aminopimelate transaminase, N-succinyl-L,L,α-ϵ-diaminopimelate desuccinylase, L,L α-ϵ diaminopimelate epimerase, meso-α ϵ diaminopimelate decarboxylase.
Inhibitors of lysine synthesis include: +2-4-Amino-4-carboxybutyl azridine-2-carboxylic acid(3) (aziridino-diaminopimelate [DAP], aziDAP); N-Hydroxy.DAP4; N-amino DAP5; 4 methylene DAP 6; 3,4 didehydro DAP; 4 methylene DAP 4.
Methionine: L-homoserine acyltransferase, o-succinylhomoserine sulfhydrolase, L-homocysteine transferase, (to activate methionine-but not exclusively in plants: S-adenosylmethionine [SAM] synthase, SAM-methyltransferase, SAM decarboxylase, S-adenosylhomocysteine hydrolase)
Threonine: L homoserine kinase, O-phospho-L-homoserine (threonine) synthase
Isoleucine, valine: L-threonine deaminase, acetohydroxy acid synthase, acetohydroxy acid isomeroreductase, dihydroxy acid dehydrase, branched-chain amino acid glutamate transaminase.
Leucine: isopropylmalate synthase, α-isopropylmalate isomerase, β-isopropylmalate dehydrogenase, α ketoisocaproate transaminase.
Histidine: phosphoribulosyl formimino-5-aminolmidazol-4-carboxamide ribotide amidocyclase, imidazol glycerol phosphate dehydrase, imidazole acetol phosphate transaminase, histidinol phosphate phosphatase, L-histidinol dehydrogenase.
Additional herbicides which disrupt cell membranes include Diphenyl ethers [nitro phenyl ethers = ] (acifluorfen = 5-[2-chloro-4-(trifluoromethyl)phenoxy]-2-nitrobenzoic acid; fomeasafen = 5-[2-chloro-4-(trifluoromethyl) phenoxy]-N-(methylsulfonyl)-2-nitrobenzamide; lactofen = ( )-2-ethoxy-1-methyl-2-oxoethyl 5-[2-chloro-4-(trifluoromethyl)phenoxy]-2-nitrobenzoate; oxyflurfen = 2-chloro-1-(3-ethoxy-4-nitrophenoxy)-4-(trifluoromethyl) benzene), Other bentazon = 3-(1-methylethyl)-(1H)-2,1,3-benzothiadiazin-4(3H)-one 2,2-dioxide above. Additional herbicides which disrupt pigment production include clomazone = 2-[(2-chlorohenyl)methyl]-4,4-dimethyl-3-isoxazolidinone; amitrole = 1H-1,2,4-triazol-3-amine; norflurazon = 4-chloro-5-(methy amino)-2-(3-(trifluoromethyl) phenyl)-3(2H)-pyridazinone; fluridone = 1-methyl-3-phenyl-5-[3-(trifluoromethyl)phenyl]-4(1H)-pyridinone.

Enzymes in the heme synthesis [with a default ALA synthase pathway], shikimate pathway, alternative generation of energy and glyoxylate cycle are exemplified (Table 1A) and the others (Table 1B) are suitable for the practice of the invention.

As outlined succinctly above, the present invention includes new methods and compositions to treat, diagnose and prevent human and veterinary disease due to Apicomplexan parasites. Apicomplexan infections include those due to *Toxoplasma gondii* (toxoplasmosis), Plasmodia (malaria), Cryptosporidia (cryptosporidiosis), Eimeria (eimeriosis), Babesia (babesiosis), Theileria (theileriosis), *Neospora caninum*, and others. An Apicomplexan parasite, *Toxoplasma gondii*, is a representative of other Apicomplexan parasites because Apicomplexan parasites appear to be phylogenetically related and have organelles and enzymes which are critical for their growth and survival. The presence of plant-like pathways/enzymes is confirmed in Apicomplexans by a) the effect of known inhibitors of the pathways in plants using in vitro and in vivo assays; b) Western, Northern and Southern hybridization analyses; c) isolation and comparison of relevant genes; d) demonstration of enzymatic activity; e) demonstration of immunologically reactive proteins which cross-react with proteins in plants; f) complementation of organisms which lack a gene or part of the gene encoding an enzyme with a parasite gene which encodes the enzyme; and/or g) recognition of plant-like transit sequences. In vitro assays include product rescue (i.e., complete or partial abrogation of the effect of an inhibitor by providing the product of the reaction and thus bypassing the need for the enzyme which catalyzes the reaction. The assays are based on inhibition of the parasite i.e. restriction of growth, multiplication or survival of the parasite. Another measure of infection is "parasite burden" which refers to the amount (number) of parasites present as measured in vivo in tissues of an infected host. Another measure of infection is destruction of host tissues by the parasites. Inhibitors reduce parasite burden and destruction of host tissues caused by the parasites. Preferably the inhibitors must not be toxic or carcinogenic to the parasites' host and for in vitro assays not be toxic to cells in culture.

Enzymes of the newly detected plant-like pathways provide novel, unique and useful targets for antimicrobial therapy. These unique pathways and enzymes are within the plastid, glyoxosomes, cytoplasm or mitochondria. In addition, not suggested before for these parasites, some enzymes used in these pathways are encoded by genes within the nucleus.

Plant-like pathways detected in Apicomplexan parasites include a) the 5-carbon heme biosynthesis pathway that utilizes glutamate as a carbon skeleton for synthesis and requires the unique enzyme glutamate-1-semialdehyde aminotransferase; b) the mobilization of lipids in the glyoxylate cycle which is a unique pathway that includes the enzymes isocitrate lyase and malate synthase; c) the generation of energy by an alternative pathway which includes a unique alternative oxidase and/or other unique pathways and enzymes for generating energy in the mitochondria or plastid; and, d) the conversion of shikimate to chorismate utilized in the synthesis of ubiquinone, aromatic amino acids and folate by plants, but not humans. The shikimate pathway includes the enzyme 3-phospho-5-enolpyruvylshikimate (EPSP) synthase, chorismate synthase, and chorismate lyase, as well as a number of enzymes unique to plants, fungi, bacteria, and mycobacteria, but not to animals. Inhibitors of some of these enzymes also provide information about the functioning and targeting of the enzymes.

The heme synthesis pathway involves enzymes encoded in the nucleus and imported to the plastid. This pathway is present in Apicomplexans including *T. gondii, P. falciparum,* and *Cryptosporidia parvum*. Inhibitors of the enzyme GSAT in the pathway include gabaculine (3-amino-2,3-dihydro benzoic acid), 4-amino-5-hexanoic acid, and 4-amino-5-fluropentanoic acid.

The glyoxylate cycle, reported to be present in plants, fungi, and algae, is also present in *T. gondii*. The cycle uses lipids and converts them to C4 acids through a series of biochemical reactions. One of the last steps in this series of reactions is dependent on the isocitrate lyase enzyme and another on the malate synthase enzymes. Inhibitors of these enzymes include 3-nitropropionic acid and itaconic acid.

The alternative respiratory pathway, present in a range of organisms including some bacteria, plants, algae and certain protozoans (trypanosomes), is present in *T. gondii, Cryptosporidia parvum,* and *Plasmodium falciparum* (in the latter parasite, two clones designated W2 and D6 were inhibited). The pathway is inhibited by a range of compounds including salicylhydroxamic acid, 8-hydroxyquinoline, Benzyhydroxamic acid (BHAM), m-Chlorohydroxamic acid (m-CLAM), Propylgallate, Disulfuram and others.

Enzymes involved in the synthesis of chorismate, including those which convert shikimate to chorismate, and enzymes which generate folate, aromatic amino acids and ubiquinone from chorismate in plants, are present in *T. gondii, Plasmodium falciparum, Cryptosporidium parvum,* and Eimeria. Inhibitors include N-(phosphonomethyl) glycine (glyphosate, sulfosate and others). A full-length *T. gondii* cDNA sequence (SEQ ID NO: 1) encoding a chorismate synthase from this pathway and the deduced amino acid sequence provide information useful in developing novel antimicrobial agents. The *T. gondii* chorismate synthase has features in common with other chorismate synthases and entirely unique features as well. The unique features are novel sequences not shared with chorismate synthases from other organisms but with homology to an amyloplast/chloroplast transit sequence of *Zea mays* (sweet corn). A *P. falciparum* cDNA sequence (SEQ ID NO: 3) encoding chorismate synthase and its deduced amino acid sequence also provide information useful for developing novel antimicrobial agents.

The genomic sequences provide information about regulation of the gene (e.g., unique promoter regions) and such unique regions enable targeting their regulatory elements with antisense.

A part of the novel internal sequence (i.e., SCSFSESAASTIKHERDGSAATLSRERASDGRTTSRH-EEEVERG) (SEQ ID NO: 43) in the *T. gondii* AroC (chorismate synthase) gene has homology with the chloroplast/amyloplast targeting sequence of *Zea mays* (sweet corn) wx (UDP glucose-starch-glycosyl transferase) protein (i.e., MAALATSQLVATRAGLGVPDASTFRRG AAQGLRGARASAAADTLSMRTSARAAPRHQQQARR GGRFPSLVVC) (SEQ ID NO: 44). This transit sequence provides a novel way to target *T. gondii* enzymes that move from the cytoplasm into the plastid and is generally applicable to targeting any subcellular organelle. The *P. falciparum* AroC (chorismate synthase) has a corresponding novel internal sequence.

Additional pathways found in Apicomplexan parasites include the synthesis of branched chain amino acids (valine, leucine and isoleucine) and acetohydroxy acid synthase is the first enzyme in the branched chain amino acid synthesis pathway, inhibited by sulfonylureas and imidazolinones, as well as the synthesis of other "essential" amino acids, such as histidine, methionine, lysine and threonine. Starch synthesis, including starch synthases, the UDP-glucose-starch glycosyl transferase, and debranching enzymes and enzymes of lipid, terpene, giberellin and auxin synthesis, are part of other pathways in Apicomplexan parasites. Down modulation of the UDP-glucose starch glycosyl transferase pathway leads to a switch from amylose to amylopectin synthesis and thus the bradyzoite phenotype.

Demonstration of presence of one enzyme or the gene that encodes it in a known pathway implies presence of the full pathway. Thus, enzymes in parasite metabolic pathways that can be inhibited include: glutamyl-tRNA synthetase; glutamyl-tRNA reductase; prephenate dehydrogenase; aromatic acid aminotransferase (aromatic transaminase); cyclohexadienyl dehydrogenase; tryptophan synthase alpha subunit; tryptophan synthase beta subunit; indole-3-glycerol phosphate synthase (anthranilate isomerase), (indoleglycerol phosphate synthase); anthranilate phosphoribosyltransferase; anthranilate synthase component I; phosphoribosyl anthranilate isomerase; anthranilate synthase component II; prephenate dehydratase (phenol 2-monooxygenase); catechol 1,2-deoxygenase (phenol hydroxylase); cyclohexadienyl dehydratase; 4-hydroxybenzoate octaprenyltransferase; 3-oxtaprenyl-4-hydroxybenzoate carboxylyase; dehydroquinate synthase (5-dehydroquinate hydrolase); chorismate synthase (5-enolpyruvylshikimate 3-phosphate phosph-lyase); dehydroquinate dehydratase; shikimate dehydrogenase; 3-deoxy-d-arabino-heptuloonate 7 phosphate synthase; chorismate mutase (7-phospho-2-dehydro-3-deoxy-arabino-heptulate aldolase); 3-deoxy-d-arabino-heptuloonate 7 phosphate synthase; shikimate 3-phosphotransferase (shikimate kinase); UDP glucose starch glycosyl transferase; Q enzymes; acetohydroxy acid synthase; glutamate-1-semialdehyde 2,1-aminotransferase; chorismate lyase; malate synthase; isocitrate lyase; and 3-enolpyruvylshikimate phosphate synthase (3-phosphoshikimate-1 carboxyvinyltransferase).

Recombinant protein produced by constructs with genes encoding these enzymes in *E coli* or in other expression systems is useful for producing antibodies and obtaining a crystal structure. Native enzyme is isolated. The expressed and native proteins are used to design and test new inhibitors in enzyme assays. Expressed and native (from varied life-cycle stages) proteins are used and the expressed protein is a source of the enzyme, and the enzyme assay is carried out in the presence and absence of the inhibitors, either alone or in combination and controls include the buffer for the enzyme alone. The crystal structure is useful for characterizations of enzyme active site(s), secondary structure, transit sequence, substrate and product interactions. The design of additional inhibitors is carried out using published methods such as modifying substrates as had been done with inhibitors of EPSP synthase as well as high-throughput screening of available compounds.

Certain pathways are shown to be affected by inhibitors which are synergistic in vitro. Examples of synergistic inhibitors in vitro are gabaculine (heme synthesis) and SHAM (alternative energy generation); NPMG and SHAM; NPMG and sulfadiazine; and NPMG and pyrimethamine. Gabaculine and sulfadiazine are an additive combination in vitro.

An aspect of the invention is identifying potential targets for therapeutic intervention by considering nuclear as well as organellar genes as part of the production of enzymes for unique plant-like pathways. For example, the protein synthesis of plant-like proteins that is also demonstrated in Apicomplexan parasites suggests not only conservation of plastid genes but also conservation of nuclear genes which encode enzymes that act inside or outside the plastid, from an ancestor that is common to Apicomplexan parasites and algae. Many vital metabolic pathways of algae (often shared with their evolutionary relatives, higher plants) also are conserved in the Apicomplexan parasites, whether or not the pathways involve the plastid. Consequently, Apicomplexan parasites are sensitive to inhibitors that block several of these unique pathways. Combined attack on multiple targets retards the emergence/selection of resistant organisms. Considering nuclear and organellar genes has the dual advantage of rapidly identifying conservation of specific pathways and simultaneously identifying both target sites and lead compounds for therapeutic drug development.

An aspect of the invention is a plurality of inhibitors, singly or in combination, directed against enzymes and/or genes encoding a different metabolic pathway. Examples of inhibitors suitable for practice of the present invention include GSAT, 3NPA, SHAM, 8-OH-quinoline, and NPMG, sulfonylureas, imidazolinones, other inhibitors of EPSP synthase or chorismate synthase which include competitive substrate analogues, transitional state inhibitors and direct active site inhibitors as well as other known compounds (Table I). Some pluralities of inhibitors produce synergistic effects.

Improved treatments against Apicomplexan parasites result from a variety of options:

1. some compositions may inhibit the operation of more than one pathway, thereby producing a strong effect and lessening the probability of resistance to the drug emerging because more than one mutation may be required;
2. some compositions may inhibit more than one step in a pathway;
3. some pluralities of compositions may have synergistic effects, producing more effective drugs; and
4. some compositions may target pathways operative exclusively during a life cycle of the parasite, making them more selective e.g. against the latent phase.
5. some compositions may inhibit other microorganisms (including other Apicomplexans.)

An additional detail of the invention is that representative Apicomplexan parasites, notably *T. gondii*, are used for assaying candidate inhibitors. The invention is directed at effects of inhibitors of the unique plant-like pathways in Apicomplexan, alone and in combination. Organisms used for the assays include *T. gondii* tachyzoites, bradyzoites and a mutant that expresses 50% tachyzoite and 50% bradyzoite antigens. Unique plant enzymes and pathways that were found to be inhibited by compounds shown to inhibit plant pathways in Apicomplexans include: (1) glutamate-1 semialdehyde amino transferase, an enzyme important in heme synthesis, (2) isocitrate lyase, an enzyme important in utilization of lipids, (3) alternative oxidase enzyme complex, enzymes important in energy production and (4) 3-phospho-5-enolpyruvylshikimate synthase (EPSP synthase), an enzyme important in conversion of shikimate to chorismate which is a precursor for synthesis of folate, ubiquinone, and certain amino acids essential for survival.

The invention provides a rational, conceptual basis for development of novel classes of antimicrobial agents that inhibit Apicomplexan parasites, unique diagnostic reagents, and attenuated vaccines. The inhibitors provide lead compounds for the development of antimicrobial agents. Conserved enzyme active sites or parts of the molecules or genes that encode the protein which are targeted by the inhibitors provide the basis for development of new but related ways to target the enzymes, such as related protein inhibitors, intracellular antibodies, antisense DNA, and ribozymes.

Inhibitors are effective against more than one parasite (e.g. *T. gondii, P. falciparum* and *C. parvum*) and enzymes in these pathways also are present in other bacterial and fungal pathogens such as *Pneumocystis carinii, Mycobacterium tuberculosism Staphylococcus aureus,* and *Hemophilus influenza,* but not animals. Thus, inhibitors of these pathways affect susceptible microorganisms which concurrently infect a host. Because enzymes are utilized differentially in different parasite life-cycle stages, stage-specific inhibitors are within the scope of the invention. Genes encoding the enzymes in Apicomplexans are identifiable. The genes encoding the enzymes are effectively knocked out in these parasites by conventional techniques. "Knockout" mutants and reconstitution of the missing genes of the parasite demonstrate the importance of gene products to the varying life-cycle stages of the parasite which are identified using antibodies to proteins and ability to form cysts in vivo which define the life cycle stages. The parasites in which a gene is knocked out are a useful basis for an attenuated vaccine. The genes encoding the enzymes or parts of them (e.g., a novel targeting sequence) or the proteins themselves alone or with adjuvants comprise a useful basis for a vaccine. The pathways and enzymes of the invention are useful to design related antimicrobial agents. The sequences and definition of the active sites of these enzymes, and pathways, and organelle (e.g., plastid) targeting sequences provide even more specific novel and unique targets for rational design of antimicrobial agents effective against Apicomplexan parasites. For example, proteins which interact with the enzyme and interfere with the function of the enzyme's active site, or are competitive substrates or products or intracellular antibodies (i.e., with a gene encoding the Fab portion of an antibody that targets the protein the antibody recognizes), or antisense nucleic acid or targeted ribozymes that function as inhibitors are useful, novel antimicrobial agents. Enzymes of the invention are a novel basis for unique diagnostic tests. Because some of these pathways are important in dormant parasites, or in selecting the dormant or active life cycle stages, they are especially important as antimicrobial agent targets for life cycle stages of the parasite for which no effective antimicrobial agents are known or as diagnostic reagents which ascertain the duration of infection.

Identification of the pathways in Apicomplexan parasites provides additional enzyme targets present in these pathways which are not present in or are differentially expressed in animal cells. Identification of the interrelatedness of these pathways with each other provides the basis for the development and demonstration of combinations of inhibitors which together have an effect which is greater than the expected additive effect (i.e., synergistic). The meaning of synergism is that compound A has effect A', compound B has effect B', compounds A+B have an effect greater than A'+B'. Synergism is characteristic of inhibitors of these pathways because an initial pathway affected by an inhibitor often provides a product used as a substrate for another pathway so the inhibition of the first enzyme is amplified. These pathways or their products are interrelated. Therefore, the enzymes or DNA which encodes them are targeted by using two or more inhibitors leading to an additive or synergistic effect. Examples include the additive effect of gabaculine and sulfadiazine and the synergistic effects of NPMG and sulfadiazine and NPMG and pyrimethamine. One or more of the inhibitors preferentially affect one of the life cycle stages of Apicomplexan parasites.

Some enzymes are preferentially used by specific stages of the parasites. Detection of an enzyme of this type or a nucleic acid encoding it offers a novel diagnostic test not only for presence of a parasite, but also for identification of the stage of the parasite.

Genes encoding enzymes in pathways of the present invention are "knocked out" using techniques known in the art. A parasite with a gene knocked out is said to be attenuated either because the gene expression of the enzyme is stage specific so the parasite cannot become latent, or because the knocked out enzyme is essential for parasite survival. The importance of an enzyme's functions in various life-cycle stages is determined using a mutant-knockout-complementation system. In the former case, the attenuated parasite is useful as a vaccine because the "knocked out" gene is critical for the parasite to establish latency. Its administration to livestock animals results in immunity without persistence of latent organisms. Mutants with the gene "knocked out" also can be selected because when the parasites are grown in vitro they are grown in the presence of product of the enzymatic reaction to allow their survival. However, such attenuated parasites do not persist in vivo in the absence of the product and, consequently they are useful as vaccines, for example, in livestock animals. The genes that encode the protein also are used in DNA constructs to produce proteins themselves or the proteins or peptides are used in immunized animals. These constructs are used to elicit an immune response and are used for vaccines alone or with adjuvants. Specific examples are incorporation of the gene for alternative oxidase or chorismate synthase in a construct which has a CMV promoter and expresses the protein following intramuscular injection (i.e., a DNA vaccine). This type of construct, but with genes not identified or described as plant-like, has been used as in a vaccines that protect against bacterial and protozoal infections.

Plant-like pathways in Apicomplexans were inhibited in vitro. An Apicomplexan GSAT enzyme that is part of a heme synthesis pathway was targeted with inhibitors. A gene with homology to ALA synthase was identified by analysis of the *T. gondii* ESTs (Washington University *T. gondii* gene Sequencing project), indicating that *T. gondii* has alternative methods for synthesis of ALA. An Apicomplexan glyoxylate cycle was analyzed to determine the sensitivity of tachyzoites and bradyzoites to glyoxylate cycle inhibitors. Specifically, Apicomplexans have isocitrate lyase and malate synthase which present a unique pathway for lipid metabolism that is targeted by inhibitors. Apicomplexan alternative oxidase is targeted, as evidenced by effects of inhibitors of alternative oxidase on this pathway and its expression and immunolocalization in tachyzoites and bradyzoites; Apicomplexan parasites have a metabolically active EPSP synthase enzyme involved in conversion of shikimate to chorismate. These four metabolic pathways, i.e., heme synthesis, shikimate pathway, alternative generation of energy, and the glyoxylate cycle are all exemplified in *T. gondii.* To show that inhibition was specific for key enzymes in these pathways that are generally absent or used only rarely in mammalian cells, product inhibition studies were used in vitro. For example, growth of *T. gondii* is sensitive to NPMG that inhibits the synthesis of folic acid via the shikimate pathway. Because mammalian hosts lack the entire shikimate pathway, it is unlikely that the parasites can obtain either PABA or its precursor chorismate from the host cells so provision of PABA circumvents the need for the substrate pathway for folate synthesis and rescues the EPSP synthase inhibition by NPMG.

Further proof of the presence of the plant-like pathways arises from biochemical assays for an enzyme in analogous plant pathways and isolation of encoding genes. Genes are identified by search of available expressed sequence tags (ESTs, i.e., short, single pass cDNA sequences generated from randomly selected library clones), by PCR amplification using primer sequences derived from published conserved sequences of plant genes with parasite genomic DNA or parasite DNA libraries (Chaudhuri et al., 1996), by the screening of Apicomplexan DNA expression libraries with antibodies to previously isolated homologous proteins or the DNA which encodes them and by complementation of *E. coli* or yeast mutants deficient in an enzyme. Genes isolated by these techniques are sequenced which permits identification of homologies between plant and Apicomplexan genes using sequence databases such as Genbank. These assays confirm that an enzyme and the gene encoding it are present in Apicomplexan parasites. *E. coli* mutants and yeast deficient in the enzyme are complemented with plasmid DNA from *T. gondii* cDNA expression libraries or the isolated gene or a modification (e.g., removing a transit sequence) of the isolated gene which allows the production of a functional protein in the *E. coli* or yeast, demonstrating that the gene encoding the enzyme is functional. Homologous genes in *T. gondii, P. malaria,* Cryptosporidia, Neospora, and Eimeria are identified when relevant plant or *T. gondii* genes are used as probes to DNA obtained from these organisms and the genes are identified either by cloning and sequencing the DNA recognized by the probe or by using the probe to screen the relevant parasite libraries. Genomic DNA is sequenced and identifies unique promoters which are targeted. Unique parts of the genes were identified in the sequences and provide additional antimicrobial agent targets, diagnostic reagents and vaccine components or bases for vaccines. Clade and bootstrap analyses (Kohler et al., 1997) establish the phylogenetic origin of novel, sequenced, parasite genes and this indicates other related antimicrobial agent targets based on components, molecules, and pathways of phylogenetically related organisms. Gene products are expressed and utilized for enzyme assays and for screening novel inhibitors, for making antibodies for isolation of native protein, for x-ray crystallography which resolves enzyme structures and thus establishes structure-function relationships and enzyme active sites which are useful for the design of novel inhibitors.

Immunoelectronmicroscopy using antibodies to enzymes such as chorismate synthase, alternative oxidase, malate synthase or isocitrate lyase immunolocalizes the enzymes within the parasite and determines their location, in particular whether they are in plant-like organelles. Apicomplexan transit peptides are identified by their homology to known transit peptides in other species. Attachment of reporter proteins to the wild type transit peptide, or deletion or mutations of the transit peptide or portion of the peptide or gene encoding it, and then characterization of targeting of these constructs alone or in association with reporter constructs establishes that the amino acid sequences of the transit peptide determine intracellular localization and site of function of proteins with this sequence. Stage specificity of these enzymes is determined in vitro by using antibodies to stage-specific antigens in inhibitor-treated cultures, by Western or Northern analyses (detection), by enzyme assays using selected parasite life cycle stages, by using RT PCR (Kirisits, et al, 1996) and a DNA competitor as an internal standard to quantitate the amount of mRNA in parasite samples, by ELISA (quantitation) and by determining whether a parasite with the gene knocked out can develop a bradyzoite phenotype in vitro in the appropriate bradyzoite inducing culture conditions. Stage specificity in vivo is determined by observing effects of the inhibitors on different life cycle stages in acutely vs. chronically infected mice and by determining whether a parasite with the gene knocked out can form cysts in vivo. Useful techniques to develop diagnostic reagents for detection of these proteins or nucleic acids include ELISAs, Western blots, and specific nucleotides used as probes.

EXAMPLES

Example 1

Novel In Vitro Assay Systems to Assess Antimicrobial Effects on T. gondii

New in vitro and in vivo assay systems were developed to determine whether plant metabolic pathways are present in Apicomplexans. New elements include use of longer culture times (e.g., extending the duration of the assay to ≧6 days is also a unique and useful aspect of this invention, because it allows demonstration of antimicrobial effect for compounds which have to accumulate prior to exerting their effect), use of Me49 PTg and R5 strains in vitro, employing synergistic combinations of NPMG and low dosage pyrimethamine in vivo, and assays of parasitemia in vivo using competitive PCR.

Improvements were developed in the assays reported by Mack et al. (1984) and Holfels et al. (1994) to measure T. gondii replication in tissue culture. The improvements are based on microscopic visual inspection of infected and inhibitor treated cultures, and on quantitation of nucleic acid synthesis of the parasite by measuring uptake of $^3$H uracil into the parasite's nucleic acid. Uracil is not utilized by mammalian cells. Parasites present as tachyzoites (RH, Ptg, a clone derived from the Me49 strain), bradyzoites (Me49), and R5 mutants (mixed tachyzoite/bradyzoites of the Me49 strain that can be stage switched by culture conditions) (Bohne et al., 1993; Soete et al., 1994; Tomovo and Boothroyd, 1995; Weiss et al, 1992) are suitable for assay systems used to study effects of inhibitors. Only the RH strain tachyzoites, cultured for up to 72 hours, had been used in previously reported assays. The use of Me49, Ptg, and R5 mutant are unique aspects of the methods used in these assays in this invention.

Results using the assay systems are shown in FIGS. 4, 6–8. In these assays toxicity of a candidate inhibitor was assessed by its ability to prevent growth of human foreskin fibroblasts (HFF) after 4 days and after 8 days as measured by tritiated thymidine uptake and microscopic evaluation. Confluent monolayers of HFF were infected with tachyzoites or bradyzoites. Inhibitor was added one hour later. Non-toxic doses were used in parasite growth inhibition assays. Parasite growth was measured by ability to incorporate tritiated uracil during the last 18 hours of culture.

Example 2

Detection of Plant-like Pathways in Apicomplexans

Using assays disclosed herein, some of which were novel, Apicomplexan parasites were found to contain at least four metabolic pathways previously thought to be unique to plants, algae, bacteria, dinoflagellates, and fungi. Specifically, the presence of a unique heme synthesis pathway, an alternative oxidase pathway, a glyoxylate cycle and a pathway necessary for the biosynthesis of chorismate and its metabolites were explored. Growth of the parasite, T. gondii, depends upon these pathways. To examine T. gondii for the presence of plant-like and algal metabolic pathways, certain inhibitors of metabolic pathways are suitable to apply because of their ability to prevent growth of the parasite in tissue culture.

Pathways which are present in Apicomplexans were analyzed as follows: First, T. gondii tachyzoites were tested to see if they were sensitive in vitro to inhibition by specific inhibitors of target pathways. Then bradyzoites are tested. Positive results for each pathway provided presumptive evidence that the inhibitor targets were present and that their activities are important for parasite survival and growth. The inhibitors effective in vitro were screened for activity in vivo in mice. An example of an effective combination in vivo is NPMG and low dosage pyrimethamine.

The presence of an enzyme was further confirmed by product rescue in vitro, in which the product abrogates the need for its synthesis by the enzyme. An example was rescue by PABA for the reaction catalyzed by EPSP synthase. Other methods to demonstrate the presence of an enzyme and thus the pathway include functional enzyme assays, complementation of mutant E. coli strains, PCR, screening of a T. gondii expression library with antibodies or DNA probes, and immunostaining of Western blots. For some enzymes, identification of a partial sequence of a gene in an EST library in the gene database led to cloning and sequencing the full length gene. Demonstration of the enzymes also is diagnostic for presence of the parasites. Examples are demonstration of T. gondii and C. parvum GSAT and T. gondii alternative oxidase and T. gondii isocitrate lyase and malate synthase by Western analysis and cloning and sequencing of the T. gondii and P. falciparum chorismate synthase gene. Reagents (gene probes and antibodies) obtained during characterization of genes from T. gondii are used to detect homologous enzymes and pathways in other Apicomplexan parasites. Examples were using the T. gondii chorismate synthase gene to probe P. falciparum, Eimeria bovis and Cryptosporidium parvum genomic DNA. Other examples are using heterologous plant DNA to detect Apicomplexan GSAT, isocitrate lyase, malate synthase, and alternative oxidase genes. Such genes are used as DNA probes to screen libraries to clone and sequence the genes to identify PCR products.

Example 3

Effects of Inhibitors In Vitro on T. gondii

Using the assays described in Example 1, five compounds that restrict the growth of T. gondii in vitro were identified:

(i) Gabaculine
(ii) NPA
(iii) SHAM (Salicylhydroxamic Acid);
(iv) 8-hydroxyquinoline
(v) NPMG Specifically these inhibitors act as follows:

i. The Effect of Gabaculine, an Inhibitor of the 5-Carbon Heme Synthesis Pathway, on the Growth of *T. gondii*

Figure 1A:
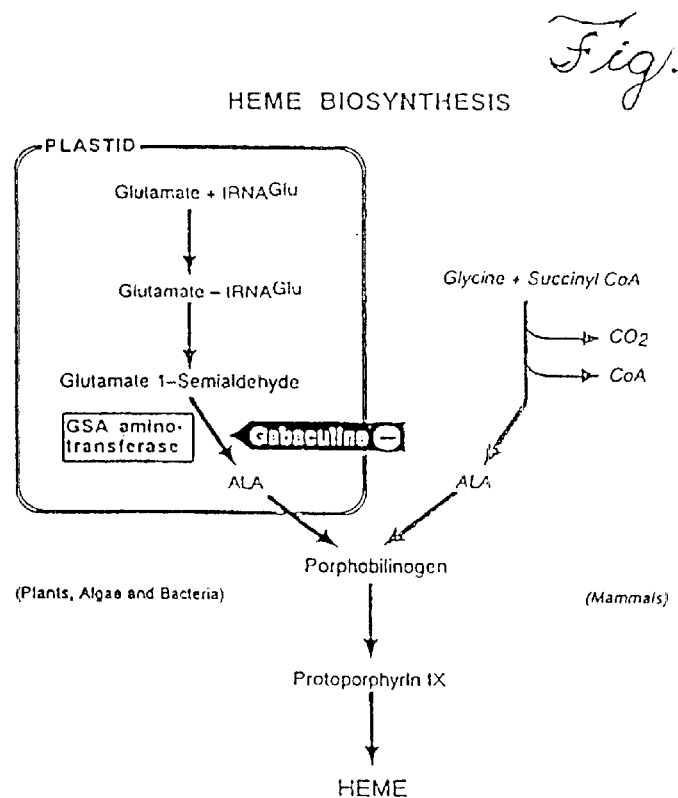

FIG. 1A compares heme biosynthesis in plants, algae and bacteria with heme biosynthesis in mammals. In higher plants and algae, ALA is produced in the plastid by the action of GSA aminotransferase on glutamate 1-semialdehyde. In mammals, ALA is formed through the condensation of glycine and succinyl CoA. ALA is subsequently converted to heme. In one dinoflagellate and *T. gondii* both pathways are present.

Inhibitors of plant heme synthesis pathway restrict the growth of *Toxoplasma gondii* in vitro. As shown in FIG. 1A, the synthesis of δ-aminolevulinic acid (ALA), the common precursor for heme biosynthesis, occurs in the plastid of plants, algae and Apicomplexan parasites by the 5-carbon pathway and ALA synthesis occurs by a different pathway in animals. The pathway in animals involves the condensation of glycine and succinyl CoA. The data in FIG. 1B–C and a Western blot utilizing an antibody to the homologous soybean, and barley, and synechococcus GSATs, demonstrate that *Toxoplasma gondii* utilizes the 5-carbon pathway for ALA synthesis and therefore heme biosynthesis. 3-amino 2,3-dihydroxybenzoic acid (gabaculine) inhibits GSA in the heme synthesis pathway.

First the toxicity of gabaculine was assessed by its ability to prevent growth of human foreskin fibroblasts (HFF) as measured by $^3$H-thymidine uptake and microscopic evaluation. Non-toxic doses were used in parasite growth inhibition assays. In vitro parasite growth inhibition assays included confluent monolayers of HFF infected with tachyzoites (RH) or mutant Me49 (R5). Gabaculine was added 1 hour later. Parasite growth was measured by the ability to incorporate $^3$H-uracil during the last 18 hours of culture. In addition, parasite growth was evaluated microscopically in Giemsa stained slides.

Figure 1B:
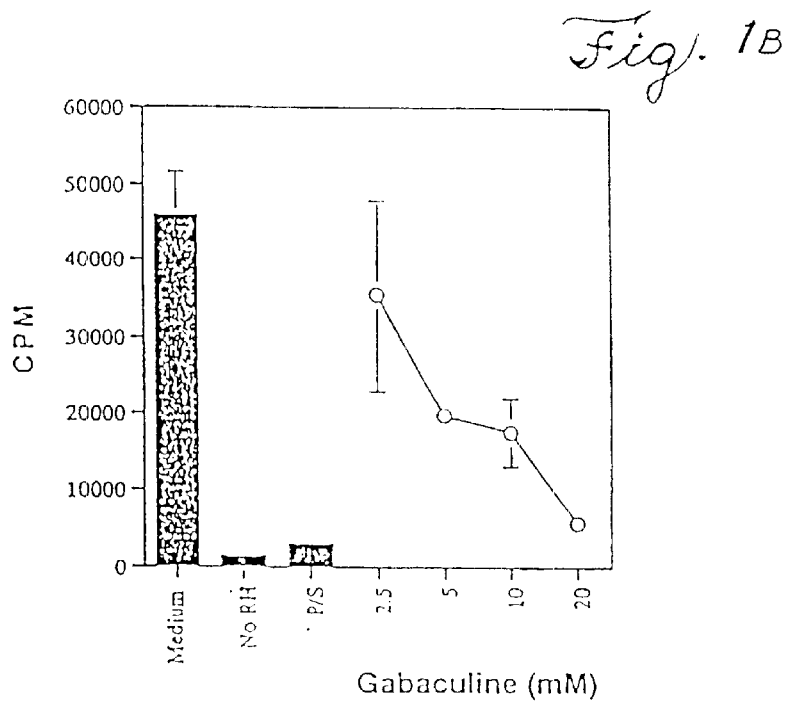

Toxoplasma organisms were grown in human foreskin fibroblasts alone and in the presence of different concentrations of gabaculine (3-amino-2,3-dihydrobenzoic acid). Growth was measured by the ability of *T. gondii* to incorporate tritiated uracil. This compound was effective at inhibiting the growth of *T. gondii* at the 20 mM concentration. FIG. 1B demonstrates the ability of gabaculine (a specific inhibitor of GSA aminotransferase) to restrict the growth of *T. gondii* in an in vitro assay over a 4 day period. *T. gondii* growth is measured by ability of the parasites to incorporate tritiated uracil and is expressed as counts/minute (CPM) on the Y-axis. The X-axis describes how the *T. gondii* cultures were treated. Cultures that were grown in medium (medium) produced a CPM of around 45,000. If no *T. gondii* were added to the cultures (no RH), a CPM of around 2,000 was observed. Pyrimethamine (0.1 μm/ml) and sulphadiazine (12.5 μg/ml) added to cultures resulted in a marked reduction in CPM compared with untreated cultures. At a dose of 5 mM gabaculine restricted around 50% of CPM and at a dose of 20 mM it almost completely inhibited parasite growth, with counts of about 5,000 CPM.

Figure 1C:
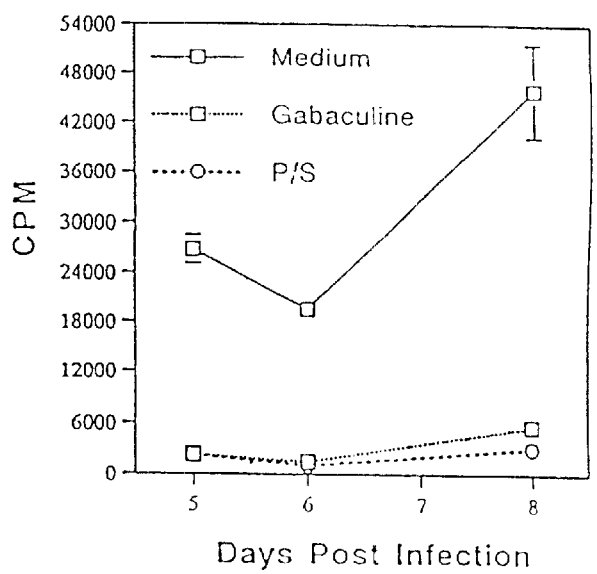

FIG. 1C demonstrates the ability of gabaculine to inhibit the growth of *T. gondii* over 8 days in culture. *T. gondii* growth is measured by ability of the parasites to incorporate tritiated uracil and is expressed as counts/minute (CPM) on the Y-axis. The X-axis represents days post infection. Parasite growth was evident in the cultures where no drug was added (medium) over the entire time course. Parasite growth was restricted in cultures with 20 mM gabaculine (gabaculine) over the 8 day time course. Similarly, parasite growth was restricted in cultures with pyrimethamine and sulphadiazine (P/S) over the 8 day time course. Similar concentrations showed no toxicity to the foreskin fibroblasts indicating the specificity of this compound for *T. gondii*. Parallel cultures, fixed and stained with Giemsa and examined by microscopy, clearly demonstrated that *T. gondii* growth was substantially inhibited in the presence of 3-amino-2,3-dihydrobenzoic acid. The results in FIGS. 1B and 1C indicate that *T. gondii* utilizes the 5-carbon ALA synthesis pathway.

Figure 7:
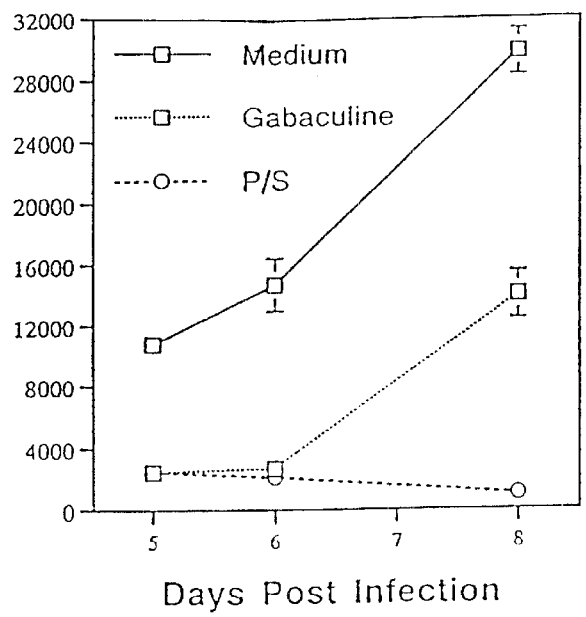
FIG. 7 shows the effects of gabaculine (20 mM) on growth of tachyzoites/bradyzoites (R5) in human foreskin fibroblasts, over 8 days as determined by uracil uptake. Note increased uptake of uracil by the $8^{th}$ day.

FIG. 7 demonstrates the ability of gabaculine to inhibit the growth of the mutant R5 strain of *T. gondii* over 8 days in culture. This mutant strain is atovaquone resistant and possesses certain characteristics of the tachyzoite stage and certain characteristics of the bradyzoite stage. *T. gondii* growth is measured by their ability to incorporate tritiated uracil and is expressed as counts/minute (CPM) on the Y-axis. The X-axis represents days post infection. Parasite growth was evident in the cultures where no drug was added (medium) over the entire time course. Parasite growth was restricted in cultures with 20 mM gabaculine (gabaculine) over the first 6 days of culture, after which a marked increase in parasite growth was detected. Furthermore groups of proliferating organisms which resembled tissue cysts were observed in similarly treated cultures. Parasite growth was restricted in cultures with pyrimethamine and sulphadiazine (P/S) over the entire 8 day time course. Residual R5 organisms in treated cultures at 8 days begin to incorporate uracil again and some of them appeared cyst-like. Therefore, *T. gondii* cyst-like structures are selected by gabaculine treatment of cultures. Specific immunostaining of such cultures treated with gabaculine for tachyzoite and bradyzoite specific antigens demonstrates that gabaculine selects bradyzoites. Table 2 is a schematic representation of experiments designed to test the hypothesis that tachyzoites utilize both conventional oxidase and alternative oxidases, but bradyzoites only use alternative oxidases, therefore interfering with generation of iron sulfated proteins by gabaculine treatment will select bradyzoites. The design and predicted results of stage specific immunostaining (Kasper et al., 1983) if the hypothesis were correct are shown in Table 2 and confirm the hypothesis. These results suggest that *T. gondii* has stage-specific utilization of alternative oxidases which are utilized when cell cultures are treated with gabaculine because it depletes heme and thus depletes iron sulfated proteins used in conventional respiration.

In summary, 3-amino-2,3-dihydrobenzoic acid (gabaculine) is an inhibitor of the 5 carbon heme synthesis pathway present in Apicomplexan parasites. Heme synthesis occurs by a different pathway in mammalian cells and is therefore unaffected by 3-amino-2,3-dihydrobenzoic acid.

TABLE 2

Gabaculine treatment of cultures selects bradyzoites.

| Antibody used for IFA | Treatment of culture | Tachyzoite Control | Bradyzoite Control | IFA result on culture day | | |
|---|---|---|---|---|---|---|
| | | | | 0 | 2 | 6 |
| αSAG1 (expressed on tachyzoites only) | Media | | | | | |
| | Gabaculine | | | | | |
| αBSAG (expressed on bradyzoites one day after stage switch) | Media | | | | | |
| | Gabaculine | | | | | |
| αBAG5 (expressed on bradyzoites by five day after stage switch in culture) | Media | | | | | |
| | Gabaculine | | | | | |

IFA is immunofluorescent assay. SAG1 is surface antigen 1. BSAG is bradyzoite surface antigen 1. BAG5 is bradyzoite antigen 5. A. Hypothesis. B. Design and predicted results of stage specific immunostaining if hypothesis were to be correct.

Figure 2A:
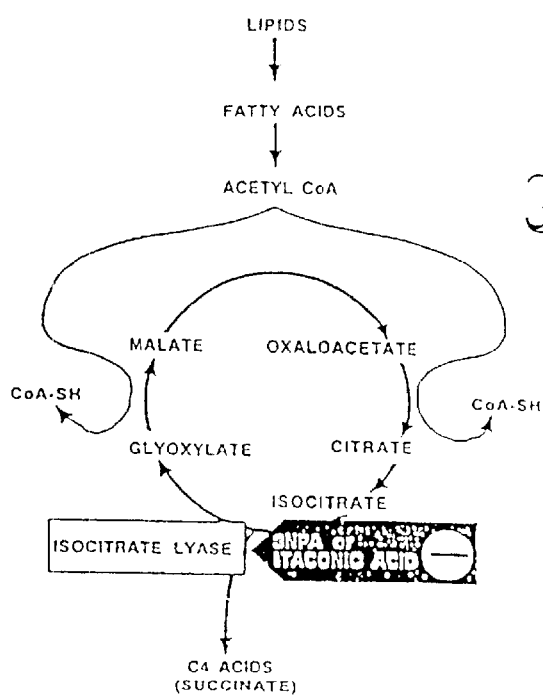
Figure 2B:
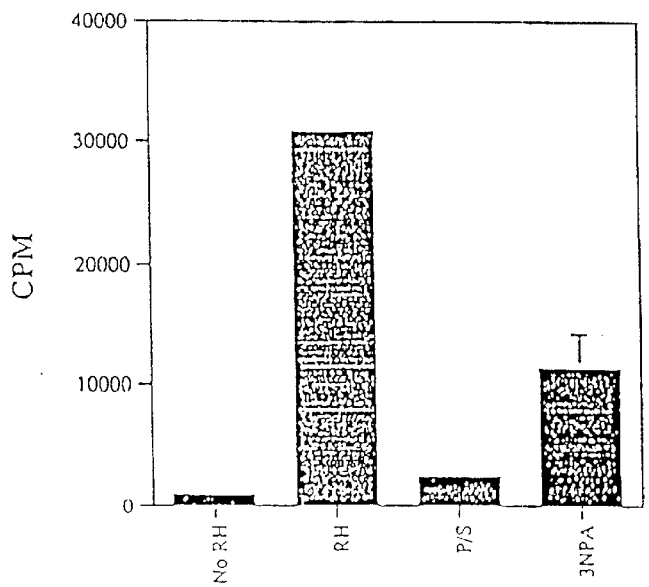

indicates no specific fluorescence of the organism;

indicates specific surface fluorescence of the organism due to presence of the antigen recognized by the antibody (e.g., αSAG1 or αBSAG);

indicates specific internal fluorescence in the organism due to presence of the antigen within the parasite recognized by the antibody (e.g., αBAG5).

ii. An Inhibitor of the Glyoxylate Cycle Restricts the Growth of *T. gondii* in vitro 3-Nitropropionic acid is an inhibitor of isocitrate lyase in the degradation of lipid to C4 and inhibits replication of *T. gondii* in vitro. FIG. 2A illustrates how the glyoxylate cycle manufactures C4 acids. Acetyl CoA, a byproduct of lipid breakdown combines with oxaloacetate to form citrate. By the sequential action of a series of enzymes including isocitrate lyase, succinate is formed. Glyoxalate, the byproduct of this reaction is combined with a further molecule of acetyl CoA by the action of malate synthase. Malate is then converted to oxaloacetate, thus completing the cycle. 3-NPA and itaconic acid are inhibitors of this pathway. FIG. 2B demonstrates the ability of 3-NPA (an inhibitor of isocitrate lyase) to restrict the growth of *T. gondii* in an in vitro assay over a 4 day period. This result indicates it is likely that *T. gondii* degrades lipids using isocitrate lyase. *T. gondii* growth is measured by their ability to incorporate tritiated uracil and is expressed as counts/minute (CPM) on the Y-axis. The X-axis described how the *T. gondii* cultures were treated. Cultures that were grown in medium (medium) produced a CPM of about 30,000. If no *T. gondii* were added to the cultures (no RH), a CPM of about 2,000 was observed. Pyrimethamine (0.1 μg/ml) and sulphadiazine (12.5 μg/ml) added to cultures resulted in a marked reduction in CPM compared with untreated cultures. A dose of 0.006 mg/ml 3-NPA (3-NPA) restricted around 60% of CPM. 3-NPA inhibits the glyoxylate cycle (isocitrate lyase) and/or succinate dehydrogenase in Apicomplexan parasites.

iii. and iv. Effect of SHAM and 8-hydroxyquinoline on Alternative Oxidase in *T. gondii*

Figure 3A:
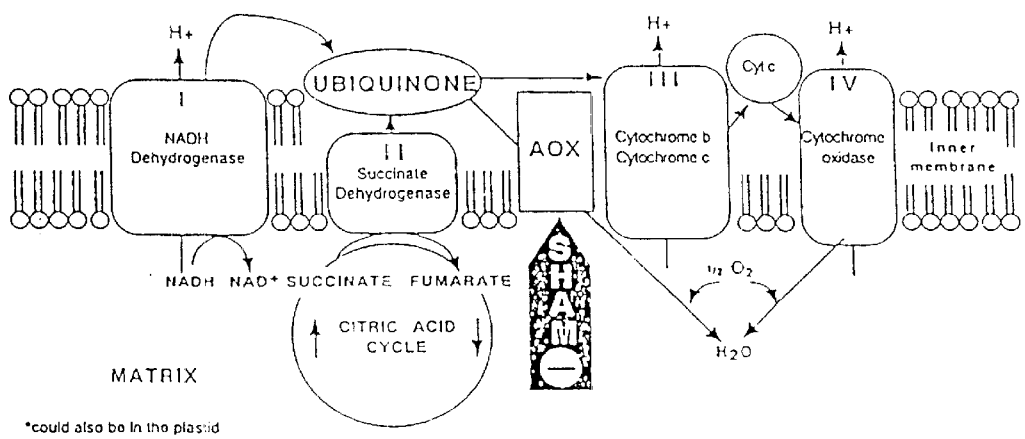

There is a metabolic pathway found in most plants and algae and in Apicomplexans, but absent in most multicellular animals. FIG. 3A describes the electron transport respiratory chain that normally occurs on the inner membrane of mitochondria. In animals, NADH and succinate produced by the action of the citric acid cycle diffuse to the electron transport chain. By a series of oxidation reactions mediated in part through the cytochromes, free energy is released. This free energy yields the potential for the phosphorylation of ADP to ATP. In plants, in addition to the conventional electron transport chain complexes, there is an alternative pathway of respiration. Alternative pathway respiration branches from the conventional pathway at ubiquinone and donates released electrons directly to water in a single four electron step. An important feature of this pathway is that it does not contribute to transmembrane potential and thus free energy available for the phosphorylation of ADP to ATP. The pathway provides a source of energy and is preferred for conditions with relatively low ATP demands. A key enzyme in this pathway is an alternative oxidase that is cyanide insensitive and does not require heme. Toxoplasma gondii utilizes the alternative oxidase for respiration.

Figure 3B:
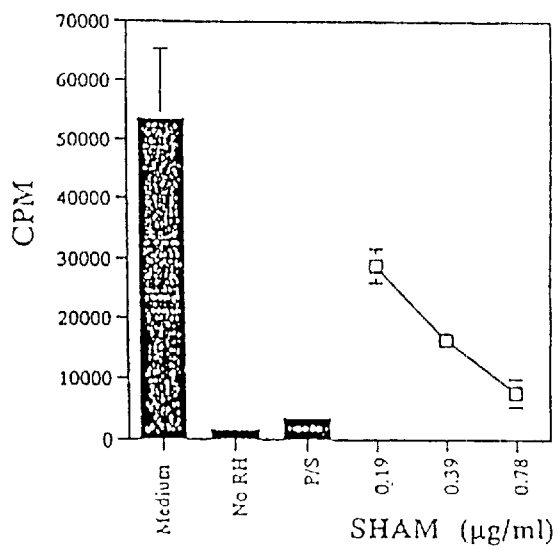

FIG. 3B demonstrates the ability of SHAM (a specific inhibitor of alternative oxidase) to restrict the growth of T. gondii in an in vitro assay over a 4 day period. The ability of these compounds to inhibit the growth of T. gondii was examined by the assay described in Example 1. T. gondii growth is measured by their ability to incorporate tritiated uracil and is expressed as counts/minute (CPM) on the Y-axis. The X-axis describes how the T. gondii cultures were treated. Cultures that were grown in medium (medium) produced a CPM of around 54,000. If no T. gondii were added to the cultures (no RH), a CPM of around 1,000 was observed. Pyrimethamine (0.1 $\mu$g/ml) and sulphadiazine (12.5 $\mu$g/ml) added to cultures resulted in a marked reduction in CPM compared with untreated cultures. A dose of 0.19 $\mu$g/ml SHAM (0.19) restricted around 50% of CPM and at a dose of 0.78 $\mu$g/ml it essentially inhibited parasite growth, with counts of about 8,000 CPM.

Salicylhydroxamic acid (SHAM) and 8-hydroxyquinoline are inhibitors of the alternative oxidase and are also effective against T. gondii, presumably by inhibiting the alternative pathway of respiration. Salicylhydroxamic acid and 8-hydroxyquinoline inhibit the alternative oxidase of T. gondii tachyzoites. Since alternative oxidative respiration does not occur in mammals, this makes antimicrobial compounds targeting this pathway therapeutic candidates.

V. Effect of NPMG

Figure 4A:
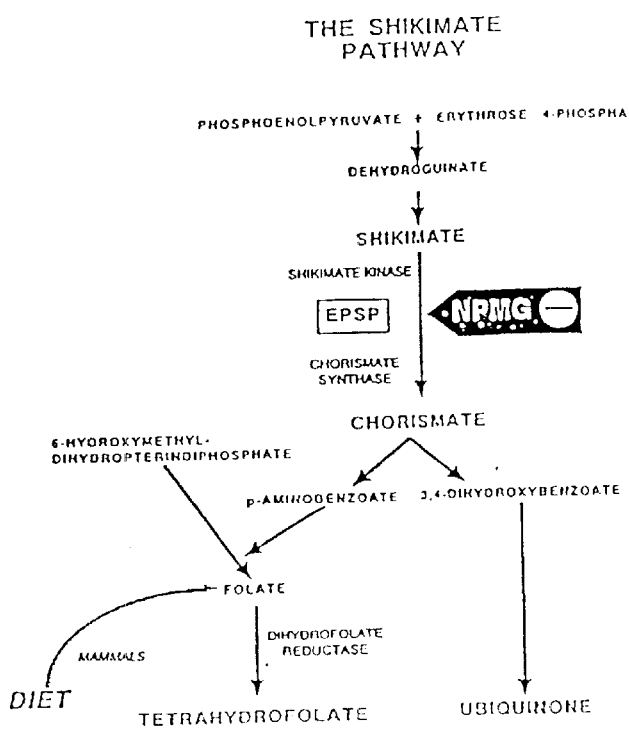

The shikimate pathway is common to plants, fungi and certain other microorganisms and Apicomplexan parasites, but it is not present in mammalian cells. FIG. 4A details the events that result in the production of tetrahydrofolate, aromatic amino acids and ubiquinone in plants, algae, bacteria and fungi. In this pathway, chorismate is formed through the sequential action of a number of enzymes including EPSP-synthase and chorismate synthase. EPSP-synthase is inhibited by NPMG. Chorismate is further processed to yield tetrahydrofolate or ubiquinone by a further series of enzymatic reactions. This pathway has not been described in mammals which are dependent on diet for folate and therefore for tetrahydrofolate production. This pathway is required for the synthesis of certain aromatic amino acids and aromatic precursors of folic acid and ubiquinone. It is likely that Toxoplasma gondii utilizes the shikimate pathway for synthesis of folic acid, ubiquinone and aromatic amino acids.

N-(phosphonomethyl) glycine, an inhibitor of 3-phospho-5-enolpyruvylshikimate (EPSP) synthase and thus an inhibitor of shikimate to chorismate conversion, affects the pathway (Table 1). The ability of this compound to inhibit the growth of T. gondii was examined by the assay described in Example 1. FIG. 4B demonstrates the ability of NPMG (a specific inhibitor of EPSP-synthase) to restrict the growth of T. gondii in an in vitro assay over a 4 day period. T. gondii growth is measured by their ability to incorporate tritiated uracil and is expressed as counts/minute (CPM) on the Y-axis. The X-axis describes how the T. gondii cultures were treated. Cultures that were grown in medium (medium) produced a CPM of around 72,000. If no T. gondii were added to the cultures (no RH), a CPM of around 2,000 was observed. Pyrimethamine (0.1 $\mu$g/ml) and sulphadiazine (12.5 $\mu$g/ml) added to cultures resulted in a marked reduction in CPM compared with untreated cultures. At a dose of 3.12 mM NMPG (3.12) restricted around 60% of CPM and at a dose of 4.5 mM it inhibited parasite growth by around 80%, with counts of about 12,000 CPM.

Figure 4C:
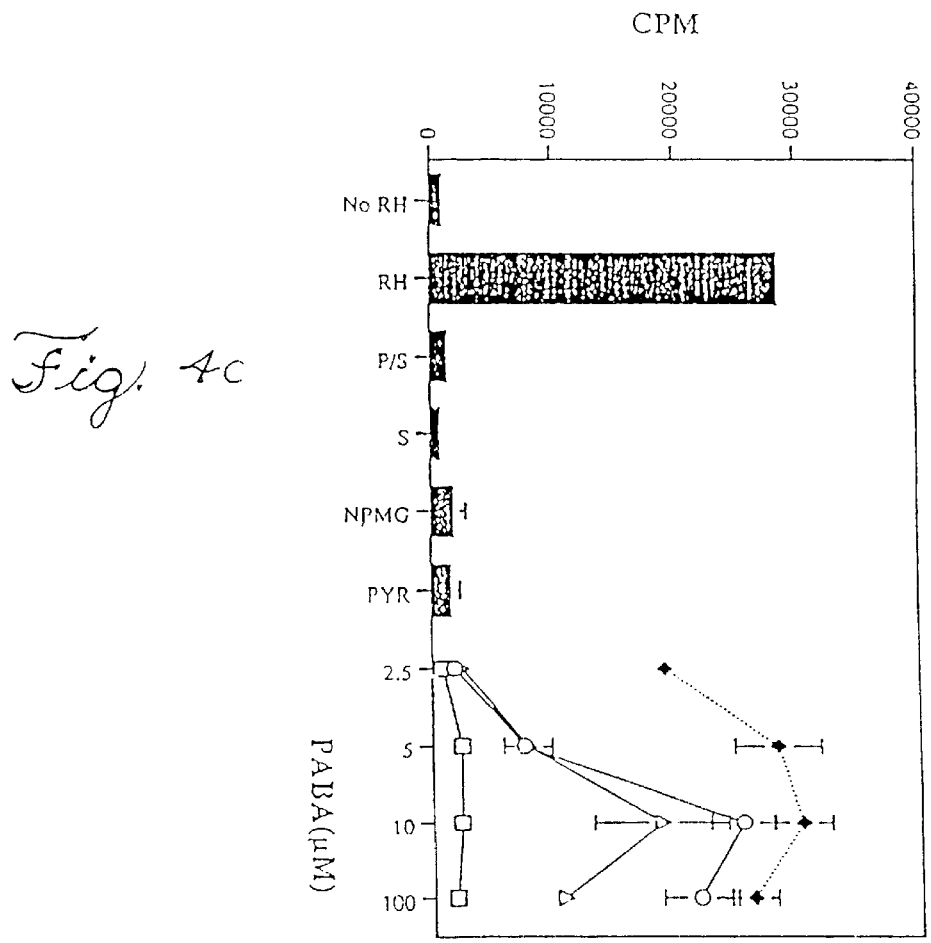
Figure 4B:
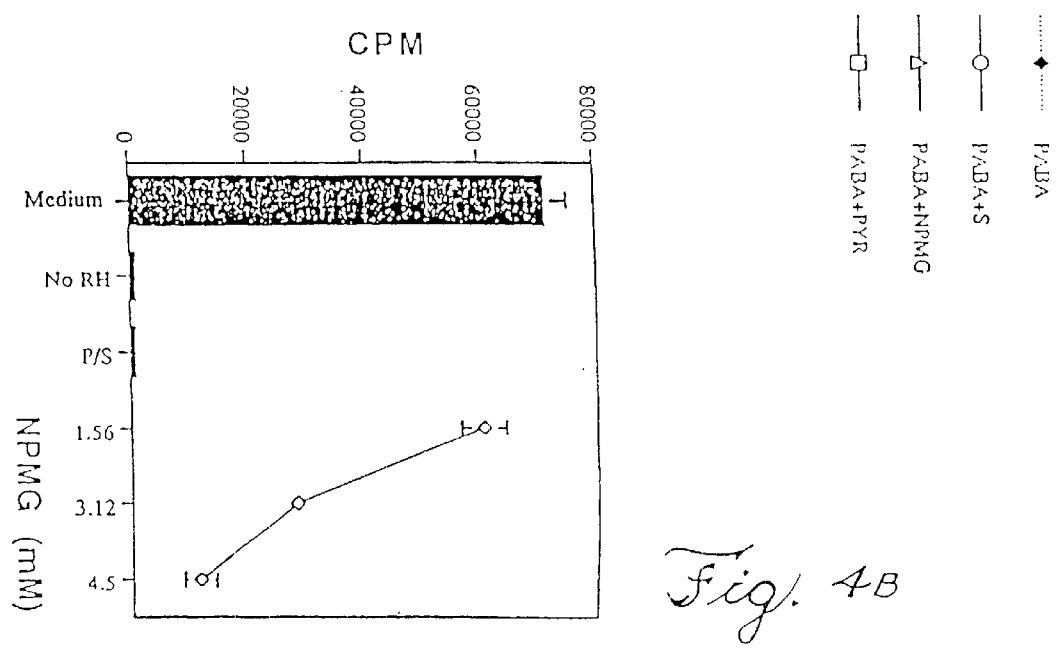
Figure 4D:
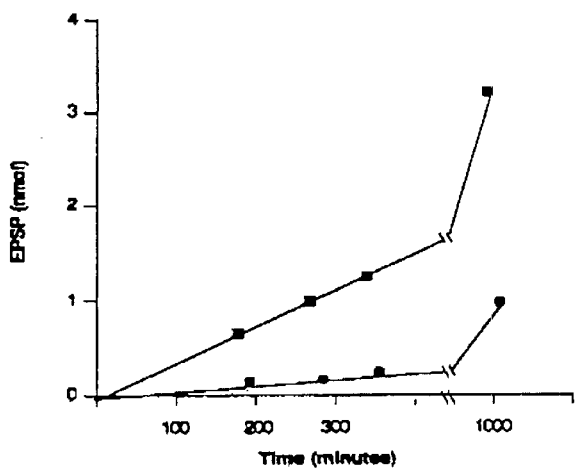
Figure 4E:
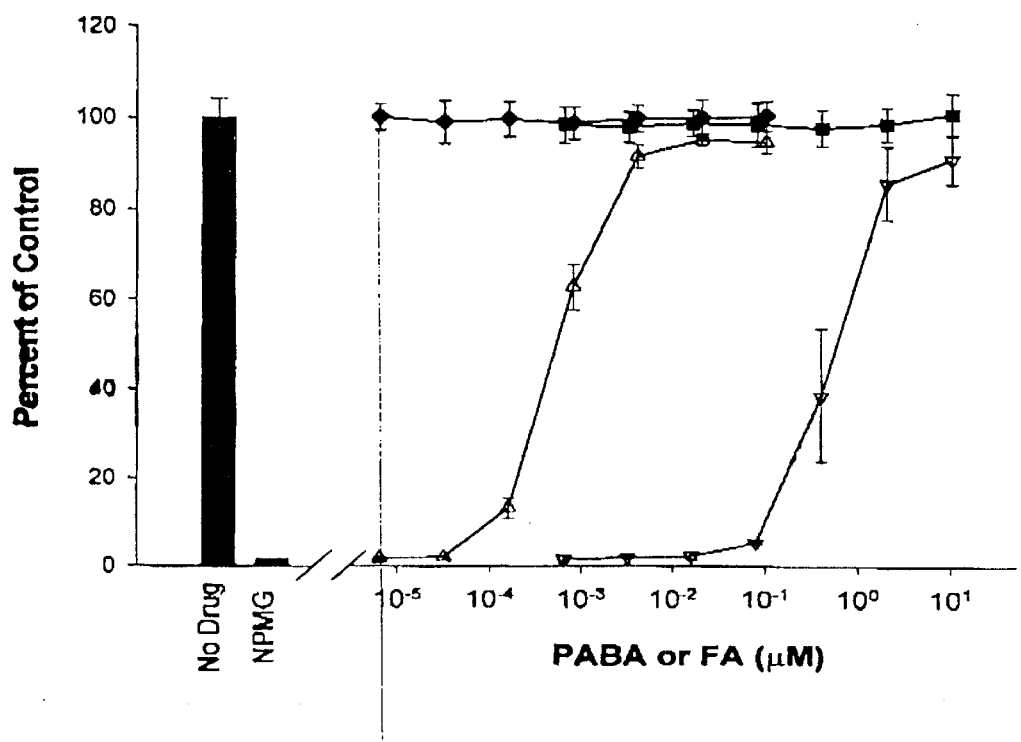

In FIG. 4C the ordinate shows uptake of tritiated uracil into T. gondii nucleic acids; inhibitory effects of NPMG on nucleic acid synthesis is shown; where PABA at increasing concentrations is added to such cultures, PABA abrogates the inhibitory effects of NPMG on EPSP synthase restoring nucleic acid synthesis.

vi. Branched Chain Amino Acid Synthesis

Imidazolinones and sulfonylureas inhibit acetohydroxy acid synthase in Apicomplexan parasites.

vii. Starch (amylopectin) Synthesis and Degradation

UDP glucose starch glycosyl transferase is inhibited by substrate competition in Apicomplexan parasites.

viii. Transit Sequences

Antisense, ribozymes, catalytic antibodies, (Pace et al., 1992; Cate et al., 1996; Charbonnier 1997; Askari et al., 1996) conjugation with toxic compounds allow targeting of parasite molecules using transit sequences.

Identification of transit sequences in Apicomplexans provides many means for disruption of metabolic pathways. Antisense or ribozymes prevent the production of the transit peptide and associated protein. Alternatively production of transit peptide sequences, and the conjugation to toxic molecules, allow disruption of organellar function. Catalytic antibodies also are designed to destroy the transit sequence. These antisense compounds or ribozymes or toxic molecules targeted to transit sequences with intracellular antibodies are used as medicines to inhibit the parasite.

Example 4

Plant-like Pathways and Enzymes in Apicomplexan Parasites Plasmodium falciparum and Cryptosporidia parvum Based on the effects of inhibitors of plant-like pathways, abrogation of inhibitor effects, and detection of specific enzymes and/or genes, Apicomplexans, in general, have plant-like pathways. Results shown in this example broaden the observations of the presence of plant-like pathways in Apicomplexans beyond the representative parasite T. gondii.

i. Heme Synthesis

Figure 6:
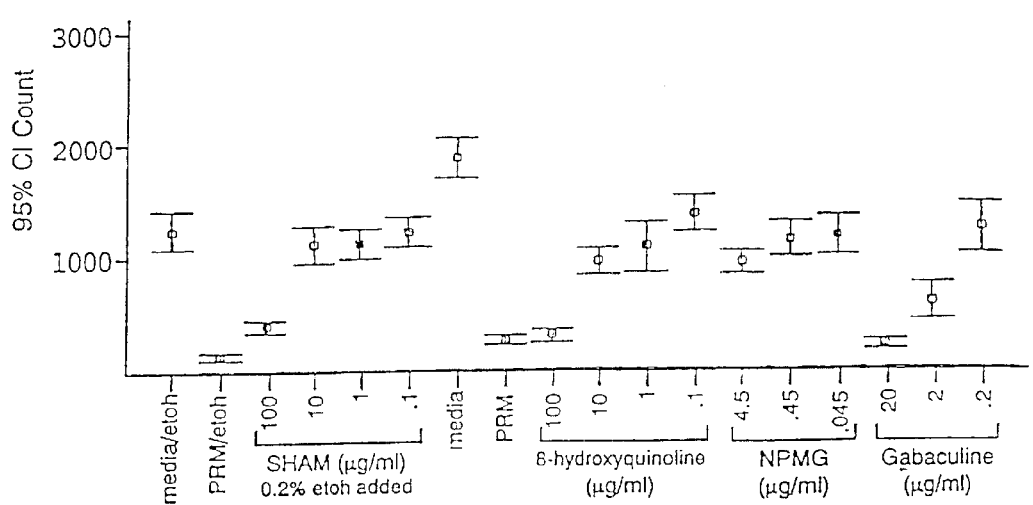
FIG. 6 shows inhibitory effects of NPMG, gabaculine, SHAM 8-OH-quinoline and on Cryptosporidia. 3NPA also inhibited Cryptosporidia.

Gabaculine inhibited the heme synthesis pathway (GSAT) in Apicomplexan parasites (FIGS. 1B and 1C, T. gondii; FIG. 6, Cryptosporidia) but with modest or no affect on P. falciparum (Table 3, Malaria).

FIG. 6 demonstrates the effect of NPMG, gabaculine, SHAM and 8-hydroxyquinoline and 3-NPA on Cryptosporidia in vitro. C. parvum oocysts at 50,000/well were incubated at 37° C. (8% $CO_2$) on confluent MDBKF5D2 cell monolayers in 96 well microtiter plates with the following concentrations of each drug. The concentrations used were: SHAM (0.2% ETOH was added) 100, 10, 1, 0.1 $\mu$g/ml; 8-hydroxyquinoline 100, 10, 1, 0.1 $\mu$g/ml; NPMG 4.5, 0.45, 0.045 $\mu$g/ml; gabaculine 20, 2, 0.2 $\mu$g/ml. The level of infection of each well was determined and analyzed by an immunofluorescence assay at 48 hours using an antibody to C. parvum sporozoites made in rabbits at a concentration of 0 1%. Fluorescein-conjugated goat anti-rabbit antibody was used at a concentration of 1%. 95% Cl count was the mean parasite count per field when 16 fields counted at 10×magnification ±s.d. of the mean. The approximate 95% Cl counts were as follows: media and ethanol~1200; paromomycin (PRM) and ethanol~100; SHAM 100 $\mu$g/ml~400; SHAM 10 $\mu$g/ml~1100; SHAM 1 $\mu$g/ml~1100; SHAM 0.1 $\mu$g/ml~1200; media alone~1800 $\mu$g/ml; PRM~200; 8-OH-quinoline 100 $\mu$g/ml;~300; 8-OH-quinoline 10 $\mu$g/ml;~900; 8-OH-quinoline 1 $\mu$g/ml~1100; 8-OH-quinoline 0.1 $\mu$g/ml~1300; NPMG 4.5 $\mu$g/ml~900; NPMG 0.45

μg/ml~1200; NPMG 0.045~1200; gabaculine 20 μg/ml~200; gabaculine 2 μg/ml~600; and gabaculine 0.2 μg/ml~1300. Thus each of these compounds are promising lead compounds as antimicrobial agents effective against Cryptosporidia.

ii. Glyoxylate Cycle

3-NPA inhibited the glyoxylate cycle (isocitrate lyase) and/or succinate dehydrogenase in Apicomplexan parasites (FIG. 2B, *T. gondii*) and also inhibited *P. falciparum* and *C. parvum*.

To determine whether there is an Apicomplexan glyoxylate cycle, to analyze the sensitivity of *T. gondii* tachyzoites and bradyzoites to glyoxylate cycle inhibitors and to determine whether Apicomplexan parasites have isocitrate lyase which presents a unique pathway for lipid metabolism that can be targeted with inhibitors, the following methods are suitable.

The inhibitor of isocitrate lyase is 3-nitropropionic acid (concentration ranging from 0.005 to 5 mg/ml in vitro, and 5 to 50 mg/kg/day in vivo). Mutants [Yale Stock Center] used for complementation are as follows: *E. coli* strains; DV 21A01 (aceA which lacks isocitrate lyase) and DV21 A05 (aceB which lacks malate synthase). Plant gene sequences suitable for comparison are those described by Kahn et al (1977), Maloy et al. (1980); and Maloy et al. (1 982). A biochemical assay for isocitrate lyase activity is the method of Kahn et al. (1977). The polyclonal antibodies to cotton malate synthase and cotton isocitrate lyase which hybridize to *T. gondii* proteins of approximately 60 kd are used to identify these enzymes in other Apicomplexan parasites.

iii. Alternative Oxidase

SHAM and 8-hydroxyquinoline inhibited the alternative pathway of respiration, i.e., the alternative oxidase in Apicomplexan parasites [FIG. 3, *T. gondii*; FIG. 6, *Cryptosporidia parvum*; Table 3, *Plasmodium falciparum* (clones W2, D6), pyrimethamine resistant or sensitive clones. Because Cryptosporidia appear to lack mitochondria, the plastid is a likely site for the alternative pathway of respiration.

TABLE 3

Effect of NPMG, SHAM, 8-OH quinoline, 3NPA and gabaculine on the D6 and W2 clones of *Plasmodium falciparum**

| Inhibitor | Parasite Clone | Conc (ng/ml) | |
|---|---|---|---|
| | | IC 50 | IC 90 |
| NPMG | D6 | 823 | 2510 |
| | W2 | 1716 | 3396 |
| SHAM | D6 | 6210 | 25066 |
| | W2 | 5705 | 42758 |
| 8-OH-quinoline | D6 | 1204 | 1883 |
| | W2 | 1631 | 4521 |

*Assays were performed in accordance with Milhous et al., 1985; Odula et al., 1988. Concentrations (ng/ml) of other compounds that inhibited these clones in this assay were as follows for the W2 and D6 clones: Pyrimethamine (82.10, 0.05), Chloroquin (40.86, 2.88), Quinine (38.65, 4.41), HAL (0.33, 0.51), Atovaquovone (0.13, 0.12). 3NPA also inhibited *P. falciparum* with IC 50 = 3304, 2817; IC 90 = 4606, 2817 but with a very small or no significant effect of gabaculine (IC 50 ≧ 45,000).

Effect of SHAM on wild type malaria in vitro had been described earlier (Fry and Beesley, 1991). However, this observation was presented without knowledge that SHAM affected alternative oxidase function.

iv. Shikimate/Chorismate

NPMG inhibited the shikimate pathway in Apicomplexan parasites (FIG. 4B, *T. gondii*; Table 4; Malaria; FIG. 6, Cryptosporidia).

Presence of a product of the enzymatic reaction in the pathways of the present invention abrogates the effect of the inhibitor on a specific enzyme because the product no longer has to be made by enzyme catalysis of a substrate. Thus, addition of the product proves the specificity of the effect of the inhibitor on the enzyme. The addition of PABA abrogates the exogenous effect of NPMG which is an inhibitor of EPSP synthase (FIG. 4B, *T. gondii*). Because PABA ablates the effect of the inhibitor NPMG on EPSP synthase, the presence of the shikimate pathway in Apicomplexan parasites is demonstrated.

Other specific methods to determine whether Apicomplexan parasites have a metabolically active EPSP synthase enzyme involved in conversion of shikimate to chorismate and further characterize this metabolic pathway in *T. gondii* are as follows:

Use of the inhibitor N-(phosphonomethyl) glycine (concentrations of 3.125 mM in vitro and 100 mg/kg/day in vivo). The product rescue assays are performed with PABA. The mutants for complementation are as follows: *E. coli*, AroA; *E. coli*, AroC; and yeast, AR. [Yale Stock Center] Plant gene sequences for comparison are outlined by Klee et al. (1987). A biochemical assay for EPSP synthase activity in cellular lysates is as described by Mousdale and Coggins (1985). Other enzymes in this pathway also are characterized (Nichols and Green, 1992). The full length nucleotide sequence of chorismate synthase was obtained following restriction digestion and primer-based sequencing of the Tg EST zyllc05.r1 clone obtained from the "Toxoplasma EST Project at Washington University" and of *P. falciparum* EST czap PFD d2.1 clone obtained from the "malaria EST project," D Chakrabarti, Florida. The *Toxoplasma gondii* sequence has substantial homology with tomato and several other chorismate synthases and a region of the *T. gondii* protein has 30% identity and 45% homology with the transit sequence of *Zea mays* (sweet corn). Other inhibitors of EPSP synthase are Inhibitors 4 and 5, sulfosate (Marzabadi et al., 1996). Other inhibitors of enzymes in this pathway also have been developed by others and provide a paradigm for the rational synthesis of competitive substrate inhibitors of Apicomplexan parasites.

V. Branched Chain Amino Acid and Other Essential Amino Acid Synthesis

Acetohydroxy acid synthase is an enzyme present in plants but not animals and is inhibited by imindazolinones and sulfonylureas in Apicomplexan parasites. Inhibitors of histidine synthesis restrict growth of Apicomplexan parasites.

VI. Starch (Amylose/Amylopectin) Synthesis and Degradation

UDP glucose starch glycosyl transferase, starch synthetase and Q (branching) enzymes are inhibited by substrate competitors in Apicomplexan parasites.

VII. Lipid Synthesis

The plant-like acetyl coA decarboxylase is inhibited by a number of inhibitors shown in Table 1B. Linoleic acid and linoleneic acid synthases are inhibited by newly designed competitive substrates.

VIII. Auxins and Giberellins

The known auxin mimics and Giberellin synthesis and Giberellin inhibitors inhibit Apicomplexan parasites' growth.

IX. Glutamine/Glutamate Synthesis

Glufosinate inhibits Apicomplexan glutamine/glutamate synthesis because the critical enzyme is plant-like.

X. Transit Sequence

The transit sequence is conjugated with toxic molecules such as ricins and used to disrupt plastid function in Apicomplexans. Other strategies, such as antisense, ribozymes or the use of catalytic antibodies prevent translation of DNA to protein or catalyze the destruction of mature protein. This interferes with functioning of the molecule and thus the parasite's growth and survival.

Example 5

The Combined Effects of Inhibitors of Apicomplexan Parasites

Figure 5:
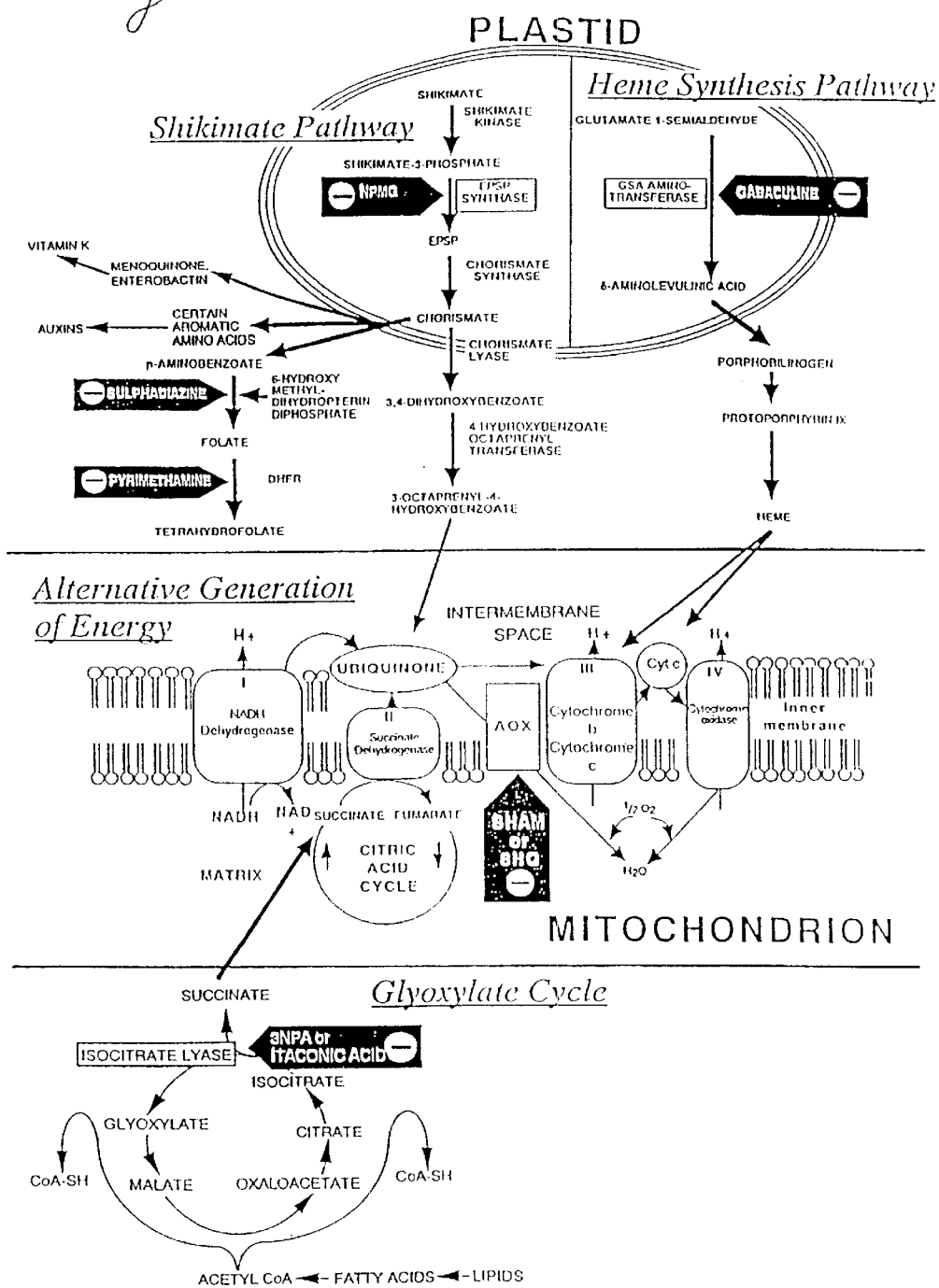
FIG. 5 is a schematic representation of interrelationships of metabolic pathways in Apicomplexan parasites.

The effect of enzymes in pathways "in parallel" are additive and in "series" are more than the additive effect of either inhibitor used alone (i.e., synergistic). FIG. 5 demonstrates the inter-relationship of the shikimate pathway and heme synthesis with the electron transport chain. The shikimate pathway produces 3,4-dihydroxybenzoate which is converted to ubiquinone, an essential component of the electron transport chain. Thus, NPMG, an inhibitor of EPSP-synthase, indirectly affects ubiquinone production and, thus, the electron transport chain. Similarly, heme is required for the production of cytochromes in the electron transport chain. Thus, inhibition of heme production by gabaculine also indirectly affects the conventional electron transport chain. This scheme allows synergistic combinations of drugs. Thus, NPMG and sulphadiazine (a competitive PABA analogue) which act at different points of the folate synthesis pathway are predicted to be synergistic, whereas the effects of gabaculine and sulphadizine (a competitive PABA analogue) which act on different pathways, are predicted to be additive. Similarly, gabaculine and SHAM are a predicted synergistic combination of inhibitors. Table 4 demonstrates the additive inhibitory effect of sulphadiazine and gabaculine on the growth of T. gondii over 4 days in culture. T. gondii growth is measured by their ability to incorporate tritiated uracil and is expressed as counts/minute (CPM). Cultures that were grown in medium (medium) produced a CPM of about 36,000. If no T. gondii were added to the cultures (no RH), a CPM of about 2,000 was observed. Pyrimethamine (0.1 µg/ml) and sulphadiazine (12.5 µg/ml) added to cultures resulted in a marked reduction in CPM compared with untreated cultures. The growth of T. gondii was inhibited by about 60% in cultures treated with 5 mM gabaculine (gabaculine). The growth of T. gondii in cultures treated with sulphadiazine (1.56 µg/ml) was reduced by approximately 60%. When this dose of sulphadiazine was used in combination with 5 mM gabaculine, as expected, the combined effect of gabaculine plus sulfadiazine is additive because the pathways are in parallel. In contrast, NPMG and sulfadiazine combine in a synergistic manner. Because heme is needed for conventional mitochondrial respiration, it is expected that if both the heme synthesis and alternative oxidase pathways are present, then 3-amino-2,3-dihydrobenzoic acid and SHAM will demonstrate synergy. Similarly, ubiquinone or end products of the shikimate pathway are needed for mitochondrial respiration and NPMG plus SHAM therefore demonstrate synergy. Table 4 also shows that, the effects of gabaculine and SHAM are not synergistic as would be predicted by this simple model. The likely reason for this is that ALA synthase is present in T. gondii and provides a default pathway for the synthesis of δ-aminolevulinic acid. Thus, the effects of gabaculine plus SHAM are not synergistic. Cycloguanil which affects the plant-like DHFR-TS of T. gondii (McAuley et al, 1994) also is synergistic with NPMG and other inhibitors of enzymes in the shikimate pathway which provides an improved, novel method to treat this infection. Use of synergistic combinations provide an improved strategy for the development of new medicines for the treatment of disease and eradication of the parasite.

TABLE 4

Representative Effects on Inhibitors Alone and Together on Replication of T. gondii which demonstrate

| Drug A | Drug B | CPM untreated | CPM for A | CPM for B | CPM for A + B Actual | Predicted | Ratio Actual:Predicted* |
|---|---|---|---|---|---|---|---|
| NPMG | Sulfadiazine | 71449 ± 3763 | 28138 ± 2216 | 25026 ± 4365 | 2368 ± 418 | 9856 | 0.24 |
| NPMG | Pyrimethamine | 64343 ± 1222 | 25097 ± 1398 | 69217 ± 3253 | 9354 ± 2126 | 25097 | 0.37 |
| NPMG | SHAM | 64343 ± 1222 | 25097 ± 1398 | 42993 ± 1098 | 7554 ± 970 | 16769 | 0.45 |

Predicted CPM for Drug A + Drug B (if effect is only additive, not synergistic) is calculated as (CPM Drug A × CPM Drug B)/CPM of untreated culture. Concentrations were: NPMG (3.25 mM); Sulfadiazine (6.25 µg/ml); Pyrimethamine (0.025 µg/ml); SHAM (0.78 µ190 g/ml).
*A ratio of Actual:Predicted of <1 is considered synergistic. A ratio of Actual:Predicted ≥ 1 is considered additive.

Example 6

Effects of Inhibitors In Vivo

Candidate inhibitors are administered to animals by daily intraperitoneal injection or by addition to the drinking water. To inhibit EPSP synthase, in vivo, NPMG is administered at a dose of 100 mg/kg/day.

a) Survival:

Five hundred tachyzoites of the RH strain are administered intraperitoneally to BALB/c mice. Cumulative mortality is followed in groups of mice given inhibitor compared to untreated controls.

b) Formation of Cysts:

C3H/HeJ mice that have been infected perorally with the Me49 strain of T. gondii for 30 days are treated with the inhibitor for 30 days. Cyst burden and pathology in the brains of inhibitor-treated and control mice are compared using methods described previously (Roberts, Cruickshank and Alexander, 1995; Brown et al., 1995; McLeod, Cohen, Estes, 1984; McLeod et al., 1988). Cyst numbers present in a suspension of brain are enumerated, or cyst numbers in formalin fixed paraffin embedded sections are quantitated.

c) Persistence of Cysts:

C3H/HeJ mice are infected orally with 100 cysts of T. gondii (Me49 strain). Inhibitors are administered to groups of mice from day 30 post infection to day 50 post infection. Cyst burden, mortality and pathology are compared in treated and control mice on days 30 and 50 post infection and in mice that receive antibody to gamma interferon which leads to recrudescence of disease.

d) Synergy:

If marked synergistic effect is demonstrated in vitro by showing that the subinhibitory concentrations used together exert an effect greater than the additive effects of each used separately, for any combinations, their effect alone and together in vivo is compared.

e). New Assays which Determine the Effects of Antimicrobial Agents on *T. gondii* In Vivo Previously reported assay systems measure protection against death following intraperitoneal infection if an animal is infected with the virulent RH strain of *T. gondii*. Novel aspects of the assay systems in the present invention are using the Me49 (AIDS repository) strain of *T. gondii* to determine the effect on brain cyst number following acute peroral infection by an Apicomplexan parasite, the effect on the established number of brain cysts during subacute/chronic infection, and use of the Me49 and RH strains to demonstrate synergy of inhibitors of plant-like pathways of the present invention which are "in series," and a novel system to demonstrate reduction of parasitemia which is quantitated using a competitive PCR technique. In this competitive PCR method the *T. gondii* B 1 gene is amplified by PCR in the presence of a construct which produces a product slightly smaller than the wild type B 1 gene. The amount of construct can be quantitated to semiquantitate the amount of the competing wild type gene. For example, presence of a greater amount of the wild type gene will result in lesser use of the competitor.

f). Effect of Antimicrobial Agents on Apicomplexan Parasites In Vivo

A demonstration of the effect of inhibitors of plant-like metabolic pathways in vivo is the synergistic effect of NPMG and low dosage pyrimethamine. NPMG is an inhibitor of infection and promotes survival of mice infected with the virulent RH strain of *T. gondii* when utilized in conjunction with a low dose of pyrimethamine, whereas neither low dosage pyrimethamine nor NPMG alone are protective. Sulfadiazine reduced manifestations of infection in vivo. SHAM affects parasitemia and number of brain cysts.

FIG. 8 demonstrates the ability of NPMG and pyrimethamine administered in combination to protect mice from an otherwise lethal challenge with the virulent RH strain of *T. gondii*. Mice were infected intraperitoneally with 500 tachyzoites and left untreated (control) or treated by the addition of pyrimethamine (PYR), NPMG (NPMG) or both pyrimethamine and NPMG (PYRlNPMG) to their drinking water. Percent survival is marked on the Y-axis and days post infection on the X-axis. Untreated mice and those treated with either pyrimethamine or NPMG died between day 7 and 9 post infection. In contrast 66 percent of mice treated with pyrimethamine and NPMG survived until day 9 post infection and 33 percent survived until the conclusion of the treatment (day 30 post infection). After the withdrawal of treatment, all of these mice survived until the conclusion of the experiment (day 60 post infection).

Example 7

Presence of an Enzyme in a Specific Life Cycle Stage Predicts Efficacy of Inhibitors of the Enzyme on this Stage of the Parasite The effect of candidate inhibitors on different life cycle stages and their effect on stage conversion is of considerable interest and clinical importance. The bradyzoite form of *T. gondii* was studied by electron microscopy and was found to have a plastid. Intraparasite immunolocalization of the enzymes is also performed. Gabaculine treated cultures are stained with antibodies to tachyzoites and bradyzoites. Tachyzoites of the RH strain are grown in the peritoneum of ND4 mice for 3 days. Tachyzoites are harvested in saline (0.9%) from the peritoneal cavity of euthanized mice and purified by filtration through a 3 $\mu$m filter. Bradyzoites are isolated as described herein in the Material and Methods. The tachyzoites are pelleted by centrifugation and the pellet is fixed in 2.5% glutaraldehyde. Cysts and bradyzoites are purified from the brains of C57BL10/ScSn mice as described herein in the Materials and Methods and then fixed in 2.5% glutaraldehyde.

Immunoelectronmicroscopy is as described by Sibley and Krahenbuhl (1988) using gold particles of different sizes with antibodies to the enzymes to identify the enzyme localization in different organelles which are identified morphologically. Immunoelectronmicroscopy localization is accomplished with Amersham Immunogold kit and cryosectioning using standard techniques in the electronmicroscopy facility at the University of Chicago or at Oxford University, Oxford, England. Extracellular organisms are studied as well as tachyzoites and bradyzoites at intervals after invasion. Morphology of the parasites, their ultrastructure and the localization of the intracellular gold particles conjugated to the antibodies is characterized. Invasion is synchronized by placing tachyzoites and bradyzoites with P815 cells at 4° C., then placing cultures at 37° C. Intervals to be studied are before 1, 5, and 10 minutes and 4 hours after invasion.

Immunostaining and immunoelectronmicroscopy using an antibody to soybean, or synechococcus, or barley GSAT indicate whether the enzyme is present or absent in both the tachyzoite and bradyzoite life cycle stages and localizes the enzyme in the parasite.

a) Immunostaining for tachyzoites and bradyzoites

Immunostaining of tachyzoites and bradyzoites is evaluated with fluorescent microscopy. This is performed on cultures of fibroblasts in Labtech slides infected with tachyzoites (RH strain) or bradyzoites and permeabilized using triton, or saponin or methanol, as described by Weiss et al., 1992; Dubremete and Soete, 1996; Bohne et al. (1996). Slides are stained 1, 2, 4, 6, and 8 days post infection with anti-BAG (Weiss et al., 1992) and anti-SAG1 (Mineo et al., 1993; McLeod et al., 199 1; Roberts and McLeod, 1996).

b) Antibodies

Antibodies to the bradyzoite antigens (Weiss et al., 1992; and Bohne et al., 1993) and monoclonal and polyclonal antibodies to SAG1 (Kasper et al. 1983) as a marker for tachyzoite stage specific antigens are used for immunostaining of parasites to establish stage of the parasite. Transgenic parasites with bradyzoite genes with reporter genes are also useful for such studies.

c) Inhibitors and Stage Switching

The effect of inhibitors of conventional (KCN, Rotenone, Antimycin A or Myxothiazol) respiration and alternative respiration on inhibition of growth of tachyzoites and bradyzoites are compared using standard inhibition experiments in conjunction with immunostaining techniques. Tachyzoites use conventional and alternative pathways of respiration whereas the bradyzoite stage relies on alternative respiration. Inhibitors of conventional respiration favor tachyzoite to bradyzoite switching whereas inhibitors of alternative respiration inhibit tachyzoite and bradyzoite stages.

d) Synergy Studies, Gabaculine Treatment

Synergy studies with gabaculine are of particular interest because heme is used in the conventional oxidase pathway.

If there is synergy, iron influences stage switching. For alternative oxidase, immunostaining for bradyzoites and tachyzoite antigens is performed using gabaculine treated and control cultures. This is especially informative concerning whether bradyzoites utilize alternative oxidases exclusively, because gabaculine treatment of cultures would limit use of conventional oxidases and thereby select bradyzoites.

e) Western Blot Analysis, and ELISAs to Determine Stage Specific Expression of Enzymes Bradyzoites and tachyzoites also are compared directly for the relative amounts of alternative oxidase, using northern blot analyses, enzyme assays of parasites, isolation of mRNA and RT-PCR, using a competitor construct as an internal standard, and by Western blotting and ELISAs using antibodies to the enzymes (e.g., alternative oxidase). UDP-glucose-starch glycosyl transferase, chorismate synthase, isocitrate lyase, GSAT also are studied in a similar manner.

Example 8

Probing Apicomplexan DNA with Homologous Plant-like Genes or Potentially Homologous Genes from Other Parasites The presence of the gsa genes, alternative oxidase genes, EPSP synthase genes, chorismate synthase genes, isocitrate lyase genes, and malate synthase genes are identified by probing, and then sequenced. For example, the cDNA clone of soybean gsa is labeled for chemiluminescent detection (ECL) or $^{32}$P detection to identify homologous gsa sequences in *T. gondii*. Probes are used on a membrane containing the genomic DNA of *T. gondii* and soybean (positive control). When *T. gondii* genes are isolated, they are used to probe other Apicomplexan DNA. Thus, the gsa genes of Cryptosporidia, Eimeria, and Malaria are detected in the same manner as the *T. gondii* gsa.

In addition, DNA probes complementary to Trypanosome alternative oxidase DNA are used to probe the Apicomplexan DNA. The gene for *T. gondii* alternative oxidase is identified by screening *T. gondii* cDNA expression libraries using the 7D3 monoclonal antibody or the tobacco alternative oxidase gene used as a probe and thus detecting the gene expressing the relevant protein. This gene is used to detect the alternative oxidase genes of other Apicomplexan parasites by Southern analysis and screening other Apicomplexan cDNA libraries.

A nucleotide sequence generated from random sequencing of a *T. gondii* tachyzoite cDNA library and placed in the Genbank database was found to encode a protein with homology to tomato chorismate synthase. The EST was obtained, cloned and the full length sequence of the *T. gondii* chorismate synthase gene and deduced amino acid sequences were obtained (FIGS. 9 and 10). This provides evidence for these plant-like pathways and information useful in preparing a probe to isolate and sequence this full gene from other Apicomplexan parasites as well. This gene was used as a probe and identified a chorismate synthase in *Eimeria bovis* DNA and *Cryptosporidium parvum* DNA. A *P. falciparum* EST has also been cloned and sequenced. Probes for gsa (soybean) alternative oxidase (soybean and tobacco), isocitrate lyase (cotton), UDP glucose starch glycosyl transferase (sweet corn), and acetohydroxy acid synthase (sweet corn) also are used to screen for clone, and sequence Apicomplexan genes. Large numbers of *T. gondii* genes from tachyzoite and bradyzoite cDNA libraries are being sequenced and deposited in Genbank. Putative homologous genes encoding plant enzymes are used to compare with these sequences to determine whether they are identified in the libraries and if so to determine whether the enzymes are encoded in the nucleus or plastid.

Example 9

Identification of Genes Encoding Enzymes of the Plant-Like Biochemical Pathways in Apicomplexan Genes are isolated from a cDNA library by hybridization using specific probes to genes known to encode enzymes in metabolic pathways of plants. (see Example 9). Genes are cloned by complementation from a *T. gondii* cDNA expression library using a series of *E. coli* mutants that lack these enzymes and thus depend on the addition of exogenous additives for their optimal growth. Transformed bacteria are used to isolate and sequence plasmid DNA and from those sequences, probes are generated to determine whether other Apicomplexans have genes homologous to those in *T. gondii*.

1) cDNA libraries:

A cDNA library was constructed by Stratagene from mRNA isolated from *T. gondii* tachyzoites of the Me49 strain of *T. gondii* using the Uni-ZAP XR cDNA library system. The titer of the amplified library is 1–2×10$^{10}$/ml. Other cDNA libraries also are utilized.

The phagemids were excised with R408 or VCS-M13 helper phage and transduced into XL1-Blue Cells. The plasmid DNA was purified using the Qiagen maxiprep system. Other libraries, e.g., early Me49 bradyzoite, in vivo Me49 bradyzoite, and Me49 tachyzoite libraries also are suitable, as are other tachyzoite and bradyzoite libraries prepared by Stratagene.

2) Screening of library for genes.

This is done in a standard manner using monoclonal or polyclonal antibodies or a radiolabeled gene probe.

3) cDNA expression libraries are probed with DNA from the genomes of:

a) *Toxoplasma gondii;* b) *Plasmodium malariae;* c) *Cryptosporidium parvum;* d) Eimeria.

The existence of plant-like pathways is confirmed in members of the Apicomplexa by demonstrating the existence of genes encoding the enzymes required for the pathways. Genomic DNA is examined by Southern blot analysis for the presence of the sequences encoding enzymes required for specific algal or plant metabolic pathways. Genomic DNA is extracted from Apicomplexan parasites by proteinase K digestion and phenol extraction. DNA(5–10 μg) is digested with restriction enzymes, electrophoresed through 1% Agarose and transferred to a nylon membrane. The ECL (Amersham) random prime system is used for labeling of DNA probes, hybridization and chemiluminescence detection. Alternatively, the Boehringer Mannheim Random Prime DNA labeling kit is used to label the DNA with $^{32}$P with unincorporated nucleotides removed using G-50 Sephadex Spin columns. Hybridization with the $^{32}$P-labeled probe is carried out in [1M NaCl, 20 mM NaH$_2$ PO4 pH 7.0, 1% SDS, 40% formamide, 10% dextran sulfate, 5 mg/ml dry milk, 100 μg/ml salmon sperm DNA] at 37° C. Washes are optimized for maximum signal and minimum background. Probes are prepared from *T. gondii* cDNA clones obtained and characterized as described in Example 9. If lack of overall sequence conservation limits ability to detect homology, highly conserved regions are useful. For example, two highly conserved regions of the gsa gene are useful to generate oligonucleotide probes (Matters et al., 1995).

4) PCR:

An alternative approach for identifying genes encoding enzymes of the present invention is by using PCR with primers selected on the basis of homologies already demonstrated between plant protein sequences for the relevant gene. For example, for the gsa gene, polymerase chain reaction technology is used to amplify homologous sequences from a *T. gondii* cDNA library or *T. gondii* genomic DNA using primers generated from two highly conserved regions of GSAT. The *Neurospora crassa* alternative oxidase gene has been isolated using degenerate primers designed from conserved regions in alternative oxidase sequences from plant species (Li et al., 1996). These primers are used to detect and clone the alternative oxidase gene from *T. gondii*. Candidate PCR products are cloned using the Invitrogen TA cloning kit.

5) Sequencing:

DNA from candidate cDNA clones is extracted using the Promega Wizard Miniprep System. Clones of interest are purified in large scale using the Maxiprep Protocol (Qiagen) and are sequenced by modified Sanger method with an automated sequencer (ABI Automated Sequencer) by the University of Chicago Cancer Research Center DNA Sequencing Facility.

6) Homology Search: to determine whether there is homology of isolated genes with other genes, e.g. gsas, sequences are compared against those in Genbank using the BLASTN (DNA→DNA) and BLASTX (DNA→Protein) programs: *T. gondii* sequence data is available in Genbank. Sequences for plasmodia also are available as are some isolated sequences for the other Apicomplexan parasites. *T. gondii* sequences are searched for homologies to the known plant genes gsa, glutamyl-tRNA reductase, isocitrate lyase, malate synthase, alternative oxidase, EPSP synthase, and chorismate lyase using the BLASTN (DNA→DNA) and TBLASTN (Protein→Conceptual Translation of DNA Sequence) programs. The conserved plant gene sequences for the shikimate pathway are those described by Kahn et al. (1977) and Maloy et al. (1980; 1982). Conserved plant gene sequences for comparison of homologies are outlined by Klee et al. (1987). Similar libraries and sequence data for Plasmodia also are compared for homologies in the same manner.

7) Complementation:

To isolate *T. gondii* genes or to demonstrate that a gene encodes a functional enzyme product, plasmids from the cDNA library detailed above, or modified constructs, are used to complement *E. coli* mutant strains GE1376 or GE1377 (hemL) and RP523 (hemB) from the Yale *E. coli* genetic stock center and SASX41B (hemA) from D. Soll. This strategy has been successful for cloning gsa genes from plants and algae (Avissar and Beale, 1990; Elliott et al., 1990; Grimm, 1990; Sangwan and O'Brian, 1993). The hemA gene encodes glutamate-tRNA reductase, an enzyme important in the C5-pathway for heme synthesis. The hemB gene encodes ALA dehydratase, an enzyme common to both heme biosynthesis pathways that should be common to all organisms and is included as a positive control. Mutant bacteria are made competent to take up DNA with $CaCl_2$ treatment and are transformed with plasmids from the cDNA library. Briefly, chilled bacteria (O.D. 550 nm~0.4–0.5) are centrifuged to a pellet and resuspended in ice-cold 0.1M $CaCl_2$ and incubated for 30 minutes on ice. Following further centrifugation, the cells are resuspended in 0.1M $CaCl_2$, 15% glycerol and frozen at −80° C. in transformation-ready aliquots. 0.2 ml ice-thawed competent bacteria are incubated on ice for 30 minutes with approximately 50 ng plasmid DNA. Cells are placed at 43° C. for 2.5 minutes and cooled on ice for 2 minutes. Following the addition of 0.8 ml Luria Broth, cells are incubated at 37° C. for 1 hour and 0.1 ml is plated onto M9 minimal media plates. The M9 (Ausubel et al., 1987) medium contains 0.2% glycerol as the carbon source, 1 mM $MgSO_4$, 0.1 mM $CaCl_2$, 1 mM IPTG, 0.2 mg/ml Ampicillin, and 40 µg/ml threonine, leucine, and thiamine. Nonselective medium contains 25 µg/ml δ-aminolevulinic acid (hemL and hemA) or 4 µg/ml hemin (hemB). Alternatively, bacteria can take up DNA by electroporation. Chilled bacteria are prepared by a repetition of centrifugation and resuspension. The cells are washed in an equal volume of cold water, a ½ volume of cold water, a ⅕₀ volume of cold 10% glycerol, and finally in a 1/500 volume of cold 10% glycerol and frozen in 0.04 ml aliquots at −80° C. Cells are thawed at room temperature and chilled on ice. Cells are mixed with the DNA for 0.5–1 minutes and then pulsed at 25 µF and 2.5 KV. The cells are rapidly mixed with SOC medium and grown at 37° C. for 1 hour. Cells are plated in the same way as for $CaCl_2$ transformation.

Successful complementation of the *E. coli* mutants with a *T. gondii* gene is determined by plating the transformed bacteria onto minimal medium which lacks the supplement required for optimal growth of the *E. coli* mutant. Growth on the selective medium is compared to growth on nonselective medium, which contains 25:g/ml δ-aminolevulinic acid (hemL or hemA) or 4 µg/ml hemin (hemB). Clones that complement each *E. coli* mutant are tested for their ability to complement each of the other mutants. Clones of putative *T. gondii* gsa and glutamate-tRNA reductase should complement only hemL and hemA mutants, respectively. Clones that suppress more than one hem mutation are candidates for alternative oxidase gene clones.

A cDNA clone containing the entire soybean gsa gene was able to transform the *E. coli* hemL mutant from auxotrophic to prototrophic for δ-aminolevulinic acid (ALA). Thus the system for obtaining *T. gondii* genes that complement *E. coli* mutants is available.

For the glyoxylate cycle the mutants used for complementation are as follows: DV21 A01 (aceA which lacks isocitrate lyase) and DV21 A05 (aceB which lacks malate synthase).

For the shikimate pathway the mutants for complementation are available and used as follows: *E. coli,* AroA and yeast AR.

The same procedures are used for *Plasmodium falciparum* and *Plasmodium knowlesii,* Cryptosporidium and Eimeria complementation. When transit sequences lead to production of a protein which does not fold in such a manner that the protein can be expressed in *E. coli* or yeast constructs that lack these sequences are prepared to use for complementation that lack these sequences.

Example 10

Analysis of Alternative Oxidases in *T. gondii*

*T. gondii* bradyzoites use unique alternative oxidases. Alternative oxidases are necessary and sufficient for bradyzoite survival. Methods to characterize plant alternative oxidases are as described (Hill, 1976; Kumar and Söll, 1992; Lambers, 1994; Li et al., 1996, McIntosh, 1994).

For in vitro studies, cell lines that lack functional mitochondria are used. These cell lines are used to allow the study of inhibitors effective against the conventional or alternative respiratory pathways within the parasite, but independent from their effects on the host cell mitochondria. SHAM, an inhibitor of the alternative respiratory pathway is used at concentrations between 0.25 and 2 μg/ml in vitro, and 200 mg/kg/day orally or parenterally in vivo alone or in conjunction with other inhibitory compounds. Other approaches include complementation of alternative oxidase-deficient *E. coli* mutants to isolate and sequence the alternative oxidase gene, immunostaining using antibodies for potentially homologous enzymes, enzymatic assay and the creation of mutant-knockouts for the alternative oxidase gene and studying stage specific antigens in such knockouts.

1) Cell lines:

Two cell lines, a human fibroblast cell line (143B/206) lacking mitochondrial DNA, and the parental strain (143B) which possess functional mitochondria are used. These cell lines have been demonstrated to support the growth of *T. gondii* (Tomavo and Boothroyd, 1995).

2) Inhibitor studies:

Inhibitor studies are carried out as described herein. SHAM concentrations are 0.25 to 2 mg/ml in vitro and 200 mg/kg/day in vivo.

3) Immunostaining for tachyzoite and bradyzoites:

Immunostaining is performed on cultures of fibroblasts in Labtech slides infected with tachyzoites (RH strain) as described herein. Slides are stained 1, 2, 4, 6 and 8 days post infection with anti-BAG and antiSAG1.

4) RT-PCR is as performed using the protocol of Hill (Chaudhuri et al., 1996) with degenerate primers based on consensus sequences. The product is cloned, sequenced and homology with known alternative oxidases documents its presence.

5) Complementation and alternative oxidase gene cloning:

Complementation is used to demonstrate function and is an alternative approach to isolate the gene. Proper function of the complementation system is demonstrated by using complementation with a plant alternative oxidase gene. Mutants suitable for use are hemL, hemA, hemB. The alternative oxidase gene, AOX, is cloned from a *T. gondii* cDNA expression library by complementation of the *E. coli* hemL mutant. HemL mutants of *E. coli* cannot synthesize heme and are therefore deficient in respiration. This cloning strategy has been successful in isolating AOX genes from Arabidopsis (Kumar and Soll, 1992). The procedure employed for recovering transformants is identical to that used for cloning the *T. gondii* gsa gene. The distinction between the gsa and AOX genes is that the AOX gene should restore function not only to hemL mutants but also to other hem mutants of *E. coli*. In addition, respiratory growth of *E. coli* on the alternative oxidase should be antimycin-insensitive and SHAM-sensitive. Clones recovered are tested for complementation of hemL, hemB and hemA mutants. Growth is tested for inhibitor sensitivity. Sequences of cDNA clones that provide functional alternative oxidase activity by these tests are compared with known AOX gene sequences (McIntosh, 1994).

The *Escherichia coil* strain XL 1-Blue was prepared for infection with the *T. gondii* phage library according to Stratagene manufacturer's protocol. The RH tachyzoite library, in the λ-ZAP vector system was titred, and $10^6$ pfu are added to the XL1-Blue preparation. Approximately $6 \times 10^5$ plaques are plated on agar onto 150 mm$^2$ petri dishes containing NZY medium, and grown at 42° C. for 3.5 or 8 hours, depending upon which screening method is employed. If antibodies are used for screening, IPTG-soaked nitrocellulose filters are placed on the plates after the short incubation period, and the growth of the plaques is allowed to proceed for an equivalent period of time. Filters are blocked in BLOTTO overnight. Screening is carried out under the same conditions which had been optimized during Western blotting with that primary antibody, and the appropriate secondary antibody. If DNA probes are used for screening, the plaques are grown for 8 hours post-infection, and placed at 45° C. for 2 hours to overnight. Nitrocellulose filters are placed on the plates, and all subsequent steps for lysis and fixing of the DNA are as specified in the Stratagene protocol. Filters are placed into a pre-hybridization solution containing Denhardts, SSC, SDS, and denatured salmon sperm DNA, as directed in Ausubel et al. (1987). Blots are hybridized to $^{32}$P-labeled probe overnight. Low stringency washes, containing 5×SSC and 0.1% SDS are performed twice at room temperature, and high stringency washes with 0.2×SSC and 0.1% SDS are performed at a temperature dependent upon the degree of homology between the probe and the *T. gondii* DNA.

6) Assays for the presence of genes:

Evidence for the presence of the genes which encode the novel enzymes is obtained by demonstrating enzyme activity and/or Western blot analysis of Apicomplexan whole cell lysates and/or polymerase chain reaction and/or probing the genomic DNA of the parasite with the homologous DNA. Identification of the genes is accomplished by screening an Apicomplexan cDNA library with the antibody to homologous enzymes from plants or other microorganisms or probes which recognize the genes which encode them and/or complementation of mutant bacteria lacking the enzyme with Apicomplexan DNA.

7) Mutant-Knockouts:

The alternative mitochondrial oxidase pathway is the preferred oxidative pathway for bradyzoites and is likely to be important for their survival. The genetic system used to examine the function of the gene via targeted gene knock-outs and allelic replacements essentially as described (Donald & Roos, 1993, 1994, 1995). The alternative oxidase is not absolutely required for growth when cytochrome oxidase can be active and mutants are recoverable. The AOX-null strains may be hypersensitive to GSAT inhibitors, both in vitro and in vivo. The ability of the AOX-null strains to switch stages, both in vitro and in vivo is determined. The AOX-null strains are examined for stage specific antigens. Virulence and ability to form cysts are assessed in vivo in C3H/HeJ mice as described herein.

Knockouts with a bradyzoite antigen reporter gene are produced and these constructs and organisms with the genes knocked out are cultured under conditions that would ordinarily yield a bradyzoite phenotype. These are used to determine whether expression of the "knocked out" gene is critical for bradyzoite antigen expression and the bradyzoite phenotype.

8) Similar "knockouts" of EPSP synthase or chorismate synthase are produced.

9) Similar procedures are used for other Apicomplexan parasites. For example, a similar genetic system is available for *P. falciparum*.

Example 11

Production, Testing, and Use of Vaccines against Apicomplexa

"Knock out" organisms (e.g., lacking GSAT, or alternative oxidase or EPSP-synthase or chorismate synthase or UDP-glucose starch glycosyl transferase) are produced as described herein. The knock-out vaccine strain in some cases is cultivated in tissue culture because components which are deficient are provided by a single product or a plurality of products. DNA constructs and proteins are produced and tested as described herein (see Materials and Methods) using unique genes and sequences and assay systems and methods which are known to those of skill in the art and disclosed herein. Briefly, they are used to immunize C3H mice, and tissues of immunized and control mice are subsequently examined for persistence of parasites. These immunized mice and controls are challenged per-orally with 100 cysts of Me49 strain or intraperitoneally with 500 RH strain tachyzoites. Effect of immunizations on survival, and tissue parasite burden are determined (McLeod et al., 1988). Parasite burden refers to quantitation of numbers of parasites using PCR for the B1 *T. gondii* gene, quantitating numbers of cysts in brain tissue, quantitating numbers of parasites by inoculating serial dilutions of tissues into uninfected mice when the RH strain of *T. gondii* is utilized and assessing survival of recipient mice as 1 parasite of the RH strain of *T. gondii* is lethal. Ability to prevent congenital transmission and to treat congenital infections is also a measure of vaccine efficacy. Vaccines are useful to prevent infections of livestock animals and humans. Standard methods of vaccine development are used when substantial prevention of infection is achieved in murine models.

Example 12

Nucleotide and Deduced Amino Acid Sequence of *T. gondii* Chorismate Synthase cDNA Animals and most protista (e.g. Leishmania) rely exclusively on exogenous folates. Previous studies which demonstrate the efficacy of anti-folates for the treatment of toxoplasmosis have implied that *T. gondii* has the enzymes necessary to synthesize folates. For this purpose, *T. gondii* uses PABA. The biochemical events that lead to PABA production in *T. gondii* or any other Apicomplexan have not been previously characterized. In algae, plants, certain bacteria and fungi, the shikimate pathway facilitates the conversion of shikimate to chorismate, a three step reaction catalyzed by three enzymes, shikimate kinase, 3-phospho-5-enolpyruvyl shikimate synthase (EPSP synthase) and chorismate synthase. Chorismate is then used as a substrate for the synthesis of PABA. In plants, EPSP-synthase and chorismate synthase are encoded in the nucleus. In plants, algae and bacteria, chorismate is not only an essential substrate for the synthesis of folate, but it is required for the synthesis of ubiquinone and certain aromatic amino acids. The shikimate pathway may occur both inside and outside of the plastid: For example, EPSP synthase exists in two forms in Euglena, one associated with the plastid of those grown in the light and the other found in the cytosol of those grown in the dark.

Apicomplexan parasites utilize the shikimate pathway for folate synthesis. An inhibitor of the EPSP synthase, an essential enzyme in this pathway, restricts the growth of *T. gondii, P. falciparum* and *C. parvum* in vitro. This inhibitor, NPMG, synergizes with pyrimethamine and sulfadiazine to prevent *T. gondii* multiplication. NPMG also synergizes with pyrimethamine to protect mice against challenge with the virulent RH strain of *T. gondii*. The sequence of a *T. gondii* gene that encodes a putative chorismate synthase, that has considerable homology with chorismate synthases from other organisms, provides information useful in developing novel antimicrobial agents.

A partial cDNA sequence of approximately 250 bases was identified from the "Toxoplasma EST Project at Washington University." This sequence, when translated, had approximately 30% homology with chorismate synthase from a number of organisms. Both strands of the corresponding clone were sequenced and found to be 2312 bases in length (FIG. 9). Analysis revealed a large open reading frame of 1608 base pairs which would encode a 536 amino acid protein. Homology was determined by the use of CLUSTAL X, a computer program that provides a new window base user interface to the CLUSTAL W multiple alignment program. (Thompson, 1994). The deduced amino acid sequence has considerable identity (44.5 to 51.4%) with chorismate synthases of diverse species (FIG. 10). The putative *T. gondii* protein differs from other known chorismate synthases in length. Chorismate synthases from other organisms range in length from 357–432 amino acids. The larger size of the *T. gondii* protein is due to an internal region that has no counterpart in other known chorismate synthases and is novel. The function of this region remains to be determined. The *T. gondii* chorismate synthase sequence was used in a search with the BLAST program. An EST from a *Plasmodium falciparum* cDNA library was located that has considerable homology with the *T. gondii* sequence. Chorismate synthase is also present in *Mycobacterium tuberculosis*.

The nucleotide sequence of the cDNA which encodes a putative *T. gondii* chorismate synthase and the amino acid sequence deduced from it is shown in FIG. 9. The deduced amino acid sequence of putative *T. gondii* chorismate synthase has substantial homologies with chorismate synthases from diverse organisms including *Solanum lycospersicum* (tomato) (SEQ ID NO: 40), *Synechocystis* species (SEQ ID NO: 38), *Hemophilus influenza* (SEQ ID NO: 42), *Saccharomyces cerevisiae* (SEQ ID NO: 39), and *Neurospora crassa* (SEQ ID NO: 41). (FIG. 10).

The Apicomplexan data base in Genbank was searched for homologies to the *T. gondii* chorismate synthase gene. A homologous *P. falciparum* EST (FIG. 11) was identified. It was sequenced. This provided additional evidence that at least a component of the shikimate pathway also was present in *P. falciparum*.

Sequencing Method

Characterization of Insert and Design of Sequencing Strategy.

Clone TgESTzy11c05.r1 was obtained from the Toxoplasma project at Washington University and supplied in the Bluescript SK vector as a phage stock. Phagemid DNA was excised by simultaneously infecting XL1-Blue cells with the phage stock and VCS-M13 helper phage. Purified phagemids were used to infect XL1-blue cells. Infected XL1-Blue cells were grown in LB media and plasmid DNA purified using Qiagen maxi-prep kits. The cDNA insert was excised using EcoR I and Xho I restriction enzymes and found to be approximately 2.4 KB. Initial sequencing of the 5 prime end of the insert's plus strand and its translation, revealed 30% homology with previously described chorismate synthases from other organisms. However, sequencing of the 5 prime end of the minus strand yielded a sequence that when translated had little apparent homology with any known protein. A series of restriction digestion experiments were performed to establish a restriction map of the insert. Restriction fragments were electrophoresed through a 1% agarose gel and fragments visualized by ethidium bromide staining and ultra-violet illumination. Due to the lack of available restriction enzyme sites within the insert, sequencing with the conventional technique of using sub-cloned overlapping restriction fragments as templates would prove to be laborious and time consuming. To circumvent this potential problem and facilitate rapid sequencing, a strategy was designed that used both conventional sub-cloned overlapping restriction fragments with standard vector annealing primers and the fill length clone with custom designed primers. Thus, sequencing was first carried out by using sub-cloned restriction fragments and the information obtained used to custom design unique sequencing primers. These primers allowed efficient sequencing of the internal regions and the external 3 prime end of each strand. The customized primers were:

| | |
|---|---|
| CS1 | 5' TGT CCA AGA TGT TCA GCC T 3' (SEQ ID NO: 6) |
| CS2 | 5' AGG CTG ATC ATC TTG GAC A 3' (SEQ ID NO: 7) |
| CS2 | 5' TCG GGT CTG GTT GAT TTT 3' (SEQ ID NO: 8) |
| CS4 | 5' GAG AGA GCG TCG TGT TCA T 3' (SEQ ID NO: 9) |
| CS5 | 5' ATG AAC ACG ACG CTC TCT C 3' (SEQ ID NO: 10) |
| CS6 | 5' CAT GTC GAG AAG TTG TTC 3' (SEQ ID NO: 11) |
| CS7 | 5' GAA CAA CTT CTC GAC ATG 3' (SEQ ID NO: 12) |
| CS8 | 5' ACT TGT GCA TAC GGG GTA C 3' (SEQ ID NO: 13) |
| CS9 | 5' GTA CCC CGT ATG CAC AAG T 3' (SEQ ID NO: 14) |
| CS10 | 5' TGA ATG CAA CTG AAC TGC 3' (SEQ ID NO: 15) |
| CS11 | 5' GCA GTT CAG TTG CAT TCA 3' (SEQ ID NO: 16) |
| CS12 | 5' AGC CGT TGG GTG TAT AAT C 3' (SEQ ID NO: 17) |
| CS13 | 5' CTA CGG CAC CAG CTT CAC 3' (SEQ ID NO: 18) |
| CS14 | 5' CGT CCT TCC TCA ACA CAG TG 3' (SEQ ID NO: 19) |
| CS15 | 5' GTG AAG CTG GTG CCG TAG 3' (SEQ ID NO: 20) |
| CS16 | 5' CGC CTC TGA TTT GGA AGT G 3' (SEQ ID NO: 21) |
| CS17 | 5' TCT GCC GCA TTC CAC TAG 3' (SEQ ID NO: 22) |
| CS18 | 5' GAA GCC AAG CAG TTC AGT T 3' (SEQ ID NO: 23) |

Sub-cloning

Sub-clones were made from restriction fragments isolated by agarose gel electrophoresis and purified using the Qiaex gel extraction kit Qiagen, Chatsworth Calif. Double digestions of the plasmid with Hinc II and Pst I resulted in 4 fragments of 500, 800, 300 and 4000 base pairs. The 800 bp fragment, corresponding to the base pairs 800–1600 was ligated into the bluescript KS vector. The 1600–2400 base pair portion of the insert was obtained in a similar manner using Pst I and Xho I restriction enzymes and ligated into the bluescript KS vector. Ligations were performed for 12 hours at 18 degrees centigrade on a PTC 100, programmable thermal cycler, MJ Research Inc. Watertown, Mass. Plasmids containing the restriction fragments were used to transform DH5α competent cells. Plasmid DNA was purified using Qiagen maxi-prep kits.

Primer Sequence Design

Primers were designed based on the sequencing information obtained from restriction enzyme fragments. To facilitate sequencing of a region on the same strand and 5 prime to an already sequenced portion of insert, primers were designed from an area approximately 200–300 nucleotides 5 prime into the last obtained sequence. For sequencing of the complementary strand, primers were designed to be the complement and reverse of the same region. Primers were designed to be 18–25 nucleotides in length and have a Tm of 55–60 degrees centigrade. G plus C content was 45–55 percent. Primers were designed to have minimal self annealing and to have a low propensity for primer to primer annealing. Primers with the ability to form stable secondary structures were not designed. These criteria for the design of primers were based on theoretical considerations and results of other experiments which found that primers which had Tms of much less than 55 degrees centigrade failed to work or performed poorly, producing ambiguous sequences of low quality.

Sequencing and Assembly of Sequence Information

All sequencing was performed using a Perkin Elmer automated sequencer. The three purified plasmids containing the entire cDNA or a restriction fragment were used as templates for sequencing reactions with the standard M13 and reverse primers. The sequences obtained were used to design primers which allowed sequencing of the internal regions of the inserts. This process was repeated until both strands of the entire clone were sequenced. Chromatograms were critically edited and controlled for quality using Sequencher software. Edited chromatograms of excellent quality were assembled with the same software package and a consensus sequence obtained. The consensus sequence was analyzed for open reading frames using Macvector software package. Kodak International Biotechnology, Inc., New Haven, Conn.

Example 13

Transit Sequence of *T. gondii* Chorismate Synthase

Homology with other peptides was sought using the Genbank database and the unique sequence in the *T. gondii* chorismate synthase (amino acids 284 to 435, FIG. 11). There was thirty percent identity and forty-five percent homology, with a number of conserved motifs, between this unique sequence of *T. gondii* chorismate synthase and the amyloplast/chloroplast transit (translocation) sequence of the Waxy protein (UDP-glucose starch glycosyl transferase) of *Zea mays* (sweet corn). The same methods whereby the *Zea mays* transit sequence was analyzed (Klosgen and Well, 199 1), i.e., construction of the transit sequence with a reporter protein, immunolocalization of the protein, creation of the construct with deletions or mutations of the transit sequence and subcellular immunolocalization using immunoelectronmicroscopy are useful for proving that this is a transit sequence in the *T. gondii* chorismate synthase. A useful reporter protein for a chimeric construct is β glucoronidase of *E. coli*, expressed under the control of the 35S promoter of cauliflower mosaic virus. The β glucuronidase alone is expressed, in parallel. The transit peptide chimeric construct is found in the plastid. The control β glucuronidase is found in the cytoplasm. Another useful reporter system is green fluorescent protein (gfp). Antibodies to the chorismate synthase protein are also used to detect the presence of the product of the gene (with the transit sequence) in the plastid and the product of a construct in which the transit sequence is not present in the cytoplasm only. This is used to immunolocalize proteins in different life-cycle stages. Further mutations and deletions are made which identify the minimal transit sequence using the same techniques as described above for the entire peptide. Antisense, ribozyme or intracellular antibodies directed against the transit sequence nucleic acid or translated protein are useful as medicines. The amino acid or nucleic acid which encodes the transit sequence are the bases for diagnostic reagents and vaccine development. This transit sequence is useful for the construction of ribozyme, antisense nucleic acids, intracellular antibodies which target a key parasite protein, and creation of constructs with accompanying molecules which are lethal to the parasites (Roush, 1997; Mahal et al., 1997). This transit sequence also is useful because it provides a general extension of the concept of transit and targeting sequences in Apicomplexan parasites that enable targeting of other parasite organelles in addition to plastids. The transit sequence of *Zea mays* and *T. gondii* are shown in FIG. 11.

Example 14

Nucleotide and Deduced Amino Acid Sequences of *P. falciparum* Chorismate Synthase EST Sequencing of *P. falciparum* chorismate synthase EST followed the same pattern as described above for sequencing the *T. gondii* chorismate synthase gene with the following exceptions: There was difficulty in obtaining sequence from the 3' region of the cDNA due to an unstable polyA tail. This made it necessary to do all sequencing approaching from the 5' end using gene walking techniques and subcloning of restriction fragments. The AT richness of *P. falciparum* genes increased the complexity of design of the customized primers. The customized primers utilized were:

PFCS1 AGC TAT TGG GTG GATC (SEQ ID NO: 24)
PFCS2 TCC ATG TCC TGG TCT AGG (SEQ ID NO: 25)
PFCS3 ATA AAA ACA CAT TGA CTA TTC CTT C (SEQ ID NO: 26)
PFCS4 GGG GAT TTT TAT TTT CCA ATT CTT TG (SEQ ID NO: 27)
PFCS5 TTG AAT CGT TGA ATG ATA AGA C (SEQ ID NO: 28)
PFCS6 TTT TAG ATC AGC AAT CAA ACC (SEQ ID NO: 29)
PFCS7 AAC TTT TTA TCT CCA TAC TTT G (SEQ ID NO: 30)
PFCS8 GAA GGA ATA GTC AAT GTG TTT TTA T (SEQ ID NO: 31)
PFCS9 GTA TTT TAC CAA GAT TAC CAC CC (SEQ ID NO: 32)
PFCS10 CCC CCA ACA CTA TGT CG (SEQ ID NO: 33)
PFCS11 CAG TGG GCA AAA TAA AGA (SEQ ID NO: 34)
PFCS12 CCA GTG GGC AAA ATA A (SEQ ID NO: 35)
PFCS13 GGA AGA GAA ACA GCC AC (SEQ ID NO: 36)
PFCS14 TGC TGC TGG GGC GTG (SEQ ID NO: 37)

The gene and deduced amino acid sequences are in FIG. 12.

Example 15

Southern Blotting Demonstrates Presence of Chorismate Synthase (and by Inference All of the Shikimate Pathway) in Apicomplexan Parasites Southern blotting using the *T. gondii* chorismate synthase gene as a $^{32}$P labeled probe demonstrated homology at moderate stringency (e.g. 0.2×SSC, 0.1% SDS at 42° C.) [more stringent conditions define greatest relatedness of genes] with *Eimeria bovis* and *Cryptosporidium parvum* DNA.

This *T. gondii* cDNA also comprises a probe for screening cDNA libraries of all other Apicomplexa to identify their chorismate synthase genes. The same principles are applicable to all the other enzymes in Table 1.

Example 16

Gene Expression, Recombinant Protein, Production of Antibody and Solving the *T. gondii* and *P. falciparum* Crystal Structures of Chorismate Synthase to Establish Their Active Site and Secondary Structure These are done using standard techniques. The gene construct is placed within a competent *E. coli*. Recombinant enzyme is identified by homologous antibody reactivity and purified using affinity chromatography. Fusion proteins are useful for isolation of recombinant protein. Protein is injected into rabbits and antibody specific to the protein is obtained and utilized to purify larger amounts of native protein for a crystal structure. The crystal structure provides information about enzyme active site and facilitates rational drug design (Craig and Eakin, 1997). Recombinant proteins are used for high-throughput screens to identify new antimicrobial agents.

Example 17

Other Uses (e.g. in Diagnostic Reagents and Vaccines) of the Chorismate Synthase Gene as a Representative Example of Uses of Each of the Genes and Enzymes in These Pathways that Are Not Present or Rarely Present in Animals These uses include *T. gondii* genes and proteins used as diagnostic reagents and as a vaccine to protect against congenital infection. Recombinant protein (all or part of the enzyme) is produced and is used to elicit monoclonal antibodies in mice and polyclonal antibodies in rabbits. These antibodies and recombinant protein (e.g., to *T-gondii* chorismate synthase) are used in ELISA (e.g. antibody to human IgG or IgM, or IgA or IgE attached to ELISA plate+serum to be tested+antibody conjugated to enzyme+ enzyme substrate). The recombinant proteins, pooled human sera from known uninfected individuals (5 individual sera pooled) and infected individuals (5 individuals with acute infection sera pooled, 5 individuals with chronic infection sera pooled) are the controls. This test is useful with serum or serum on filter paper. Another example of a diagnostic reagent are primers to amplify the target transit sequence or another portion of the chorismate synthase sequence unique to *T. gondii*. PCR with these primers is used with whole blood to detect presence of the parasite. Such assays have proven to be useful using the *T. gondii* B1 gene (Kirisits, Mui, Mack, McLeod, 1996).

Another example of a diagnostic reagent is useful in outpatient settings such as an obstetrician's office or in underdeveloped areas of the world where malaria is prevalent. FABs of monoclonal antibodies (which agglutinate human red cells when ligated) (Kemp, 1988) are conjugated to antibodies to the target sequence or selected enzyme. Antigen conjugated anti-red cell Fab also is used to detect antibody to the component. A positive test occurs when the enzyme or antibody is circulating in the patient blood and is defined by agglutination of red cells (in peripheral blood from the patient) mixed with the conjugated antibodies: Controls are the same as those specified for the ELISA.

Examples of vaccines are protein, peptides, DNA encoding peptides or proteins. These are administered alone or in conjunction with adjuvants, such as ISCOMS. These vaccine preparations are tested first in mice then primates then in clinical trials. Endpoints are induction of protective immune responses, protection measured as enhanced survival, reduced parasite burden, and absent or substantial reduction in incidence of congenital infection (McLeod et al., 1988).

Example 18

*T. gondii* Chorismate Synthase Genomic Sequence

Genomic clones are isolated from commercially available genomic libraries (AIDS repository) using the identified cDNA clones as probes in the screening process. The genomic library, as λ phage, is isolated onto NZY agar plates using XL1-Blue *E. coli* as the host, resulting in plaques following a 37° C. incubation. The cDNA sequence is radiolabeled with $^{32}$P and hybridized to nylon membranes to which DNA from the plaques has been covalently bound. Plasmids from candidates are excised and their restriction enzyme-digested inserts sequenced. Experimental details are as described in Ausubel et al. (1987).

Example 19

*P. falciparum* Chorismate Synthase Genomic Sequence

This will be done with a gene specific subgenomic library as described in Example 18.

Other examples of enzymes and the genes which encode them and which are characterized as outlined above include: glutamyl-tRNA synthetase; glutamyl-tRNA reductase; prephenate dehydrogenase aromatic acid aminotransferase (aromatic transaminase); cyclohexadienyl dehydrogenase tryptophan synthase alpha subunit; tryptophan synthase beta subunit; indole-3-glycerol phosphate synthase (anthranilateisomerase), (indoleglycerol phosphate synthase); anthranilate posphoribosyltranferase; anthranilate synthase component I; phosphoribosyl anthranilate isomerase anthranilate synthase component II; prephenate dehydratase (phenol 2-monooxygenase) catechol 1,2-deoxygenase (phenol hydroxylase); cyclohexadienyl dehydratase; 4-hydroxybenzoate octaprenyltransferase; 3-oxtaprenyl-4-hydroxybenzoate carboxylyase dehydroquinate synthase (5-dehydroquinate hydrolase); chorismate synthase (5-enolpyruvylshikimate 3-phosphate phosphlyase); dehydroquinate dehydratase; shikimate dehydrogenase; 3-deoxy-d-arabino-heptuloonate 7 phosphate synthase; chorismate mutase (7-phospho-2-dehydro-3-deoxyarabino-heptulate aldolase); 3-deoxy-d-arabino-heptuloonate 7 phosphate synthase; shikimate 3-phosphotransferase (shikimate kinase); UDP glucose starch glycosyl transferase; Q enzymes; acetohydroxy acid synthase; chorismate synthase malate synthase, isocitrate lyase; 3-enolpyruvylshikimate phosphate synthase (3-phosphoshikimate-1 carboxyvinyltransferase).

Example 20

T. gondii Chorismate Synthase, EPSP Synthase, and Shikimate Kinase Activities were Demonstrated Assay for chorismate synthase, EPSP synthase and shikimate kinase in T. gondii were performed and demonstrated such activity.

Example 21

T. gondii Dehydroquinate Dehydratase Activity is Demonstrated

An assay for dehydroquinate dehydratase in T. gondii was performed and demonstrated such activity.

Example 22

GSAT Activity is Demonstrated in T. gondii Tachyzoite Lysates

An enzymatic assay (Sangwan and O'Brian, 1993) demonstrates GSAT activity in T. gondii lysates. The buffer contains 0. 1 M MOPS (3-[N-morpholino]propanesulfonic acid), pH 6.8, 0.3M glycerol, 15 mM $MgCl_2$, 1 mM dithiothreitol, 20 $\mu$M pyridoxal phosphate, 1 mM PMSF (phenylmethylsulfonyl fluoride). The MOPS, glycerol and $MgCl_2$ are combined and then pH'd. This is important because the glycerol alters the pH, so it must be added first. This is filter sterilized and has a long shelf life. When the buffer is needed, DTT, pyridoxal phosphate and PMSF are added immediately prior to use. The protein extract stock should be ~10 mg/ml if possible. The principle of the assay is conversion of substrate which produces a change in color due to the reactant.

Example 23

Isocitrate Lyase Activity is Demonstrated in T. gondii Tachyzoite Lysates

An enzymatic assay demonstrates isocitrate lyase activity in T. gondii isolates prepared by disruption of the parasite membranes using french press or a lysis buffer. Demonstration that the lysis buffer does not alter enzyme activity is carried out by performing the assay with known substrate and enzyme in the lysis buffer and documenting presence of enzyme activity.

Example 24

Alternative Oxidase Activity is Demonstrated in T. gondii Preparations

T. gondii tachyzoites and bradyzoites are assayed for alternative oxidase activity and such activity is found to be present in greater amounts in bradyzoites.

Example 25

Novel Substrate Competitors and Transition State Analogues of Enzymes Inhibit Apicomplexan Enzymes Some inhibitors are competitive substrates or transition state analogues and they are utilized in the enzyme assay, in vitro with tachyzoite and bradyzoite preparations and with native enzyme, tissues culture assays and in in vivo models as described above. These provide a model paradigm for designing inhibitors of any of the enzymes specified above. Briefly, inhibitors are produced as follows: Competitive substrates are produced by designing and synthesizing compounds similar to known compounds but modified very slightly. For example, inhibitors related to glyphosate are known. The structures of glyphosate, sulfosate and the precursor for EPSP have similarities (please see below). Inhibitors are designed by modifying substrates in such a manner that the modification interferes with the enzyme active site. This can be performed using molecular modeling software. Similarly, halogenated substrates for other enzymes have functioned effectively as nontoxic inhibitors. The principles are applicable to the design of inhibitors for any of the unique enzymes with well characterized substrates and active sites.

The approaches to rational design of inhibitors include those standard in the art (Craig and Eakin, 1997; Ott et al., 1996). These methods use information about substrate preference and three-dimensional structure of the target enzyme (e.g., chorismate synthase or EPSP synthase).

In one approach, the structure of the target is modeled using the three-dimensional coordinates for amino acids in a related enzyme. An example of this is that the crystal structure of GSAT from a plant has been solved and its active site is known.

In another part of this approach, expression of high levels of recombinant enzyme is produced using cDNA (e.g., the chorismate synthase of T. gondii or P. falciparum) and quantities of protein adequate for structural analysis, via either NMR or X-ray crystallography are obtained.

Drug resistant mutants are produced in vitro following mutation with nitrosoguanidine and culture with the inhibitor. The surviving organisms have acquired resistance to the inhibitor. This process is carried out either with the Apicomplexan parasite or with bacteria or yeast complemented with the gene encoding the enzyme or part of the gene (e.g., without the transit sequence). PCR amplifies the relevant cDNA and this cDNA encoding the resistant enzyme is cloned and sequenced. The sequence is compared with that of the enzyme that is not resistant. With the information about the inhibitor target and three-dimensional structure, the point mutations which cause resistance are analyzed with computer graphic display. This information provides the mechanism for altered binding of the drug, and the inhibitory compound is then modified to produce second generation medicines designed to treat resistant pathogens prior to their development in nature.

An example of the use of toxic analogues to kill parasites used by others provides a means whereby there is production of analogues toxic to parasites. Specifically, the purine analogue prodrugs, 6 sulfanylpurinol, 6 thioguanine, 6 thioxanthine and allopurinol interact with hypoxanthine phosphoribosyltransferase which is responsible for salvage of purines used to produce AMP and GMP. Such toxic analogues are effective against the plant-like enzymes in the pathways (see Table 1) in Apicomplexans.

Transit state analogues bind with extraordinarily high efficiency to the enzyme active site and are predicted from the three-dimensional structure and kinetic information. Analogues that mimic the structural properties and electrostatic surface potentials for the transition state are designed and synthesized. Empirical testing using recombinant enzyme demonstrates that these transition state analogues are good leads with high affinity for the active site of the target enzyme.

Multisubstrate analogues are useful because they markedly enhance the binding affinity to the enzyme. Similarly, if enzymes in a cascade are linked in such a manner that the substrate for one reaction provides the substrate for the next reaction, multisubstrate analogues are more useful.

Selective inhibitor design and lead refinement:

Co-crystallization of inhibitors with target enzymes of host and pathogen enable three-dimensional analysis of molecular constructs and atomic interactions between inhibitors and enzymes and redesign of inhibitors (leads) to enhance their affinity for the pathogen enzyme. Iterative crystallography, lead redesign and inhibitor testing in vitro and in vivo enable design and development of potent selective inhibitors of the target of the pathogen enzyme. Recombinant methods for screening large numbers of analogues for those that bind selectively to the enzymes of specific parasites provide justification for inclusion of the analogues which bind best in the design of transition-state or multisubstrate analogues.

Additional examples (included to illustrate principles employed) but already patented by others include: Inhibitor of EPSP synthase have been designed based on the similarities of the inhibitor to the substrate. Based on molecular modeling algorithms additional inhibitors are designed.

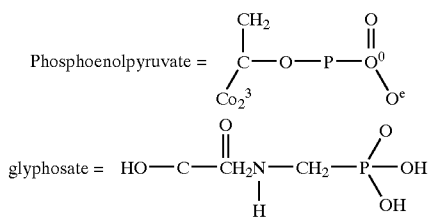

Inhibitors that effect components of these pathways are halogenated substrates or analogues which are effective competitors.

Inhibitors of Ubiquinone:

Modifications (substitutions) of benzhydroxamic acids produce CoQ (ubiquinone) analogues such as esters of 2, 3 and 3,4 dihydroxybenzoic acid and structurally related compounds.

Inhibitor of Isoleucine/valine biosynthetic pathway:

These are noncompetitive inhibitors as is shown by the lack of relatedness of the inhibitors (e.g., imidazolinones, sulfonylureas) to the target enzymes.

Inhibitors of GSAT

The following acids (5 amino-1,3 cyclohendienyl carboxylic acid, 4 amino 5 hexynoic acid (acetylenic, GABA), 4 amino 5 hexonoic acid (vinyl GABA) 2 amino 3 butanoic acid (vinyl glycine), 2 amino 4 methoxy-trans-3 butenoic acid, 4 amino 5 fluoropentanoic acid alter catalysis dependent formation of a stable covalent adduct Inhibitors of lysine biosynthetic pathway:

There are noncompetetive inhibitors of lysine synthesis that target enzymes in this patway (e.g., azi DAP, 3, 4 didehydro DAP, 4 methylene DAP4, 4 methylene DAP6) and inhibitors of other plant-like enzymes as in Table 1A and B.

Example 26

Modifications of Inhibitory Compounds to Improve Oral Absorption Tissue Distribution (Especially to Brain and Eye)

Tissue distribution is characterized using radiolabeled inhibitor administered to mice with its disposition to tissues measured by quantitation of radiolabel in tissues. Compounds are modified to improve oral absorption and tissue distribution by standard methods.

Example 27

Efficacy of Antimicrobial Compounds Alone, Together and in Conjoint Infections in Murine Models Inhibitors of plant-like pathways are effective against the Apicomplexan infection alone, together with the bacterial and/or fungal infections and also treat the bacterial and fungal infections alone.

Presence of inhibitory activity of new antimicrobial compounds is tested using Apicomplexans, bacteria and fungi in enzymatic assays, in vitro, and in vivo assays as described above and known to those of skill in the art.

Infections are established in murine models and the influence of an inhibitor or combination of inhibitors on outcomes are determined as follows:

Infections:

Infections with *Toxoplasma gondii, Pneumocystis carinii, Mycobacterium tuberculosis, Mycobacterium avium* intracellular and *Cryptosporidium parvum* are established alone and together using an immunosuppressed rodent model. Endpoints in these infections are:

Survival: Ability of an inhibitor to protect the infected animal is measured as prolonged survival relative to the survival of untreated animals.

Parasitemia: Is a measure using isolation of mRNA and RT-PCR. A competitive inhibitor is used for quantitation.

Tissue Parasite Burden: Is determined by quantitating brain and eye cyst numbers.

Inflammatory Response: This is noted in histopathologic preparations.

Representative combinations of inhibitors are NPMG and sulfadiazine, SHAM and atovaquone, NPMG and pyrimethamine, NPMG and SHAM.

Example 28

Establishing Efficacy, Safety, Pharmakokinetics, and Therapeutic/Toxic Index

The testing in murine models includes standard Thompson tests. Testing of antimicrobial agents for efficacy and safety in primate models for malaria is performed. Dosages are selected based on safety information available from data bases of information concerning herbicides and the literature. Measurements of serum and tissue levels of antimicrobial compounds are performed using assays which detect inhibitor concentrations and concentrations of their metabolites. Representative assays are high performance liquid chromatography, and assaying tissues for percentage of radiolabeled compounds administered, using liquid scintillation, and other assays also are used.

Example 29

Determining whether There Is Carcinopenicity and Teratogenicity

Standard assays to evaluate carcinogenicity and teratogenicity include administration of medicines as described above to rodents and observation of offspring for teratogenic effects and carcinogenicity (i.e. development of malignancies). Observation includes general physical examination, autopsy and histopathologic studies which detect any teratogenic or carcinogenic effects of medicines.

Example 30

Constructs to Measure Parasitemia

Portions of genes are deleted and the shorter gene is used as an internal standard in RT PCR assays to measure amount of parasites present (Kirisits, Mui, McLeod, 1996).

Example 31

Vaccine Constructs and Proteins and Their Administration

These are prepared, as described. They include DNA constructs (Ulmer, Donnelly and Liu, 1996) with the appropriate gene or portions of the gene alone or together, with adjuvants. Representative adjuvants include ISCOMS, nonionicsurfactant, vesicles, cytokine genes in the constructs and other commonly used adjuvants. Native and recombinant proteins also are used in studies of vaccines. Protection is measured using immunologic in vitro assays, and assessing enhanced survival, reduction of parasitemia tissue and parasite burden and prevention of congenital infection [McLeod et al., 1988].

Example 32

Stage-Specific Expression of Proteins

This is evaluated by enzyme assays, northern or western.analysis, ELISA, semi-quantitation of mRNA using RT-PCR with a competitor as internal standard in gene-knockout organisms using culture conditions (e.g. alkaline pH, increased temperature, nitric oxide exposure) which ordinarily elicit a bradyzoite phenotype, or engineering a reporter construct and characterizing presence of the reporter in stage specific expression of antigens. Ability to change between life cycle stages or to persist in a particular life cycle stage is affected by presence or absence of particular plant-like genes and by treatment of inhibitors with plant-like processes. Suitable examples of plant-like enzymes which make parasites less able to switch from or persist in a specific life cycle stage include: alternative oxidase, enzymes critical for amylopectin synthesis such as starch synthases, UDP glucose-glucosyl starch transferase and branching (Q) enzymes.

Example 33

Preparation of Diagnostic Test Reagents and Diagnostic Tests

These assays are as described (Boyer and McLeod, 1996). Sensitivity and specificity are established as is standard in the field. Tests and reagents include ELISAs in which antibodies to the proteins or peptides and recombinant proteins of this invention such as chorismate synthase (Aroc) are used and PCR methodology in which primers to amplify DNA which encodes the enzymes, or parts of this DNA, are used. A test useful in an outpatient setting is based on conjugation of a monoclonal antibody to human red blood cells with antibody to plant-like peptides or proteins based on an assay described by Kemp et al. (Kemp et al, 1988). The red cells are cross linked via the monoclonal antibody moiety, resulting in agglutination of the red blood cells in the blood sample if the antigen or antibody to the parasite component is present in the blood sample. ELISA and PCR can be utilized with samples collected on filter paper as is standard in Newborn Screening Programs and also facilitates outpatient and field use.

Example 34

Development and Use of Antisense Oligonucleotides in Design and Use of Medicines to Protect Against Apicomplexans Antisense oligonucleotides directed against the nucleic acids which encode the enzymes of the essential parasite metabolic process described herein are effective medicines to treat these infections. Antisense oligonucleotides also are directed against transit sequences in the genes. Antisense oligonucleotides are short synthetic stretches of DNA and RNA designed to block the action of the specific genes described above, for example, chorismate synthase of *T. gondii* or *P. falciparum,* by binding to their RNA transcript. They turn off the genes by binding to stretches of their messenger RNA so that there is breakdown of the mRNA and no translation into protein. When possible, antisense do not contain cytosine nucleotides. Antisense reagents have been found to be active against neoplasms, inflammatory disease of the bowel (Crohn's Disease) and HIV in early trials. Antisense will not contain cytosine nucleotides followed by guanines as this generates extreme immune responses (Roush, 1997). Antisense oligonucleotides with sequence for thymidine kinase also is used for regulatable gene therapy.

Example 35

Ribozymes and Other Toxic Compounds as Antimicrobial Agents

Ribozymes are RNA enzymes (Mack, McLeod, 1996) and they and toxic compounds such as ricins (Mahal et al, 1997) are conjugated to antisense oligonucleotides, or intracellular antibodies, and these constructs destroy the enzyme or other molecules.

Example 36

Intracellular Antibodies to Target Essential Enzymes Proteins and Organelles

Intracellular antibodies are the Fab portions of monoclonal antibodies directed against the enzymes of this invention or portions of them (e.g., anti-transit sequence antibodies) which can be delivered either as proteins or as DNA constructs, as described under vaccines.

Example 37

Development of New Antimicrobial Compounds Based on Lead Compounds

The herbicide inhibitors comprise lead compounds and are modified as is standard. Examples are where side chain modifications or substitutions of groups are made to make more active inhibitors (Table 1). Their mode of action and structure as well as the enzyme and substrate structures are useful in designing related compounds which better abrogate the function of the enzymes. Examples of such substrate or active site targeting are listed in Table 1.

Native or recombinant protein used in enzymatic assays and in vitro assays described above are used to test activity of the designed newly synthesized compounds. Subsequently, they are tested in animals.

Example 38

Trials to Demonstrate Efficacy of Novel Antimicrobial Agents for Human Disease

Trials to demonstrate efficacy for human disease are performed when in vitro and murine and primate studies indicate highly likely efficacy and safety. They are standard Phase I (Safety), Phase II (small efficacy) and Phase III (larger efficacy with outcomes data) trials. For medicines effective against *T. gondii* tachyzoites, resolution of intracerebral Toxoplasma brain lesions in individuals with HIV infection with no other therapeutic options available due to major intolerance to available medicines is the initial strategy for Phase II trials. Endpoints for trials of medications effective against *T. gondii* bradyzoites include absence of development of toxoplasmic encephalitis in individuals with HIV. HIV infected patients who also are seropositive for *T. gondii* infection are evaluated. Evaluation is following a one-month treatment with the novel anti *T. gondii* medicines. Observation is during a subsequent 2 year period when the patients peripheral blood CD4 counts are low. Effective medicines demonstrate efficacy measured as absence of *T. gondii* encephalitis in all patients. Otherwise, 50% of such individuals develop toxoplasmic encephalitis. When medications efficacious against bradyzoites and recrudescent toxoplasmic encephalitis in patients with AIDS are discovered and found to be safe, similar trials of efficacy and safety for individuals with recurrent toxoplasmic chorioretinitis are performed. All such trials are performed with informed consent, consistent with Institutional NIH, and Helsinki guidelines applicable to treatment trials involving humans.

Example 39

Vaccine Trials for Humans

After vaccine efficacy in rodent models to prevent congenital and latent Toxoplasma infection are established, for component vaccines only, trials to establish safety and efficacy in prevention of congenital and latent infection are performed. They follow standard procedures for phase I, II and III trials as outlined above and as is standard for vaccine development.

Endpoints for vaccine effect and efficacy are development of antibody and cell-mediated immunity to *T. gondii* (effect) and most importantly, prevention of *T. gondii* congenital infections. After establishing in phase I trials that the vaccine is entirely safe, nonpregnant women of childbearing age will be vaccinated with recombinant vaccine. Assay for efficacy is via a serologic screening program to detect newborn congenital toxoplasmosis (described in Boyer and McLeod, 1996) with usual testing to document whether seropositive infants are infected (described in Boyer and McLeod, 1996).

Example 40

Vaccine Efficacy and Safety for Livestock Animals

The efficacy of candidate vaccines is tested in sheep as previously described (Buxton et al., 1993). Vaccines are live attenuated, genetic constructs or recombinant protein. The most efficious routes and frequency of inoculation is assessed in a serious of experiments as described below. Intra-muscular, sub-cutaneous and oral are the preferred routes, although intravenous, intraperitoneal and intradermal routes may also be used. Scottish blackface or/and swaledale ewes, four to six years old are tested for IgG antibodies to *Toxoplasma gondii* using an ELISA assay. Only seronegative animals are used for the study. Three groups of 10–15 ewes are used for each experiment. Groups 1 are vaccinated, while group 2 and 3 are not. Three months later all ewes are synchronized for estrous and mated. At 90 days gestation the ewes in groups 1 and 2 are given 2000 sporulated oocyst of *T. gondii*.

The outcome of pregnancy is monitored in all groups. Aborted lambs or those dying soon after birth are examined histologically and by PCR for the B1 gene or subinoculation into mice or tissue culture, for the presence of *T. gondii*. All placentas are examined histologically and as above for parasites. Lambs are weighed at birth. Precolostral serum is taken from each lamb. Congenital transmission is assessed by performing ELISA assays on the serum for IgG or IgM. Protection is measured as a decrease in congenital transmission, a decrease in the incidence or severity of congenital disease, or a decrease in abortion.

MATERIALS AND METHODS

A. Methods to Assay Candidate Inhibitors

1. Inhibitors of *Toxoplasma gondii* a) Cell lines:

Fibroblasts. Human foreskin fibroblasts (HFF) are grown in tissue culture flasks in Iscoves' Modified Dulbecoes Medium (IDMM), containing 10% fetal bovine serum, L-glutamine and penicillin/streptomycin at 37° C. in 100% humidity and a 5% $CO_2$ environment. Confluent cells are removed by trypsinization and washed in IMDM. They are used in a growth phase for toxicity assays or when 100% confluent for parasite inhibition assays.

b) Tachyzoites:

Tachyzoites of the RH and pTg strains of *T. gondii* are passaged and used for in vitro studies (McLeod et al., 1992). The R5 mixed tachyzoite/bradyzoite mutant was derived from mutagenesis with nitrosoguanidine in the present of 5 hydroxynapthoquinone. These organisms are used for in vitro experiments at a concentration of $2 \times 10^3$, $2 \times 10^4$, or $2 \times 10^5$ organisms per ml, dependent upon the planned duration of the experiment (i.e., larger inoculations for shorter duration experiments).

c) Bradyzoites:

Bradyzoites are obtained as described by Denton et al. (1996b). Specifically, C57BL10/ScSn mice are infected intraperitoneally with 20 cysts of the Me49 strain of *T. gondii*. Their brains are removed 30 days later and homogenized in PBS by repeated passage through a 21 gauge needle. Aliquots containing the equivalents of 3–4 brains are diluted in PBS and 6.5 mls of 90% percoll added to the mixture which is allowed to settle for 30 mins. 2 mls of 90% Percoll is then added as a bottom layer and the mixture centrifuged for 30 mins at 2500×g. The cysts are recovered from the bottom layer and a small portion of the layer above. After the removal of Percoll by centrifugation, the contaminating red blood cells are removed by lysis with water followed by the addition of 1 ml of 10×PBS per 9 ml brain suspension in water. Bradyzoites are released from the purified cysts by digestion in a 1% pepsin solution for 5 minutes at 37° C. This method routinely permits recovery of greater than 90% of the cysts present which yields approximately 100 bradyzoites per cyst. Bradyzoites are used at concentrations of $2\times10^3$, $2\times10^4$ and $2\times10^5$ per ml in parasite growth inhibition assays. pH shock is also used to retain organisms in bradyzoite stage when such pH does not interfere with inhibitor activity.

d) Inhibitors:

Inhibitor compounds are tested over a range of concentrations for toxicity against mammalian cells by assessing their ability to prevent cell growth as measured by tritiated thymidine uptake and inspection of the monolayer using microscopic evaluation. A range of concentrations that are non-toxic in this assay are tested for their ability to prevent the growth of *T. gondii* and also other Apicomplexans within these cells.

i.) Heme Synthesis: The inhibitor of the heme synthesis pathway, gabaculine (Grimm, 1990; Elliot et al., 1990; Howe et al., 1995; Mets and Thiel, 1989; Sangwan and O'Brian 1993; Matters and Beale, 1995) is used at a concentration of 20 mM [which has been demonstrated to be effective against tachyzoites of the RH and R5 strains]. Other inhibitors of this pathway include 4 amino-5-hexynoic acid and 4-aminofluoropentanoic acid which provide additional corroborative evidence that this pathway is present.

ii) Glyoxylate Cycle: The inhibitor of isocitrate lyase is 3 nitropropionic acid (ranging from 0.005 to 5 mg/ml in vitro).

iii) Alternative Oxidase *T. gondii* bradyzoites use unique alternative oxidases. Alternative oxidase is necessary and sufficient for bradyzoite survival. Methods to characterize plant alternative oxidases are described (Hill, 1976; Kumar and Söll, 1992; Lambers, 1994; Li et al., 1996, McIntosh, 1994).

For the in vitro studies, cell lines that lack functional mitochondria are used. These cell lines are used to allow the study of inhibitors effective against the conventional or alternative respiratory pathways within the parasite, but independent of their effects on the host cell mitochondria. Two cell lines, a human fibroblast cell line (143B/206) lacking mitochondrial DNA, and the parental strain (143B) which poses functional mitochondria are used. These cell lines have been demonstrated to support the growth of *T. gondii* (Tomavo S and Boothroyd J C, 1995). SHAM, an inhibitor of the alternative respiratory pathway is used at concentrations between 0.25 and 2 μg/ml in vitro.

iv) Shikimate Pathway. For EPSP synthase, the inhibitor is N-(phosphonomethyl)glycine (concentrations of 3.125 mM in folate deficient media).

e) Culture assay systems for assessing inhibitor effect:

i) Toxicity assays: Aliquots of cells (HFF) are grown in 96-well tissue culture plates until 10% confluent. Cells are incubated with various concentrations of drug for 1, 2, 4 and 8 days. Cultures are pulsed with tritiated thymidine (2.5 μCi/well) for the last 18 hours of the culture after which the cells are harvested using an automated cell harvester and thymidine uptake measured by liquid scintillation.

ii) In vitro parasite growth inhibition assays: Confluent monolayers of HFF cells, grown in 96-well plates are infected with *T. gondii* tachyzoites of the RH strain and serial dilutions of anti-microbial compound are applied 1 hour later. *T. gondii* growth is assessed in these cultures by their ability to incorporate tritiated uracil (2.5 μCi/well) added during the last 18 hours of culture. After harvesting cells with an automatic cell harvester, uracil incorporation is measured by liquid scintillation. Alternatively, confluent HFF cells are grown in the chambers of Labtech slides and parasite growth is assessed microscopically following fixation in aminoacridine and staining in 10% Giemsa (McLeod et al., 1992).

f) Product rescue assays to evaluate specificity of the inhibitor:

To attempt to demonstrate specificity of the site of action of the inhibitor, growth inhibition assays are performed in the presence of varying concentrations of product, e.g., in the case where gabaculine is the inhibitor, ALA is added simultaneously to determine whether product rescue occurs. This type of study is only interpretable when rescue is demonstrated because it is possible that exogenous "product" is not transported into the *T. gondii* within host cells. For EPSP synthase, product rescue assay is performed with PABA.

g) Assays for synergy in vitro.

This is an assay in which ≦50% inhibitory concentrations of two antimicrobial agents are added alone and together to determine whether there is an additive, synergistic or inhibitory interaction. All other aspects of this assay are as described herein.

2. Inhibitors of *Cryptosporidia parvum*

*C. parvum* oocysts at 50,000/well were incubated with each drug (PRM=paromomycin which is the positive control, NPMG, gabaculine, SHAM, 8-hydroxyquinoline) at 37° C. (8% carbon dioxide) on confluent MDBKF5D2 cell monolayers in 96 well microtiter plates. The level of infection of each well was determined and analyzed by an immunofluorescence assay at 48 hours using as an antibody *C. parvum* sporozoite rabbit anti-serum (0.1%), and using fluorescein-conjugated goat anti-rabbit antibody (1%). Data are expressed as mean parasite count/field when 16 fields counted at 10× magnification "s.d. of the mean. (FIG. 6)

3. Inhibitors of *Plasmodium falciparum*

This assay is performed in folate deficient RPMI 1640 over a 66 hour incubation in plasma as described by Milhous et al. (1 985). Both the W2 clone DHFR resistant phenotype and the D6 clone are used (Odula et al., 1988) (Table 3).

4. Inhibitors of *Eimeria tenella*

Susceptibility of *Eimeria tenella* in vitro is analyzed by a method similar to that described by McLeod et al., 1992 or for Cryptosporidium as disclosed herein.

5. In vivo studies, measurement of parasitemia of *Toxoplasma gondii*

A method to measure the amount of parasitemia in mouse peripheral blood has been developed. Briefly, the target for PCR amplification is the 35 fold repetitive B1 gene of *T. gondii* and the amplification was performed using primers previously reported. In order to semiquantitate the PCR product and to avoid false negative results, a competitive internal standard is generated using a linker primer and the original B1 primers. Competitive PCR was performed by spiking individual reactions (containing equal amounts of genomic DNA) with a dilution of the internal standard. Since this internal control contains the same primer template sequences, it competes with the B1 gene of *T. gondii* for primer binding and amplification. The sensitivity of the PCR reaction in each sample can be monitored. Following competitive PCR, the PCR products are distinguished by size and the amount of products generated by the target and internal standard can be compared on a gel. The amount of competitor DNA yielding equal amounts of products gives the initial amount of target gene.

6. Interpretation of Data/Statistical Analysis of Data

In vitro studies are performed with triplicate samples for each treatment group and a mean ±sd determined as shown in the FIGs. All in vivo studies utilize at least 6 mice per group. Statistical analysis performed by Students' t-test or the Mann-Whitney U-test. A p value of $\leq 0.05$, is considered statistically significant.

B. Western Blots Demonstrate Plant-Like Enzymes

Western analysis for GSAT, isocitrate lyase, malate synthase, alternative oxidase and EPSP synthase is used to demonstrate the presence of plant-like enzymes in many Apicomplexan parasites, e.g., Plasmodia, Toxoplasma, Cryptosporidia, Malaria and Eimeria.

Tachyzoites and bradyzoites (McLeod et al. 1984, 1988; Denton et al., 1996a, b), or their mitochondria and plastids are isolated as previously described. Equivalent numbers of tachyzoites and bradyzoites are separately solubilized in 2× sample buffer and boiled for 5 minutes. Samples are electrophoresed through a 10 percent SDS-polyacrylimide gel. Proteins are transferred to a nitrocellulose membrane at 4° C., 32V with 25 mM Tris and 192 mM glycine, 20% v/v methanol, pH 8.3. Blots are blocked in PBS (pH 7.2) containing 5% powered milk and 0.1% Tween 20 for 2 hours at 20° C. After washing in PBS (pH 7.2), 0.1% Tween 20, blots are stained with polyclonal or monoclonal antibodies specific for alternative oxidases in PBS (pH 7.2) containing 0.1% Tween 20 for 1 hour at 20° C. Following washing in PBS (pH 7.2) containing 0.1% Tween 20, blots are incubated with an appropriate secondary antibody conjugated to HRP at a dilution to be determined by methods known in the art. After further washes, binding is visualized by chemoilluminescence (Amersham).

Antibodies to various enzymes, e.g., soybean GSAT, barley GSAT, synechococcus GSAT, plant and/or trypanosome alternative oxidase, cotton isocitrate lyase, cotton malate synthase, soybean malate synthase, petunia EPSP synthase were used to determine whether homologous enzymes are present in *T. gondii* tachyzoites, bradyzoites, mitochondrial and plastid enriched preparations. Antibodies used include monoclonal antibodies to *Trypanosoma bruceii* and Voo Doo Lily (Chaudhuri et al. 1996) alternative oxidase and polyclonal antibody to *Trypanosoma bruceii* alternative oxidase. The hybridizations with antibodies to plant and related protozoan alternative oxidases demonstrated the relatedness of *T. gondii* metabolic pathways to those of plants and other non-Apicomplexan protozoans. The products GSAT and alternative oxidase were demonstrated by Western analysis. Both polyclonal and monoclonal antibodies were reacted with alternative oxidase to confirm this observation.

C. Probing Other Parasite Genes

The genes isolated from *T. gondii* as described herein are used to probe genomic DNA of other Apicomplexan parasites including Plasmodia, Cryptosporodium, and Eimeria.

D. Genomic Sequence

Genomic clones are identified and sequenced in the same manner as described above for cDNA except a genomic library is used. Analysis of unique promoter regions also provide novel targets.

E. Enzymatic Activity Demonstrates Presence of Plant-Like Enzymes in Metabolic Pathways The presence of the enzymes putatively identified by inhibitor studies is confirmed by standard biochemical assays. Enzyme activities of GSAT, isocitrate lyase, malate synthase, alternative oxidase, and EPSP synthase, chorismate synthase, chorismate lyase, UDP-glucose starch glycosyl transferase and other enzymes listed herein are identified using published methods. Representative methods are those of Jahn et al, 1991; Weinstein and Beale, 1995; Kahn et al, 1977; Bass et al., 1990; Mousdale and Coggins (1985). In addition, enzyme activity is used to determine in which of the tachyzoite and bradyzoite life cycle stages each pathway is operative. Tachyzoites and bradyzoites are purified as described herein. The parasites are lysed in 50 mM HEPES (pH7.4) containing 20% glycerol, 0.25% Triton X-100 and proteinase inhibitors (5 mM PMSF, 5FM E64, 1FM pepstatin, 0.2 mM 1,10-phenanthroline). This method has proven successful for measurement of phosphofructokinase, pyruvate kinase, lactate dehydrogenase, NAD- and NADH-linked isocitrate dehydrogenases and succinic dehydrogenase activity in tachyzoites and bradyzoites of *T. gondii* (Denton et al, 1996a,b).

1) GSAT:

GSAT activity is measured by the method of Jahn et al., (1991), which uses GSA as substrate. GSA is synthesized according to methods of Gough et al. (1989). Heat-inactivated (60° C., 10') lysates are employed as non-enzymatic controls. ALA is quantified following chromatographic separation (Weinstein and Beale, 1985). This approach allows the definitive detection of GSAT activity in crude extracts.

2) ALA Synthase:

To determine whether parasites contain ALA synthase, an activity also present in mammalian host cell mitochondria, cell fractions from purified parasites are assayed. (Weinstein and Beale, 1985) ALA produced from added glycine and succinyl CoA is quantified as for GSAT.

3) Isocitrate Lyase:

The biochemical assay for isocitrate lyase activity used is the method of Kahn et al. (1977).

4) Alternative Oxidase: activity is measured in parasite lysates or purified mitochondria or plastids by oxygen uptake using an oxygen electrode described by Bass et al. (1990). Confirmation of the oxidation being due to alternative oxidase(s) is achieved by successful inhibition of oxygen uptake in the presence of 0.5 mM SHAM, but not in the presence of KCN.

5) Shikimate Pathway:

The biochemical assay for EPSP synthase, chorismate synthase, chorismate lyase; activity in cellular lysates is conducted as described by Mousdale and Coggins (1985) and Nichols and Green (1992).

6) Branched Amino Acids:

The biochemical assay for hydroxy acid synthase is as described.

7) Amylopectin Synthesis:

The biochemical assays for starch synthase, Q enzymes, and UDP-glucose starch glycosyl transferase are as described.

8) Lipid Synthesis:

Assays for lipid synthases are as described.

Some of the additional representative enzyme assays are precisely as described by Mousdale and Coggins(1985) and are as follows:

5-Enolpyruvylshikimate 3-phosphate synthase is assayed in forward and reverse directions as described previously (Mousdale and Coggins 1984). Shikimate:NADP oxidoreductase (shikimate dehydrogenase), shikimate kinase, 3-Dehydroquinase (DHQase) are assayed. Assay mixtures contained in a total volume of 1 ml: 100 mM potassium phosphate (pH 7.0) and 0.8 mM ammonium 3-dehydroquinate. 3-Dehydroquinate synthase is assayed by coupling for forward reaction to the 3-dehydroquinase reaction; assay mixtures contained in a total volume of 1 ml: 10 mM potassium phosphate (pH 7.0), 50 $\mu$M NAD$^+$. 0.1 mM CoCl$_2$, 0.5 nkat partially-purified *Escherichia coli* DHQase and (to initiate assay) 0.4 mM DAHP. The DAHP is prepared from *E. coli* strain AB2847A and DHQase from *E. coli* strain ATCC 14948.

Assay of DAHP synthase is by a modification of the method of Sprinson et al. Assay mixtures contained in a total volume of 0.5 ml : 50 mM 1,3-bis [tris(hydroxymethyl)-methylamino] propane-HCl (pH 7.4), 1 mM erythrose 4-phosphate, 2 mM phosphoenolpyruvate and 1 mM CoCl$_2$. The reaction is initiated by the addition of a 50 to 100 $\mu$l sample containing DAHP synthase and terminated after 10 min at 37° C. by 100 $\mu$l 25% (w/v) trichloroacetic acid. The mixture was chilled for 1 h and centrifuged to remove precipitated protein. A 200 $\mu$l aliquot of the supernatant was mixed with 100 $\mu$l 0.2 M NaIO$_4$ in 9 M H$_3$PO$_4$ and incubated at 37° C. for 10 min, 0.5 ml, 0.8 M NaASO$_2$ and 0.5 M Na$_2$SO$_4$ in 0.1 M H$_2$SO$_4$ in 0.1 m H$_2$SO$_4$ was then added and the mixture left at 37° C. for 15 min; 3 ml 0.6% (w/v) sodium thiobarbiturate and 0.5 M Na$_2$SO$_4$ in 5 mM NaOH was added and the mixture placed in a boiling-water bath for 10 min. After cooling to room temperature the solution was centrifuged (8500 ×g, 2 min) and the optical density at 549 nm read immediately. Appropriate controls assayed in triplicate lack substrates, sample or both." Another representative assay is an assay for chorismate lyase which is as described by Nichols and Green, 1992:

Chorismate lyase assays are carried out in a volume of 0.5 ml containing 50 mM Tris-HCl (pH 7.5), 5 mM EDTA, 10 mM 2-mercaptoethanol, 60 $\mu$M chorismate, and 0.2 to 4 U of chorismate lyase. After incubation at 37° C. for 30 min, 4-hydroxybenzoate is detected and quantitated by high-pressure liquid chromatography (HPLC). Fifty microliters of each reaction mixture is applied to an HPLC system (Waters 625) equipped with a Nova-Pak C$_{18}$ column equilibrated in 5% acetic acid and monitored at 240 nM. The height of the 4-hydroxybenzoate peak is compared with those of standard curves generated by treating known amounts of 4-hydroxybenzoate in a similar manner. One unit of chorismate lyase activity is defined as the amount of enzyme required to produce 1 nmol of 4-hydroxybenzoate in 30 min at 37° C.

Assays for 4-aminobenzoate and 4-amino-4-deoxychorismate are performed as described previously." Enzyme Assays: The 5-enolpyruvylshikimate-3-phosphate (EPSP) synthase assay entailed monitoring the generation of EPSP using HPLC. Reaction components were separated using a Hypersil H3APS2 HPLC column (Hichrom Limited, Reading, UK) and a NaH$_2$PO$_4$ elution gradient (50–400 mM). UV spectra (200–320 nm) of the column eluate were collected to identify eluants. Shikimate-3-phosphate and 5-enolpyruvylshikimate-3-phosphate, synthesized enzymatically and purified to at least 95% purity as described (12), eluted after 3.9 and 6.8 min, respectively, phosphoenolpyruvate did not interfere with the EPSP detection and eluted after 5.3 min. The peaks at 215 nm were integrated; the EPSP produced was quantified using a standard curve of authentic EPSP. Parasite extracts were produced at 4° C. by suspension of pure tachyzoites in extraction buffer (50 mM Tris.HCl, pH 7.5, containing complete TM protease inhibitor cocktail [Boehringer Mannheim, 1 tablet per 50 ml buffer]), sonication 3 times for 3 seconds at 30 second intervals, and centrifugation at 12000 g for 15 min. The resulting supernatant was diluted 6-fold with extraction buffer and loaded onto a ResourceQ column (1 ml, Pharmacia) equilibrated with extraction buffer. The bound protein was eluted in a single step using extraction buffer containing 500 mM KCl. The eluted material was used for enzyme assay. The assay mix contained 1 mM phosphoenolpyruvate, 1 mM SP and 50 mM HEPES, pH 7.5. The reaction was started by addition of parasite extract and incubation was at 30° C. Times 10 $\mu$l aliquots were subjected to HPLC analysis. Protein concentrations of lysates were determined using the Lowry method. (Roberts et al., 1998, In Press)

E. Construction and Analysis of Gene "Knock-Outs"

In order to determine whether a gene, e.g., chorismate synthase or alternative oxidase is essential for growth or survival of the organism, gene knockout organisms are generated by the method of Roos et al., 1996. Specifically, the strategy for creating mutants is with homologous recombination and to generate a targeted gene knock-out a sequential positive/negative selection procedure is used (Roos et al., 1996). In this procedure positive and negative selectable markers are both introduced adjacent to, but not within the cloned and suitably mutated locus. This construct is transfected as a circular plasmid. Positive selection is applied to yield a single-site homologous recombinant that is distinguished from non-homologous recombinants by molecular screening. In the resulting 'pseudodiploid,' mutant and wild-type alleles flank selectable marker and other vector sequences. In the next step, parasites are removed from positive selection, which permits recombination between the duplicated loci. This event appears to occur at a frequency of 2×10$^{-6}$ per cell generation. These recombinants are isolated with negative selection. Next, they are screened to distinguish those that have recombined in a manner that deletes the mutant locus and yields a wild-type revertant from those that deleted the wild-type gene to leave a perfect allelic replacement.

This 'hit-and-run' approach has the disadvantage of being time-consuming. Nonetheless, it offers several distinct advantages over other gene knock-out strategies. First, because gene replacement occurs by two sequential single-cross-overs instead of one double cross-over which is a very rare event, it is more likely to be successful. Second, because selectable marker(s) are located outside of the targeted gene itself, experiments are not limited to gene knock-outs. A variety of more subtle point mutations are introduced as allelic replacements. Third, this strategy provides a means of distinguishing essential genes from those which cannot be deleted for purely technical reasons. Specifically, if the hit-and-run mutagenesis procedure yields only wild-type revertants instead of the theoretical 1:1 ratio of wild-type:mutant, this provides positive evidence that the locus in question is essential.

An example is a knockout created for the chorismate synthase gene. It also can be made more general to include knockout of other genes for attenuated vaccines such as EPSP synthase and alternative oxidase. The parasite with the gene of interest to be knocked out is grown ("manufactured") in vitro in presence of product, but when used in vivo the needed product is not present. The parasite functions as an attenuated vaccine as described below under vaccines. A specific example follows: Specifically, the strategy of product inhibition discussed above is also useful for growing gene knockout parasites (which lack a key gene for their survival) in vitro by providing the essential product and thus bypassing the need for the gene during in vitro propagation of the parasite. Such gene knockouts cultivated in vitro in this manner are useful attenuated organisms that are used as attenuated vaccines.

The chorismate synthase cDNA clones are used as hybridization probes for recovering genomic clones from a *T. gondii* genomic cosmid library. Coding regions are mapped onto the genomic clones using the cDNA clones as a guide. Appropriate sections are sequenced to verify the gene location. Ultimately, full genomic sequences are obtained. Enough of the genomic clones are sequenced to develop a strategy for generating a putative null allele. Segments that can be deleted at the 5' end of the coding region to generate an allele that is unlikely to generate a functional gene product are identified. A putative neutral allele is generated that can be distinguished from the wild type allele on the basis of an introduced restriction site polymorphism, but that does not differ in encoded protein sequence. These putative chorismate synthase-null and chorismate synthase-neutral alleles are cloned into the pminiHXGPRT transfection vector plasmid.

The resulting chorismate synthase-null and chorismate synthase-neutral plasmids are transfected into HXGPRT-negative strains of *T. gondii* (strains RH(EP)$^a$HXGPRT [a ME49 derivative]. Numerous independent clones are selected for survival on mycophenolic acid to select for insertion of the plasmid. These strains are screened by Southern analysis designed to detect the presence of both the normal and modified copies of the chorismate synthase gene and for tandem location of the two copies (with the vector HXGPRT gene between). This is the structure expected for insertion of the plasmid by homologous recombination at the AroC genomic locus (the "hit" needed for the hit-and-run gene knock-out strategy). The feasibility of recovering these strains is critically dependent upon the ratio of homologous to non-homologous integration following transfection, which will depend upon the length of homologous, genomic DNA in the clone (Donald and Roos, 1994; Roos et al., 1996). Eight kb of homology is sufficient to obtain >50% homologous integration (Roos et al., 1996).

HXGPRT clones with verified pseudodiploid structure of the chorismate synthase alleles are selected for loss of HXGPRT using 6-thioxanthine (the "run" part of the protocol). Numerous clones are selected. If the loss of HXGPRT is based upon random homologous exchange between the two chorismate synthase pseudodiploid alleles, theoretically half of the events should lead to excision of the modified chorismate synthase allele along with the HXGPRT, leaving the original wild type allele in the chromosome. The other half should excise the wild type allele, leaving the modified allele in the chromosome. During selection and grow-out of these clones, the medium is supplemented with chorismate at the concentration determined to best rescue cells from inhibitor toxicity. The purpose of the supplementation is to enhance the chances of recovering chorismate synthase-null strains. The genomic structure of the selected clones is examined by Southern analysis to confirm loss of the vector HXGPRT and of one copy of the chorismate synthase and to identify the remaining allele of chorismate synthase. The ratio of mutant to wild type is tabulated. The chorismate synthase-neutral allele is intended as a positive control to confirm that either allele (wild type or mutant) can be lost in this procedure. If chorismate synthase-neutral strains can be recovered but chorismate synthase-null strains cannot, the conclusion is that the chorismate synthase gene is essential for growth. If it proves possible to recover chorismate synthase-null strains, they are subjected to further phenotypic analysis, first, using immunoblotting of electrophoretically separated cell extracts to confirm absence of chorismate synthase protein, then, determining if these strains show hypersensitivity to inhibitors of the alternative oxidase or to any of the other potential inhibitors. Sensitivity to chorismate synthase inhibitors is analyzed to determine the relative specificity of inhibition. If chorismate synthase is the sole target of the inhibitors, then the null mutants should be insensitive to further inhibition. Sensitivity analysis is conducted in vitro as described herein. Whether strains show alterations in expression of the alternative oxidase or in any stage-specific antigens is of interest. These analyses are conducted by immunoblotting of electrophoretically separated cell extracts. In vivo analysis using a mouse model is conducted to determine if these strains are infective and what stages of parasites can be detected following infection. Genetically altered *T. gondii* organisms are used to infect C3H/HeJ mice by the intraperitoneal route. Mortality is monitored and brains examined for cysts at 30 days post infection.

Knockouts with bradyzoite reporter genes are useful to determine whether these enzymes influence stage switch.

Stage switch also is characterized by quantitating relative amounts of parasite mRNA present in each stage of parasite using Northern blotting, isolation of mRNA and RT-PCR using a competitive inhibitor, and enzyme assay.

G. Reagents Used for Construction of "Knock-Outs"

Library

Me49 genomic libraries are used.

Plasmids pminiHXGPRT. Contains *T. gondii* HXGPRT gene under control of DHFR-TS 5' and 3' flanking sequences. Functions as either a positive or negative selection marker (using 6-thioxanthine or mycophenolic acid, respectively) in suitable host strains.

Parasite Strains (obtained from AIDS Repository, Bethesda, Md.)

RH(EP). Wild-type host strain RH (highly pathogenic in mice).

RH(EP)$^a$HXGPRT. HXGPRT knock-out mutant of RH strain. Suitable for positive selection of HXGPRT-containing vectors.

P(LK). Wild-type host strain P, (clonal isolate of strain ME49; produces brain cysts in mice).

P(LK)HXGPRT-. HXGPRT-deficient mutant of P strain. Suitable for positive selection of HXGPRT-containing vectors.

H. Antibodies

Antibodies have been raised against homologous plant enzymes by standard techniques for both polyclonal and monoclonal antibodies (Current Protocols in Immunology, 1996).

1) Heme Synthesis

Antibody to soybean, barley and synechococcus GSAT are polyclonal antibodies with preimmune sera the control for the barley and synechococcus antibodies.

2) Glyoxylate Cycle

*T. gondii* contains a glyoxylate cycle that allows growth using lipids as a carbon source, thus the lipid mobilization pathway of *T. gondii* is similar to the pathway of plants (Tolbert, 1980). A similar approach using polyclonal antibodies to isocitrate lyase and to malate synthase and preimmune control sera are used.

3) Alternative Energy Generation

Monoclonal and polyclonal antibodies to alternative oxidases in plants (McIntosh et al., 1994) and Trypanosomes (Hill, 1976) are used.

4) Shikimate Pathway

To demonstrate that *T. gondii* has the same unique enzymes that permit interconversion of shikimate to chorismate as plants do, the antibody to shikimate pathway plant EPSP synthase is used.

5) Synthesis of Branched Chain Amino Acids

Antibodies to acetohydroxy acid synthase are used.

6) Amylose and Amylopectin Synthesis and Degradation

Antibodies to starch synthesis, branching (Q) enzymes and UDP glucose starch glycosyl transferase are used.

I. Complementation of Enzyme Deficient *E. coli* Demonstrates Functional Product The *E. coli* AroC mutant which lacks chorismate synthase (AroC) was obtained from the *E. coli* genetic stock center. AroC bacteria is made competent to take up DNA by transformation with $CaCl_2$ treatment. Alternatively, the cells are electroporated to take up DNA. The presence of the plasmid is demonstrated in this system by growth on media which contains ampicillin, as the plasmid contains an ampicillin resistance gene. Complementation is confirmed by demonstrating growth on media lacking the product catalyzed by (i.e., chorismate). Thus, this transformation/complementation is used with the *T. gondii* cDNA library system or a construct which contains some or all of the chorismate synthase gene to transform the AroC mutant. Functional enzyme is then demonstrated.

J. Immunizations of Mice for Polyclonal Antibody Production

As an alternative approach if complementation studies are unsuccessful and the monoclonal antibodies to a plant protein are not cross reactive, purified plant protein is used to immunize mice to raise polyclonal antibodies to each enzyme. Where necessary, antibodies to the pertinent enzymes are generated in mice, ND4 outbred mice are immunized with 20 µg of enzyme emulsified in Titermax complete adjuvant injected intramuscularly into their gluteal muscle. Two weeks later mice are immunized with a further 20 µg of enzyme emulsified in Titermax. After a further 2 weeks mice receive a further boost of enzyme alone in PBS by the intraperitoneal route. Mice are bled and the serum tested for specificity by the standard Western blotting technique.

K. Immunofluorescence

Antibodies used to identify enzymes in the Apicomplexan metabolic pathways disclosed here are used for immunofluorescence studies. Examples are demonstration of alternative oxidase in *T. gondii* by immunofluorescence assay (IFA). *T. gondii* alternative oxidase is immunolocalized to mitochondria.

L. ELISAs

ELISAs are used for documenting the presence and quantitating the amounts of alternative oxidase.

M. Reporter Constructs to Demonstrate Organelle Targeting Are Made and Characterized as Described Using β Glucoronidase or Other Chimeric Constructs Importance of the targeting sequence for localization of the enzyme to an organelle is demonstrated with immunoelectronmicroscopy. Organelle targeting sequences in proteins expressed in bacteria which lack the organelle cause misfolding of proteins and thereby impair protein function. A useful reporter protein for a chimeric construct is β glucoronidase, expressed in *E. coli* under control of the 355 promoter of cauliflower mosaic virus. The glucoronidase alone without the transit sequence is expressed in parallel. The transit peptide construct is found in the plastid. The control glucoronidase is found in the cytoplasm. Antibodies to the chorismate synthase protein are also used to detect the presence of the product of the gene (with the transit sequence) in the plastid and the product of a construct (in which the transit sequence is not present) in the cytoplasm only. Further mutations and deletions are made which identify the minimal transit sequence using the same techniques as described above for the entire peptide. Antisense, ribozyme or intracellular antibodies directed against the transit sequence nucleic acid or translated protein are useful as medicines. The amino acid or nucleic acid which encodes the transit sequences are the bases for development of diagnostic reagents and vaccines.

N. Modifications of Inhibitory Compounds to Improve Oral Absorption Tissue Distribution (Especially to Brain and Eye)

Tissue distribution is characterized using radiolabeled inhibitor administered to mice with its disposition to tissues measured. Compounds are modified to improve oral absorption and tissue distribution.

O. Methods to Demonstrate Protection Against Conjoint Infections

Infections are established and influence of an inhibitor or combination of inhibitors on outcomes are as outlined below.

Infections:

Infections with *Toxoplasma gondii, Pneumocystis carinii, Mycobacterium tuberculosis, Mycobacterium avium* intracellular and *Cryptosporidium parvum* are established alone and together using an immunosuppressed rodent model. Endpoints in these infections are:

Survival:

Ability of an inhibitor to protect, measured as prolonged survival.

Parasitemia:

This is measured using isolation of mRNA and RT-PCR with a competitive inhibitor for quantitation.

Tissue Parasite Burden:

This is determined by quantitating brain and eye cyst numbers.

Inflammatory Response:

This is noted in histopathologic preparations.

Representative combinations of inhibitors are NPMG and sulfadiazine, SHAM and atovaquone, NPMG and pyrimethamine, NPMG and SHAM.

P. Testing of Antimicrobial Compounds

Presence of inhibitory activity of new antimicrobial compounds is tested in enzymatic assays, in vitro, and in vivo assays as described above and in the literature.

Q. Efficacy, Safety, Pharmakokinetics, and Therapeutic/Toxic Index

The testing in murine models includes standard Thompson tests. Testing of antimicrobial agents for efficacy and safety in primate models for malaria is performed. Dosages are selected based on safety information available from data bases of information concerning herbicides and the literature. Measurements of serum and tissue levels of antimicrobial compounds are performed using assays which detect inhibitor concentrations and concentrations of their metabolites. Representative assays are high performance liquid chromatography, and assaying tissues for percentage of radiolabeled compounds administered using liquid scintillation and other assays also are used.

R. Carcinogienicity and Teratogenicity

Standard assays to evaluate carcinogenicity include administration of medicines as described above to rodents and observation of offspring for teratogenic effects and carcinogenicity. Observation includes general physical examination, autopsy and histopathologic studies which detect any teratogenic or carcinogenic effects of medicines.

S. Constructs to Measure Parasitemia

Portions of genes are deleted and the shorter gene is used as an internal standard in RT PCR assays to measure amount of parasites present (Kirisits, Mui, Mack, McLeod, 1996).

T. Vaccine Constructs and Proteins and their Administration

These are prepared, and sensitivity and specificity are established as is standard in the literature and as described above. Tests and reagents include DNA constructs (Tine et al., 1996) with the appropriate gene or portions of the gene alone or together, with adjuvants. Representative adjuvants include ISCOMS, nonionicsurfactant vesicles, cytokine genes in the constructs and other commonly used adjuvants. Native and recombinant proteins also are used in studies of vaccines. Protection is measured using immunologic in vitro assays, and by assessing survival and reduction of parasitemia and tissue parasite burden and prevention of congenital infection (McLeod et al., 1988).

U. Preparation of Diagnostic Test Reagents and Diagnostic Tests

These assays are as described (McLeod and Boyer, 1996). They include ELISAs in which antibodies to the proteins or peptides and recombinant proteins are used and PCR methodology in which primers to amplify DNA which encodes the enzymes or parts of this DNA are used. A test useful in an outpatient setting is based on conjugation of a monoclonal antibody to human red blood cells with antibody to peptides or proteins. The red cells are cross linked if the antibody to the parasite component interacts with the parasite component and agglutinates the red cells in the blood sample. ELISA and PCR can be utilized with samples collected on filter paper as is standard in Newborn Screening Programs and also facilitates outpatient and field use.

V. Antisense

Antisense oligonucleotides are short synthetic stretches of DNA and RNA designed to block the action of the specific genes described above, for example, chorismate synthase of *T. gondii* or *P. falciparum*, by binding to their RNA transcript. They turn off the genes by binding to stretches of their messenger RNA so that there is breakdown of the mRNA and no translation into protein. Antisense reagents have been found to be active against neoplasms, inflammatory disease of the bowel (Crohn's Disease) and HIV in early trials. Antisense oligonucleotides directed against the nucleic acids which encode the essential parasite metabolic process described herein are effective medicines to treat these infections. Antisense oligonucleotides also are directed against transit sequences in the genes. Antisense will not contain cytosine nucleotides followed by guanines as this generates extreme immune responses (Roush, 1997). Antisense oligonucleotides with sequence for thymidine kinase also is used for regulatable gene therapy.

W. Ribozymes and Other Toxic Compounds

Ribozymes are RNA enzymes (Mack, McLeod, 1996) and they and toxic compounds such as ricins (Mahal et al, 1997) are conjugated to antisense oligonucleotides (see V, DNA), or intracellular antibodies (see X, for proteins), and these constructs destroy the enzyme.

X. Intracellular Antibodies

Intracellular antibodies are the Fab portions of monoclonal antibodies directed against the enzymes or portions of them (e.g., anti-transit sequence antibodies) which can be delivered either as proteins or as DNA constructs, as described under vaccines.

Y. Development of New Antimicrobial Compounds Based on Lead Compounds

The herbicide inhibitors comprise lead compounds and are modified as is standard. For example, side chain modifications or substitutions of groups are made to make more active inhibitors. Their mode of action and structure as well as the enzyme and substrate structures are useful in designing related compounds which better abrogate the function of the enzymes. Examples of such substrate or active site targeting are described above.

Native or recombinant protein is used in enzymatic assays and in vitro assays described above are used to test activity of the designed newly synthesized compounds. Subsequently, they will be tested in animals.

Z. Trials to Demonstrate Efficacy for Human Disease

Trials to demonstrate efficacy for human disease are performed when in vitro and murine and primate studies indicate highly likely efficacy and safety. They are standard Phase I (Safety), Phase II (small efficacy) and Phase III (larger efficacy with outcomes data) trials. For medicines effective against *T. gondii* tachyzoites, resolution of intracerebral Toxoplasma brain abscess in HIV-infected individuals with no other therapeutic options available due to major intolerance to available medicines is the initial strategy for Phase II trials. For medications effective against *T. gondii* bradyzoites, absence of development of toxoplasmic encephalitis in individuals with HIV infection and individuals who are seropositive for *T. gondii* infection followed after a one-month treatment for a 2 year period when their CD4 counts are low. Effective medicines demonstrate efficacy, as 50% of such individuals otherwise develop toxoplasmic encephalitis. When medications efficacious against bradyzoites and recrudescent toxoplasmic encephalitis in patients with AIDS are discovered and found to be safe, similar trials of efficacy and safety for individuals with recurrent toxoplasmic chorioretinitis are performed.

DEFINITIONS 3-deoxy-d-arabino-heptuloonate 7 phosphate synthase: An enzyme which functions in chorismate synthesis.

3-enolpyruvyshikimate phosphate synthase (3-phosphoshikimate-1-carboxyvinyltransferase): An enzyme which functions in chorismate synthesis.

3-NPA: An inhibitor of isocitrate lyase in the glyoxylate pathway and also of succinate dehydrogenase.

3-oxtaprenyl-4-hydroxybenzoate carboxylyase: An enzyme which functions in ubiquinone synthesis.

4-hydroxybenzoate octaprenyltransferase: An enzyme which functions in ubiquinone synthesis.

8-OH-quinoline: An inhibitor of the alternative oxidase.

Abscissic Acid Metabolism in Plants: A 15-carbon sequiterpenoid synthesized partly in plastids by the mevalonic acid pathway. Abscissic acid protects plants against stress and is a marker of the plant's maturation and activation of transcription, and causes dormancy. Inhibits protein synthesis and leads to specific activation and deactivation of genes.

Acetohydroxy acid synthase: Enzyme which catalyzes production of acetohydroxy acids (the branched chain amino acids valine, leucine and isoleucine in plants).

Alternative oxidase: An enzyme important in the alternative pathway of respiration. There are examples of alternative oxidases in plants and trypanosomes. (Pollakis et al., 1995; Rhoads & McIntosh, 1992; Clarkson et al., 1989).

Alternative respiration or energy generation: A different pathway for energy generation utilizing the alternative oxidase and election flow in the electron transport chain which is not dependent on conventional cytochromes or heme.

Altered gene includes knockouts.

Amide: The R portion of the amino group has an amino group connected to a carbonyl carbon. Glutamine and asparagine are amides. Important for nitrogen transport and storage.

Amylopectin: A branched starch of plants. Also found in *T gondii* bradyzoites.

Amyloplast: Storage granule for starch in plants. Derived from chloroplasts.

Amylose: An unbranched starch of plants.

Anabolism: Formation of large molecules such as starch, cellulose, proteins, fats and nucleic acids from small molecules. Requires input of energy.

Anthranilate phosporibolsyltransferase: An enzyme which functions in tryptophan synthesis.

Anthranilate synthase component I: An enzyme which functions in tryptophan synthesis.

Anthranilate synthase component II: An enzyme which functions in tryptophan synthesis.

Antimicrobial agent: A chemical, for example a protein or antisense nucleic acid which effectively inhibits or kills a pathogenic microbe. There are examples (Schwab et al., 1994; Strath et al., 1993; Beckers et al., 1995; Blais et al., 1993; Fichera et al., 1995; Pfefferkorn & Borotz, 1994; Pfefferkorn et al., 1992; Pukivittaykamee et al., 1994).

Apicomplex: The common feature of Apicomplexan parasites including a conoid and rhoptry organelles and micronemes at the apical end of the parasite.

Apicomplexan parasite: A microorganism that belongs to the Apicomplexan group of parasites. These parasites share a number of morphologic features, including a conoid and rhoptry which are organelles in the cytoplasm at the apical end of the organism and plastids which are multilamellar structures. Representative examples of Apicomplexan parasites include *Toxoplasma gondii*, Plasmodium, Cryptosporidia and Eimeria.

Aromatic acid aminotransferase (aromatic transaminase): An enzyme which functions in tyrosine synthesis.

Aspartate, glutamate and glutamine synthesis: Involve glutamine synthase and glutamate synthetase and are plastid associated in plants. Glutamine synthase in plants is inhibited by the herbicide glufosinate (2 amino-4-[hydroxymethylphosphinyl)butanoic acid. Glutamine synthase also is present in animals.

ATP-phosphofructokinase: (ATP-PFK) May exert control over glycolytic pathway because a step when hexoses phosphate cannot also be used to form sucrose or starch. Nearly all animals lack PPi-PFK with plant-like substrate specificity (i.e. PPi, not ATP).

Auxins: Growth regulators in plants, which are tryptophan derivatives. Herbicides modeled on auxins are structural mimics of these compounds rather than inhibitors of auxin function.

Biochemical pathways: Biochemical pathways include metabolic pathways. Any chemical reaction in life. Herein "biochemical pathways" and "metabolic pathways" are used interchangeably.

Bradyzoite: The slowly replicating life cycle stage of the Apicomplexan parasite *Toxoplasma gondii*. This stage is responsible for latent and recrudescent infection due to this parasite. The morphologic features which characterize this parasite stage are electron dense rhoptries and amylopectin granules. Bradyzoites contain a plastid organelle as do other life cycle stages of this parasite. This parasite stage also has specific antigens which other life cycle stages do not have, including bradyzoite surface antigen 4 and bradyzoite antigen 5 (lactate dehydrogenase), which is an intracellular and cyst matrix antigen. Bradyzoites exist together in a structure called a cyst which has a cyst wall and matrix. Cysts contain a few to thousands of bradyzoites. The cyst containing bradyzoites is a major means of transmission of the organism *Toxoplasma gondii* when it is ingested in meat which is not cooked to well done. It is also a form of the organism responsible for recrudescent eye and brain disease in infants and children who are congenitally infected with the parasite and also in patients whose immune system is not normal.

Branched chain amino acid synthesis (valine, leucine and isoleucine) involving acetohydroxy acid synthase, is the first of the series of reactions, is another metabolic pathway present in plants but not in animals.

Branched chain amino acids: Amino acids (valine, leucine and isoleucine), the synthesis of which can be inhibited by sulfonylurea and imidazolinone herbicides. There are examples in plants (Kuriki et al., 1996; Morell et al., 1997; Kortostee et al., 1996; Grula et al, 1995; Khoshnoodi et al., 1996).

Branching or Q enzyme: Forms branches in amylopectins between C6 of the main chain and C1 of the branch chain.

Catabolism: Degradation or breakdown of large molecules to small molecules, often releasing energy.

Calmodulin: is a calcium binding protein (Robson et al., 1993)

Catechol 1,2-deoxygenase (phenol hydroxylase): An enzyme which functions in phenylalanine synthesis.

Chloroplast: A DNA-containing multilamellar organelle of plants and algae associated with metabolic pathways important for photosynthesis and other energy production. Chloroplasts utilize proteins encoded in their own DNA and also proteins encoded by nuclear DNA.

Chorismate: The product of the action of the enzyme EPSP synthase on shikimate.

Chorismate lyase: An enzyme responsible for the conversion of chorismate to 3,4-dihydroxybenzoate.

Chorismate mutase (7-phospho-2-dehydro-3-deoxy-arabino-heptulate-aldolase): An enzyme which functions in chorismate synthesis.

Chorismate synthase: An enzyme responsible for the conversion of 3-phospho 5-enolpyruvyl shikimate to chorismate.

Chorismate: The product of the action of the enzyme EPSP synthase on shikimate.

Competitive inhibitors: Structures sufficiently similar to the substrate that they compete for the active site of the enzyme. Addition of more natural substrate overcomes effect of the inhibitor.

Components: includes nucleic acids, proteins, peptides, enzymes, peptide targeting sequences, transit peptides, carbohydrates, starch, lipids, hormones, for example those listed in Table 1 and other constituents of metabolic pathways or products derived from these components.

Conventional energy generation: Usual pathways of generation of energy in mitochondria utilizing cytochromes for the transfer of electrons.

Conversion of Fats to Sugars in Plants: Occurs by oxidation and the glyoxylate cycle.

Cryptosporidiosis: The disease due to the Apicomplexan parasite *Cryptosporidium parvum*. It causes self-limited diarrhea or no symptoms in immunologically normal individuals. In individuals who have immunocompromising illnesses, such as the acquired immune deficiency syndrome, Cryptosporidiosis causes life-threatening, persistent, copious, watery diarrhea.

*Cryptosporidium parvum:* Cryptosporidium parvum is an Apicomplexan parasite which causes cryptosporidiosis.

Cyanide-insensitive, non-heme "alternative" oxidase is a metabolic activity that is found in most eukaryotic plants and algae and is absent from multicellular animals. The alternative oxidase is a single polypeptide enzyme that lacks heme and can serve as the terminal electron acceptor to support respiratory growth of *E. coli* in the absence of heme. The coupling efficiency of this oxidase is lower than that of the cyanide-sensitive cytochrome oxidase. That is, not as many protons are pumped across the mitochondrial inner membrane in parallel with electron transfer through the alternative oxidase as they are through the cytochrome oxidase. The alternative oxidase appears to be used by plants and algae only under certain conditions. The alternative oxidase is also used during different life-cycle stages or under different environmental conditions. Thus, inhibitors of the alternative oxidase may act cooperatively or synergistically with GSAT inhibitors.

Cyclohexadienyl dehydratase: An enzyme which functions in phenylalanine synthesis.

Cyclohexadienyl dehydrogenase: An enzyme which functions in tyrosine synthesis.

Cytochrome oxidase: An enzyme utilized in the conventional pathway of energy generation.

Dehydroquinate dehydratase: An enzyme which functions in chorismate synthesis.

Deoxyribonucleases: Enzymes which are hydrolases which hydrolyze DNA (phosphate esters)

*Eimeria bovis:* Causes bovine eimeriosis.

*Eimeria maxima* and *Eimeria tenella:* Cause eimeriosis in chickens.

Eimeria: A group of Apicomplexan parasites which cause gastrointestinal disease in agriculturally important animals including poultry and cattle. These economically important parasites include *Eimeria tenella, L. maxima* and *E. bovis*.

Endosymbiont: An organism which is taken up by another organism and then lives within it.

Enzyme: A protein which catalyzes (makes more rapid) the conversion of a substrate into a product. Enzymes are catalysts which speed reaction rates generally by factors between $10^8$ and $10^{20}$. They may require ion or protein cofactors. Control is by products and environmental changes. There are more than 5000 enzymes in living systems. Enzymes are named with common or trivial names, and the suffix-ase which characterizes the substrate acted upon (e.g., cytochrome oxidase removes an electron from a cytochrome). Sequential series of steps in a metabolic pathway. Enzymes that govern the steps in a metabolic pathway are sometimes arranged so that a kind of assembly-line production process occurs.

EPSP synthase: An enzyme important in the conversion of shikimate to chorismate.

EST: Expressed sequence tag; a short, single pass cDNA sequence generated from randomly selected library clones.

Eukaryote: Microorganism or phylogenetically higher organism, the cells of which have a nucleus with a limiting membrane.

Fatty Acid Synthesis in Plants: Occurs in chloroplasts of leaves and proplastids of seeds and roots. Mainly palmitic acid and oleic acid. AcetylCo A carboxylases differ in plants and animals. Linoleic acid synthase and linoleneic acid synthase are lipid synthases present in plants and not animals.

Glycolysis→pyruvate→acetyl CoA

Example:

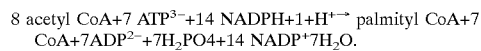
8 acetyl CoA+7 ATP$^{3-}$+14 NADPH+1+H$^{+-}$ palmityl CoA+7 CoA+7ADP$^{2-}$+7H$_2$PO4+14 NADP$^+$7H$_2$O.

Fragment: Refers to a sequence of nucleic acids or aminoacids, where a fragment is sufficient to function as a component of or product derived from an Apicomplexan as defined herein.

Gabaculine: An inhibitor of the enzyme GSAT in the heme synthesis pathway.

Gene: Nucleotide sequence which encodes an amino acid sequence or another nucleotide sequence.

Giberellin Metabolism in Plants: Plant hormones which promote plant growth, overcome dormancy, stimulate G1 to S transition and shorten S phase of cell cycle, increase hydrolysis of starch and sucrose into glucose and fructose. They are derivatives of ent-gibberellane skeleton synthesized from a 2acetyl CoA to mevalonic acid to isopenternyl pyrophosphate to 4 isopentenyl pyrophosphate to geranylgeranyl pyrophosphate to copalylpyrophosphate to kaurene to kaurenol to keaurenal to kaurenoic acid to GA$_{12}$ aldehyde to other giberellins. These functions are not clearly established but it is hypothesized that hydrolysis of starch to sugar occurs by inducing formation of amylase enzymes. Isoprenoid compounds, diterpenes synthesized from acetate units of acetyl coenzyme A by mevalonic acid pathway stimulate growth. Inhibitors of giberellin synthesis include phosphon D, Amo 1618 (blocks conversion of geranyl pyrophosphate to CO palylpyrophosphate), phosphon D, which also inhibits conversion of (oxidation) formation of Kaurene, CCC or cycocel, ancymidol, and pactobutrazol (blocks oxidation of karene and kaurenoic acid). Young leaves are major sites for giberellin synthesis. These plant hormones which induce hydrolysis of polysaccharide into hexoses are used in glycolysis. When hexoses are abundant, glycolysis is more rapid.

Glutamyl-tRNA reductase: An enzyme which functions in heme synthesis.

Glutamyl-tRNA synthetase: An enzyme which functions in heme synthesis.

Glycolysis in Plants: Several reactions of glycolysis also occur in plastids. Glycolysis=lysis of sugar; degradation of hexosis to pyruvic acid in plants. In animals, degradation of glycogen (animal starch) to pyruvate. Plants form no glycogen.

Glyoxylate pathway: The pathway important for lipid degradation which takes acetyl CoA and converts it to CoA-SH through the conversion of isocitrate to C4 acids including succinate. This pathway utilizes isocitrate lyase and also converts glyoxylate to malate, a reaction catalyzed by the enzyme malate synthase. The glyoxysome or Glyoxylate pathway which is cytoplasmic in certain algae involves isocitrate lyase and malate synthase to metabolize lipids and provide C4 acids. A metabolic distinction between autotrophic eukaryotes and heterotrophs is the presence of a glyoxylate cycle. This cycle employs two enzymes, isocitrate lyase and malate synthase, to bypass the two decarboxylation steps of the TCA cycle and enables the utilization of carbon stored in fatty acids for growth. In plants, the enzymes of the glyoxylate cycle are compartmentalized within a unique single-membrane-bound organelle, the glyoxysome. In certain algae, the cycle is entirely cytoplasmic. In plants, these enzymes are most abundant during germination and senescence. In animals, the glyoxylate cycle enzymes have been described as being present only during starvation.

Glyoxysome: An organelle which in some instances contains enzymes important in the glyoxylate cycle.

GSAT: Glutamate-1 semialdehyde aminotransferase is the enzyme important in heme synthesis for the conversion of glutamate semialdehyde to ALA (δ-aminolevulinic acid).

Heme synthesis pathway: A metabolic pathway important for generation of heme, porphyrins and other iron sulfated proteins used in mitochondria in the conventional pathway of energy generation. This pathway occurs in plant chloroplasts and uses the nuclear encoded enzyme GSAT. A metabolic distinction between plants and animals occurs in the heme biosynthesis pathway. Non-photosynthetic eukaryotes, including animals, yeast, fungi and protists, produce δ-aminolevulinic acid (ALA), the common precursor of heme biosynthesis, by condensation of glycine and succinate. In contrast, photosynthetic organisms, including plants, algae and cyanobacteria, *E. coli* and some other bacteria synthesize ALA from glutamate (a 5-carbon pathway). Euglena utilize both condensation of glycine and succinate and the 5 carbon pathway to produce δ-aminolevulinic acid. *T. gondii* also has the ALA synthase which results in formation of heme by condensation of glycine and succinate, as does *P. falciparum* (Surolia and Padmanaban, 1992). Expression of this enzyme is developmentally regulated. For example, in plants, GSAT is most abundant in the leaves. There are examples in plants (Matters & Beale, 1995; Elich et al., 1988).

Herbicide: A compound which kills plants or algae.

Hydrolases: Enzymes which break chemical bonds (e.g., amides, esters, glycosides) by adding the elements of water.

Imidazolinones: Inhibitor of acetohydroxy acid synthase (an enzyme involved in the synthesis of branched chain amino acids, a pathway not in or rarely present in animals, Indole-3-glycerol phosphate synthase (anthranilateisomerase), (indoleglycerol phosphate synthase): An enzyme which functions in tryptophan synthesis.

Inhibitor: A compound which abrogates the effect of another compound. A compound which inhibits the replication or survival of a microorganism or the function of an enzyme or key component of a metabolic pathway or otherwise abrogates the function of another key molecule in a microorganism or other organisms or plant.

Isocitrate lyase: An enzyme which functions in glyoxylate cycle.

Isomerases: Enzymes which rearrange atoms of a molecule to form a structural isomer.

Isoprenoid Metabolism in Plants: Terpenes are isoprenoids that lack oxygen and are pure hydrocarbons; 5 carbon units with some of the general properties of lipids. Giberellins and abscidic acid are others of this vast complex of compounds not found in animals. Isoprene units (head) are $CH_2$—$CH3C$=$CH$—$CH_2$ (tail) and are synthesized entirely from acetate of acetyl CoA and restricted to plants. Synthesized by mevalonic acid pathway because mevalonate is an important intermediate.

Kinases: A subclass of transferases which transfer phosphate groups, especially from ATP.

Latency: The dormant form of the parasitic infection. One example is with *Toxoplasma gondii* in which the infection is not active and the parasite is primarily within cysts in the bradyzoite phase of the life cycle. Another example is the hypnozoite phase of *Plasmodium falciparum*.

Ligases or Synthetases: Enzymes which join two molecules coupled with hydrolysis of ATP or other nucleoside triphosphate.

Lipases: Enzymes which are hydrolases which hydrolyze fats (esters)

Lipid and terpene synthesis associated with plant plastids. Also see fatty acid synthesis and terpenes.

Lysases: Enzymes which form double bonds by elimination of a chemical group.

Malaria: Disease due to pathogenic Plasmodia. Examples are *Plasmodium falciparum, Plasmodium virax, Plasmodium ovale, Plasmodium malaria,* in humans and *Plasmodium knowlesii* in monkeys.

Malate synthase: An enzyme which functions in glyoxylate cycle.

Metabolic pathways: Both anabolism and catabolism consist of metabolic pathways in which an initial Compound A is converted to another B, then B is converted to C, C to D and so on until a final product is formed. In respiration, glucose is the initial compound, and $CO_2$ and $H_2O$ are the final products. There are approximately 50 distinct reactions in respiration but other metabolic pathways have fewer reactions. Herein the phrases "metabolic pathways" and "biochemical pathways" are used interchangeably.

Metabolism: Chemical reactions that make life possible. Thousands of such reactions occur constantly in each cell.

Microbes: Organisms which are visible only with use of a microscope. Some cause disease (are pathogenic).

Microbicidal: An agent (e.g., an antibiotic or antimicrobial compound) which kills microbes.

Mitochondria: An organelle responsible for the generation of energy.

Multilamellar: An adjective which refers to the multiple membranes within an organelle.

Noncompetitive inhibitors: Combine with enzymes at sites other than active site.

"Not involve": Are not a starting point, a component, or a product of the metabolic pathways described in relation to this invention.

NPMG: An inhibitor of EPSP synthase in the shikimate pathway.

Nucleic Acid: Deoxyribonucleic acid and ribonucleic acid molecules are constructed of a sugar phosphate backbone and nitrogen bases; important in the encoding, transcription and synthesis of proteins.

Oocyst: A life cycle stage of a parasite, e.g., *Toxoplasma gondii* that contains sporozoites. *T. gondii* sporozoites and oocysts form only in the cat intestine. This form of the parasite is able to persist in nature in warm, moist soil for up to a year and is highly infectious. Sporulation occurs several days after excretion of oocysts by members of the cat family (e.g., domestic cats or wild cats such as lions or tigers). Sporulation must occur before the oocyst becomes infectious.

Organelle: A structure within a cell. Examples are plastids, mitochondria, rhoptries, dense granules and micronemes.

Oxidoreductases (oxidases, reductases, dehydrogenases): Remove and add electrons or electrons and hydrogen. Oxidases transfer electrons or hydrogen to $O_2$ only.

Paraminobenzoic acid (PABA): A product of the shikimate pathway in plants.

Parasite: An organism which lives in or on a host for a period of time during at least one life-cycle stage.

Phagemid: Plasmid packaged within a filamentous phage particle.

Phosphoribosyl anthranilate isomerase: An enzyme which functions in tryptophan synthesis.

Plant-like: Present in algae and higher plants, but not or only rarely, or in unusual circumstances in animals.

*Plasmodium falciparum:* One species of Plasmodium which causes substantial human disease.

*Plasmodium knowlesii:* A species of Plasmodium which causes malaria in monkeys.

Plastid: A multilamellar organelle of plants, algae and Apicomplexan parasites which contains its own DNA separate from nuclear DNA. Plastids have been described in studies of Apicomplexan parasites which used electron micrographs (Siddall, 1992; Williamson et al., 1994; Wilson et al., 1991; Wilson et al., 1994; Wilson et al., 1996; Hackstein et al., 1995; McFadden et al., 1996).

Polymerases: Enzymes which link subunits (monomers) into a polymer such as RNA or DNA.

PPi phosphofructokinase Type I: An enzyme present in plants that functions in glycolysis and in a number of organisms regulates glycolysis. In plants and protozoans PPi, not ATP (as in animals) is utilized to synthesize Fru-1-6$P_2$ from Fru 6P. Activity is not stimulated in protozoa by Fru-2-6-$P_2$ (Peng & Mansour, 1992; Denton et al., 1996a,b).

Prephenate dehydratase (phenol 2-monoxygenase): An enzyme which functions in phenylalanine synthesis.

Prephenate dehydrogenase: An enzyme which functions in tyrosine synthesis.

Product: The end result of the action of an enzyme on a substrate.

Prosthetic group: Smaller organic nonprotein portion of an enzyme essential for catalytic activity. Flavin is an example.

Proteinases: Enzymes which are hydrolases which hydrolyze proteins (peptide bonds).

PS II: Important alternative means for producing energy within chloroplasts and apparently also described as being present in Apicomplexans.

Pyrimethamine: An inhibitor of the conversion of folate to folinic acid and thus an inhibitor of nucleic acids production effective against *Toxoplasma gondii.*

Recrudescence: Reactivation of the parasite *Toxoplasma gondii* from its latent phase.

Respiration: Major catabolic process that releases energy in all cells. It involves breakdown of sugars to $CO_2$ and $H_2O$.

Ribonucleases: Enzymes which are hydrolases which hydrolyze RNA (phosphate esters).

Salicylic Acid Metabolism in Plants: Salicylic acid is a plant hormone which promotes activity of cyanide resistant respiration.

SHAM: An inhibitor of the alternative oxidase.

Shikimate dehydrogenase: An enzyme which functions in chorismate synthesis.

Shikimate kinase: (shikimate 3-phosphotransferase) An enzyme which functions in chorismate synthesis.

Shikimate pathway A pathway that involves the conversion of shikimate to chorismate and subsequently the production of folate, aromatic amino acids, and ubiquinone. This pathway contains enzymes which lead to production of folic acid, ubiquinone, and aromatic amino acids. Folate, ubiquinone, and aromatic amino acids are products derived from this pathway in plants. There is sequential use of products of these pathways as reactants in subsequent enzymatically catalyzed reactions. For example, ubiquinone is an essential coenzyme for both conventional and alternative respiration. There are examples in plants, bacteria and fungi. (Bornemann et al., 1995; Marzabadi et al., 1996; Ozenberger et al., 1989; Shah et al., 1997; Gilchrist & Kosuge, 1980; Walsh et al, 1990; Weische & Leisterner, 1985; Green et al., 1992; Young et al., 1971).

Shikimate: The substrate for EPSP synthase.

Sporozoite: Another phase of the life cycle of *Toxoplasma gondii* which forms within the oocyst which is produced only within the cat's intestine. A highly infectious form of the parasite.

Stage specific: A characteristic of the parasite which is expressed or present only in a single life cycle stage or in some but not all life cycle stages.

Starch Degradation in Plants: 3 enzymes: α amylase (attack 1, 4 bonds of amylopectin (to maltose) and amylase (to dextrin). Many activated by Ca++. Located in chloroplasts. β amylase hydrolyzes starch to maltose; starch phosphorylase degrades starch beginning at nonreducing end. (Starch+H2PO4*≈glucose +–Phosphate) Only partially degrades amylopectin debranching enzymes hydroxy 1.6 branch linkage in amylopectin. Hexoses cannot move out of chloroplasts or amyloplasts thus must be converted to triose phosphate (3-PG aldehyde and dehydroxyacetone P), sucrose+UDP*≈fructose+UDP-glucose, *=sucrose synthase Starch Formation in Plants: Animals store starch as glycogen and plants store starch as amylose and amylopectin. Starch synthesis is dependent on starch synthase and branching Q enzymes. Mutations in genes encoding these enzymes lead to diminished production of starch. In addition, amylopectin synthesis predominates in plant mutants without UDP-glucose-starch glycosyl transferase whereas wild type plants with this enzyme make predominantly amylose and a smaller amount of amylopectin. In the mutant UDP-glucose-starch glycosyl transferase appears to be transcriptionally regulated. Amino acid motifs that target proteins to plant plastid organelles have been identified in UDP-glucose starch glycosyl transferase, as have other motifs that determine transit into plastids and mitochondria and these have been used to target the transported proteins in plants. Reactions include: ADPG+small amylose (in glucose)*→larger amylose (N+1 glucose units)+ADP,*=starch synthase K+. Branching or Q enzymes form branches in amylopectins between C6 of the main chain and C1of the branch chain. There are examples in plants (Abel et al., 1996; Van der Leif et al., 1991; Van der Steege et al., 1992).

Starch synthase: catalyzes reaction: ADPG+small amylose (n-glucose units)→larger amylose n+1glucose units+ADP and is activated by K+. Thus, sugars not starch accumulate in plants deficient in K+.

Starch: Major storage carbohydrate of plants, used for energy regeneration. Two types composed of D glucose connected by 1, 4 bonds which cause starch chains to coil into helices. The two types are amylose and amylopectin. Amylopectin is highly branched with the branches occurring between C-6 of a glucose in the main chain and C-1 of the first glucose in the branch chain (-1,6 bonds). Amyloses are smaller and have fewer branches. Amylopectin becomes purple or blue when stained with iodine-potassium-iodine solution. Amylopectin exhibits a purple red color. Control of starch formation is by K+ and a light activated sucrose phosphate synthase enzyme, invertase enzymes and the allosteric effect of fructose 2, 6 phiphosphate adenosine diphosphoglucose (ADPG) donates glucoses to form starch. Starch in amyloplasts is a principal respiratory substrate for storage organs.

Substrate reactant: Enzyme substrates have virtually identical functional groups that are capable of reacting. Specificity results from enzyme substrate combinations similar to a lock and key arrangement.

Substrate: The protein on which an enzyme acts that leads to the generation of a product.

Sucrose Formation Reactions in Plants:
UTP+glucose 1 phosphate≈UDPG+PPi
PPi+H$_2$O+2 Pi
UDPG+fructose 6 phosphate≈sucrose-6-phosphate+UDP
Sucrose-6-PHOSPHATE+H$_2$O→sucrose+Pi
UDP+ATP≈UTP+ADP
glucose-1-phosphate+fructose 6 phosphate+2 H$_2$O+ATP→sucrose 3Pi+ADP Sulfadiazine: An antimicrobial agent effective against *Toxoplasma gondii* which competes with para-aminobenzoic acid important in folate synthesis.

Sulfonylureas: Inhibitors of acetohydroxy acid synthase (an enzyme involved in the synthesis of branched chain amino acids, a pathway not or rarely present in animals).

Synergy: The effect of a plurality of inhibitors or antimicrobial agents which is greater than the additive effect would be combining effects of either used alone. Synergy occurs particularly when the action of an enzyme (which is inhibited) on a substrate leads to a product which is then the substrate for another enzyme which also is inhibited; that is, when the enzymes are in series or follow one another in a pathway. This effect occurs because the production of the first enzymatic reaction provides less substrate for the second reaction and thus amplifies the effect of the second inhibitor or antimicrobial agent. In contrast, an additive effect is when the effect of the compounds used together is simply the sum of the effects of each inhibitory compound used alone. This most often occurs when the pathways are in parallel, for example, when the effect on the first enzyme does not modify the effect of the second enzyme.

Tachyzoite: The rapidly replicating form of the parasite *Toxoplasma gondii*.

Theileria: An Apicomplexan parasite infecting cattle.

*Toxoplasma gondii*: A 3–5 micron, obligate, intracellular, protozoan parasite which is an Apicomplexan.

Toxoplasmosis: Disease due to *Toxoplasma gondii*.

Transit (translocation) peptide sequence: Amino acid sequence which results in transit into or out of an organelle. These have been described in plants (Volkner & Schatz, 1997; Theg & Scott, 1993). Herein we also call it a "metabolic pathway," although it is part of a component of a metabolic pathway or may function independently of a metabolic pathway.

Triazine: An inhibitor of PS II complex.

Tryptophan synthase alpha subunit: An enzyme which functions in tryptophan synthesis.

Tryptophan synthase beta subunit: An enzyme which functions in tryptophan synthesis.

Type I PPi phosphofructokinase is another enzyme present in plants and there is different substrate utilization by phosphofructokinases of animals.

UDP glucose starch glycosyl transferase: An enzyme involved in production of amylose in plants. The absence of this enzyme leads to starch formation as amylopectin rather than amylose.

USPA: Gene which encodes a universal stress protein. This has been described in *E. coli* (Nystrom & Neidhardt, 1992).

DOCUMENTS CITED

Abel, Gernot J. W., Springer, Franziska, Willmitzer, Lothar, Kossmann, Jens, (1996). The Plant Journal: 10(6) p. 981–991.

Askari, F. K. and McDonnell, W. M. (1 996). The New England Journal of Medicine, 334(5): 316–318.

Ausubel, F. M., Brent, R., Kingston, R. E., Moore, D. D., Seidman, J. G., Smith, J. A., and Struhl, K. (1987) Wiley Interscience, New York.

Avissar Y J, Beale S I (1990) J. Bacteriol, 712(3):1656–1659.

Bass H S, Njogu R M and Hill G C (1990) Exp. Parasitol. 70:486–489.

Baumann, R., et al. Antimicrob Ag Chemother 32:1119–1123, 1988.

Beckers, C. J. M., Roos, D. S., Donald, R. G. K., Luft, B. J., Schwab, J. C., Cao, Y., and Joiner, K. A. (1995) J. Clin. Invest. 95:367–376.

Blais, J., Gameau, V., and Chamberland, S. (1993) Antimicrob. Agents Chemother 37:1701–1703.

Bohne, W, Parmely S S, Yang S. and Gross (1996) Ed U. Gross, Current Topics in Micro. & Immu. 219:81–94.

Bohne, W., Heesemann, J., & Gross, U. (1993) Infection and Immunity 61, 1141–1145.

Bornemann, Stephen, Ramjee, Manoj K., Balasubramanian, Shankar, Abell, Chris, Coggins, John R., Lowe, David J., Thorneley, Roger N., (1995) The Journal of Biological Chemistry 270:39:22811–22815.

Boyer K and McLeod R (In Press, 1996) Toxoplasmosis. *Principles and Practice of Pediatric Infectious Diseases.*, 1$^{st}$ Edition, in S. Long, L Pickering L, C. Proeber. Churchill and Livingstone, First Ed. (In Press)

Brown C R, Estes R G, Beckmann E, Hunter C A, Remington J S, David C, Forman J and McLeod R (1995) Immunology, 85:419–28.

Buxton, D., Thomson, K. M., Maley, S., Wright, S. & Bos, H. J. (1993) Veterinary Record 133, 310–312.

Cate, J. H., Gooding, A. R., Podell, E., Zhou, K., Golden, B. L., Kundrot, C. E., Cech, T. R., Doudna, J. A. (1996), Science, 273:1678–1685.

Charbonnier, Jean-Baptiste et al. (1997), Science, 275:1140–1142.

Chatterjee, S. P., et al. Plant Mol Biol 26:285–290, 1994.

Chaudhuri, M. et al. (1996) Molec. Biochem. Parasitol 83:125–129.

Clarkson, Jr., Allen B., Bienen, E. Jay, Pollakis, Georgios, Grady, Robert W., (1989) Comp. Biochem. Physiol. 94B (2):245.

Craig III S P and A E Eakin, Parasitol Today, 13:6:238–241, 1997.

Current Protocols in Immunology (1996)

Day A., et al. Biochem J 161:677–685, 1977.

Denton H, Brown M A, Roberts C W, Alexander J, McDonald V, Thong K-W & Coombs, G H (1996a) Molecular and Biochemical Parasitology 76:23–29.

Denton H, Roberts C W, Alexander J, Thong K-W & Coombs G H (1996b) *Molecular and Biochemical Parasitology* FEMS Microbiological Letters. 137:103–108.

Dieckmann A. and A. Jung. Biochem Parasitol 19:143–147, 1986.

Donald R G K, Carter D, Ullman B, Roos D S. (1996) J. of Biol. Chem. 271.

Donald R G K, and D S Roos (1993) Proc. Natl. Acad. Sci. 90:11703–11707.

Donald R G K, and D S Roos (1994) Mol and Biol Parasitol 63:243–253.

Donald R G K and D S Roos (1995) Proc. Natl. Acad. Sci. 92:5749–5753.

Dubremetz J F and Soete M (1996) Ed U. Gross, Current Topics in Micro. & Immu. 219:76–80.

Edwards, L. S., et al. Biochem Soc Tran 22:805, 1994.

Eisenthal, R. and A. Comish-Bowden. J Biol Chem 273:5500–5505, 1998.

Elich, Tedd D., Lagarias, J. Clark (1988) Plant Physiol. 88, p. 747–751.

Elliott T, Avissar Y J, Rhie G and Beale S I (1990) J. Bacteriol. 172:7071–7084.

El-Waziry, A. M., et al. Curr Microbiol 33:306–311, 1996.

Fichera, M. M., Bhopale, M. K., and Roos, D. S. (1995) Antimicrob. Agents Chemother. 39: 1530–1537.

Fry, M. and Beesley, J. E. (1991) Parasitology, 102:17–26.

Gerhart F., et al. J Med Chem 33:2157–2167, 1990.

Gilchrist D. G., Kosuge T (1980) Chapter 13. The Biochemistry of Plants, Vol. 5, Academic Press, Inc.

Girodeau, J. M., et al. J Med Chem 29:1023–1030, 1986.

Gough S P, Kannangara C G, Bock K (1989) Carlsberg Res. Commun. 54:99–108.

Green, Jacalyn M., Merkel, William K., Nichols, Brian P. (1992) Journal of Bacteriology 174 (16):5317–5323.

Grimm B (1990) Proc. Natl. Acad. Sci. 87:4169–4173.

Grula, John W., Hudspeth, Richard L., Hobbs, Susan L., Anderson, David M. (1995) Plant Molecular Biology 28:837–846.

Hackstein J H P, Mackenstedt U, Melhorn H, Schubert H and Leunissen J A M (1995) Parasitol Res. 81:207–216.

Higgin W., et al. Eur J Biochem 186:137–143, 1989.

Hill G C (1976) Biochimica Biophysica Acta 456:149–193.

Holfels E, McAuley J, Mack D, Milhous W, and McLeod R (1994) Antimicrob. Ag. and Chemother. 38(6):1392–1396.

Howe G, Mets L, Merchant S (1995) Mol. Gen. Genet. 246:156–165.

Jahn D, Chen M-W, Söll D (1991) J. Biol. Chem. 266:139–150.

Kahn F R, Saleemuddin M, Siddiqi M and McFadden B A (1977) Arch. Biochem. Biophys. 183:13–23.

Kasper L H, Crabb J., Pfefferkorn, E. R. (1983) J. Immunol. 130:2407–2412.

Kemp, B. E., Rylatt, D. B., Bundesen, P. G., Doherty, R. R., McPhee, D. A., Stapleton, D., Cottis, L. E., Wilson, K., John, M. A ., Khan, J. M. et al. (1988) Science 241(4871):1352–1354.

Khoshnoodi, Jamshid, Blennow, Andreas, EK, Bo, Rask, Lars, Larsson, Hakan (1996) Eur. J. Biochem., 242:148–155.

Kirisits, M. J., Mui, E., and McLeod, R., Fourth International Biennial *Toxoplasma* Conference, Drymen, Scotland, 1996.

Klee H J, Muskopf Y M, Gassa C S (1987) Molec. Gen. Genet. 210:437–442.

Klösgen R B and Well J-H (1991) Mol. Gen. Genet 225:297–304.

Kohler S, Delwiche C F, Denny P W, Tilney L G, Webster P, Wilson P J M, Palmer J D, Roos D S. (1997) Science 275:1485–1489.

Kortstee, Anne J., Vermeesch, Angela M. S., deVries, Beja J., Jacobson, Evert, Visser, Richard G. F. (1996) The Plant Journal 10(1), 83–90.

Kumar, A. M. and Söll, D. (1992) Proc. Natl. Acad. Sci. USA 89:10842–10846.

Kuriki, Takashi, Guan, Hanping, Sivak, Mirta, Preiss, Jack (1996) Journal of Protein Chemistry, 15 (3):305–313.

Lam K., et al. J Biol Chem 263(24):11814–11819, 1988.

Lambers H. (1990) In: Plant Physiology, Biochemistry & Molecular Biology. Dennis D. T., and Turpin, D. H. (eds) John wiley & Sons, New York, pp. 124–143.

Li Q, Ritzel R G, McLean, L T, McIntosh L, Ko T, Bertrand H and Nargang F E (1996) Genetics 142:129–140.

Mack D and R McLeod (1984) Antimicrob. Ag. Chemother. 26:26–30.

Mack D, R McLeod and B Stark, Eur J Protistol, 32:96–103, 1996.

Mahal L K, Yarema K J, Bertozzi, C R (1997) Science 276:1125–8.

Maloy S R, Bohlander and Nunn W D (1980) J. Bacteriol. 143:720–725.

Maloy S R and Munn W P (1982) J. Bacteriol. 149:173–180.

Marzabadi, Mohammad R., Gruys, Kenneth J., Pansegrau, Paul D., Walker, Mark C., Yuen, Henry K., Sikorski, James A. (1996) Biochemistry 35:4199–4210.

Matters G L and Beale, S I (1995) Plant Mol. Biol. 27:607–617.

McAuley J, et al., Clin Inf Dis, 18:38–72, 1994.

McFadden G I; Keith, M E; Munholland J M, Lang Unnasch N (1996) Nature 381:482.

McIntosh L. (1994) Plant Physiol. 329:781–786.

McLeod R, Cohen H, and R Estes (1984) JID 149:234–244.

McLeod R, J K Frenkel, R G Estes, D G Mack, P Eisenhauer and G Gibori. (1 988) J. Immunol. 140:1632–1637.

McLeod R, D Mack and C Brown. (1991) Exper. Parasitol. 72:109–121.

McLeod R, D Mack, R Foss, K Boyer, S Withers, S Levin and J Hubbel. (1992) Antimicrob. Ag. Chemother. 36:1040–1048.

Mets, L. and A. Thiel, in P. Bger & G. Sandmann, eds, (1989) Target Sites of Herbicide Action. Biochemistry and Genetic Control of the Photosystem-II Herbicide Target Site. CRC Press, Boca Raton, Fla., pp. 1–24.

Milhous W. et al. (1985) Antimicrobial & Chemo. Therapies. 27:525–530.

Mineo J R, R McLeod, D Mack, J Smith, I A Kahn, K H Ely and L. Kasper. (1993) J. Immunol. 50:3951–3964.

Morell, Matthew K., Blennow, Andreas, Kosar-Hashemi, Behjat, Samuel, Michael S. (1997) Plant Physiol. 113:201–208.

Mousdale, D. And Coggins, J. (1985) L. Planta 163:241–249.

Murphey, A. D., et al. Exp Parasitol 87:112–120, 1997.

Nichols, Brian P., Green, Jacalyn M. (1992) Journal of Bacteriology 174 (16):5309.

Nystrom, Thomas, Neidhardt, Frederick (1993) J. Bacteriol. 175:3949–3956.

Odoula et al. (1988) Exp. Parasit. 66: 86–95.

Ott, Karl-Heinz, Kwagh, Jae-Gyu, Stockton, Gerald W., Sidorov, Vladimir, Kakefuda, Genichi (1996) J. Mol. Biol. 263, 359–368.

Ozenberger, Bradley A., Brickman, Timothy J., McIntosh Mark A.(1989) Journal of Bacteriology 171(2): 775–783.

Pace, Norman R. (1992) Science, Vol. 256, p. 1402.

Peng, Zao-Yuan, Mansour, Tag E. (1992) Molecular and Biochemical Parasitology 54:223.

Pfefferkorn, E. R. and Borotz, S. E. (1994) Antimicrob. Agents Chemother. 38:31–37.

Pfefferkon, E. R., Nothnagel, R. F., and Borotz, S. E. (1992) Antimicrob. Agents Chemother. 36:1091–1096.

Pollakis, Georgios, Grady, Robert W., Dieck, Harold A., and Clarkson, Jr., Allen B. (1995) Biochemical Pharmacology, 50 (8): 1207.

Pukrittaykamee, S., Viravan, C., Charoenlarp, P., Yeamput, C., Wilson, R. J. M., and White, N. J. (1994) Antimicrob. Agents Chemother, 38:511–514.

Rhoads, David M., McIntosh, Lee (1992) The Plant Cell 4:1131–1132.

Roberts, C. W., Cruickshank, S. M., Alexander, J.(1995) Infection and Immunity 63:2549–2555.

Roberts, C. and McLeod, R. (1996) *Toxoplasma gondii.* In Infectious Diseases in Medicine and Surgery. J Bartlett, S. Gorbach, N Blacklow (Eds.), Philadelphia, W B Saunders Co., In Press.

Roberts F., et al. Nature (In Press, Jun. 25, 1998).

Robson, K. J. H., Gamble, Y., and Acharya, K. R. (1993) Philos. Trans. R. Soc. Lond series B 340:39–53.

Roos, D. S., (1996) Ed. U. Gross, *Current Topics in Micro. & Immu.* V. 219, Springer.

Roush W. (1 997) Science 276:1192–3.

Saleh F., et al. J Gen Microbiol 96: 253–261, 1976.

Sangwan, I. and O'Brian, M. R. (1993) Plant Physiol. 102:829–834.

Schwab, J. C., Cao, Y., Slowik, M. R., and Joiner, K. A. (1994) Antirnicrob. Agents Chemother. 38:1620–1627.

Shah, A., Font, J. L. Miller, M. J. Ream, J. E., Walker, M. C., Sikorski, J. A. (1997) Bioorganic and Medicinal Chemistry 5:323–334.

Sibley, L. D. and Krahenbuhl, L. J. (1988) Eur. J. Cell Biol. 47:81–87.

Siddall, M. E. (1992) Parasitol Today 8:90–91.

Soete M. Camus D. and Dubremetz J. F. (1994) Exp. Parasitol. 78:361–370.

Strath, M., Scott-Finnigan, T., Gardner, M., Williamson, D. H., and Wilson, R. J. M. (1993) Trans. R. Soc. Trop. Med. Hyg. 87:211–216.

Surolia, N. and Padmanaban, G. (1992) Biochem. Biophys. Res. Comm. 187:744–750.

Theg S. and Scott S. V. (1993) Trends in Cell Biol. Vol 3: Elsevier Science Publishers Ltd. (Section of Plant Biology, Univ. of CA, Davis, Calif.).

Thompson, J. D. Higgins, D. G. and Gibson, T. J. (1994) Nucleic Acids Research, 22:4673–4680.

Tine, John A. et al. (1996) Infection and Immunity, 3833–3844.

Tolbert, N. E. (1980) The Biochemistry of Plants, Vol. 1: Academic Press, Inc.

Tomovo, S. and Boothroyd J. C. (1995) Int. J. of Parasitol 25:1293–1299.

Ulmer, Jeffrey B., Donnelly, John J., Liu, Margaret A. (1996) DNA Vaccines Promising: A New Approach to Inducing Protective Immunity. According to experiments with several animal species, antigen-encoding DNA can elicit protective immune responses, ASM News, Vol. 62, No. 9 pp. 476–479.

Van der Leif, Feilke R., Visser, Richard G. F., Ponstein, Anne S., Jacobsen, Evert, Feenstra, Will J. (1991) Mol. Gen. Genet. 228:240–248.

Van der Steege, Gerrit, Nieboer, Maarten, Swaving, Jelto, Tempelaar, M. J. (1992) Plant Molecular Biol. 20: 19–30.

Volker H, Schatz G. (1997) Cell Biology 7:103 –106.

Walsh, Christopher T., Liu, Jun, Rusnak, Frank, Sakaitani, Masahiro (1990) Chem. Rev. 90:1105–1129.

Weinstein D. and Beale S. I. (1985) Arch. Biochem. Biophys. 237:454–464.

Weir, A. N., et al. Anal Biohem 180(2):298–302, 1989.

Weische, Alfons, Leistner, Eckhard (1985) Biosynthesis, Tetrahedron Letters 26 (12):1487–1490.

Weiss L. M., LaPlace D., Tanowitz H. B. and Witner M. (1992) J. Inf Dis. 166:213–215.

Williamson, D. H., Gardner, M. J., Preiser, P., Moore, D. J., Rangarchari, K., and Wilson, R. J. M. (1994) Mol. Gen. Genet. 243:249–252.

Wilson R. J. M., Gardner M. J., Feagin J. E., Williamson D. H.(1991) Parasitol. Today 7:134–136.

Wilson, R. J. M., Williamson, D. H., and Preiser, P. (1994) Infectious Agents and Disease 3:29–37.

Wilson R J, Denny P W, Preiser P R, Rangachari K, Roberts K, Roy A, Whyte A, Strath M, Moore D J, Moore P W , Williamson D H (1996) J. Mol. Biol. 261:2:155–72.

Young, I G., Langman, L., Luke, R. K., Gibson, F. (1971) Journal of Bacteriology, p. 51–57.

We claim:

1. A method for producing a composition that interferes with the growth or survival of an Apicomplexan parasite, the method comprising:

(a) obtaining an enzyme of a plant-like metabolic pathway in an Apicomplexan parasite, wherein the pathway does not involve the psbA gene or PPi phosphofructokinase, is not encoded by the plastid genome, and is not operative in animals;

(b) developing an inhibitor of the enzyme or a fragment of the enzyme;

(c) preparing a composition comprising the inhibitor; and (d) contacting the Apicomplexan parasite with an effective amount of the composition, said effective amount being that which interferes with growth or survival of the parasite.

2. The method of claim 1, wherein the plant-like metabolic pathway is selected from the group consisting of the plant-like metabolic pathway for:
(a) synthesis of heme from glutamate and tRNA glu by the plant-like heme synthesis (5 carbon) pathway;
(b) synthesis of C4 acids by the breakdown of lipids into fatty acids and then acetyl CoA, and their use in the glyoxylate cycle;
(c) synthesis of chorismate from phosphoenolpyruvate and erythrose 4 phosphate by the shikimate pathway;
(d) synthesis of tetrahydrofolate from chorismate by the shikimate pathway;
(e) synthesis of ubiquinone from chorismate by the shikimate pathway;
(f) electron transport through the alternative pathway with use of the alternative oxidase; and
(g) transport of proteins into or out of an organelle through the use of a transit peptide.

3. The method of claim 1, wherein the plant-like metabolic pathway is selected from the group consisting of the plant-like metabolic pathway for:
(a) synthesis of aromatic amino acids (phenylalanine, tyrosine and tryptophan) from chorismate by the shikimate pathway;
(b) synthesis of the menaquinone, enterobactin and vitamins E and K1 from chorismate by the shikimate pathway;
(c) synthesis of the branched chain amino acids from pyruvate and α-ketoburyrate by the plant-like branched chain amino acid synthesis pathway;
(d) synthesis of the essential amino acids, not synthesized by animals, and including histidine, threonine, lysine and methionine by the use of plant-like amino acid synthases;
(e) synthesis of linoleneic and linoleic acid and other fatty acids;
(f) synthesis of amylose and amylopectin with starch synthases and branching enzymes and their degradation;
(g) synthesis of auxin growth regulators from indoleacetic acid derived from chorismate; and
(h) synthesis of isoprenoids such as giberellins and abscisic acid by the mevalonic acid to giberellin pathway.

4. The method of claim 1, wherein the composition that interferes with growth or survival comprises a plurality of inhibitors.

5. The method of claim 4, wherein the plurality of inhibitors exhibits a synergistic effect.

6. The method of claim 4, wherein the composition that interferes with growth or survival is selected from the group consisting of gabaculine and sulfadiazine, NPMG and gabaculine, SHAM and gabaculine, pyrimethamine and NPMG, sulfadiazine and NPMG, cycloguanil and NPMG, 8-OH-quinoline and NPMG, and SHAM and NPMG.

7. The method of claim 1, wherein the inhibitor acts on a latent bradyzoite form of the parasite.

8. The method of claim 1, wherein the composition interferes with more than one component of the pathway.

9. The method of claim 1, wherein the component of the pathway is a molecule having an amino acid sequence selected from the group consisting of sequences identified as SEQ ID NO: 2 or 4 or fragment thereof.

* * * * *

SEQUENCE LISTING (1) GENERAL INFORMATION:

(iii) NUMBER OF SEQUENCES: 44

(2) INFORMATION FOR SEQ ID NO:1:

(i) SEQUENCE CHARACTERISTICS:
      (A) LENGTH: 2312 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 162..1769

(xi) SEQUENCE DESCRIPTION: SEQ ID NO:1:

```
CTCATCTTCT CGGTTTCACT TTTCTTTGAG TGCCTGTGTG AGAGACGGTC GTCGCAACAA      60

GAATCTCCTC CGCTCACGCC TTTCCTCACA GTCCTGTTTT TCCTCCAGCT GTCACACATC     120

CCGCTCGTTC CGCTGCATCT CCTCACATTT CTTGCAGTCA G ATG TCT TCC TAT        173
                                              Met Ser Ser Tyr
```

```
GGA GCC GCT CTG CGC ATA CAC ACT TTC GGT GAA TCT CAC GGC TCA GCC      221
Gly Ala Ala Leu Arg Ile His Thr Phe Gly Glu Ser His Gly Ser Ala
  5                  10                  15                  20

GTT GGG TGT ATA ATC GAC GGG CTG CCT CCT CGC CTC CCT CTT TCT GTC      269
Val Gly Cys Ile Ile Asp Gly Leu Pro Pro Arg Leu Pro Leu Ser Val
                 25                  30                  35

GAA GAT GTT CAG CCT CAA TTA AAT CGC AGA AGA CCC GGC CAA GGG CCT      317
Glu Asp Val Gln Pro Gln Leu Asn Arg Arg Arg Pro Gly Gln Gly Pro
             40                  45                  50

CTC TCG ACG CAG CGG AGA GAG AAA GAT CGA GTC AAC ATA CTC TCC GGT      365
Leu Ser Thr Gln Arg Arg Glu Lys Asp Arg Val Asn Ile Leu Ser Gly
         55                  60                  65

GTT GAA GAC GGA TAT ACA CTC GGT ACT CCC CTG GCG ATG CTC GTC TGG      413
Val Glu Asp Gly Tyr Thr Leu Gly Thr Pro Leu Ala Met Leu Val Trp
 70                  75                  80

AAT GAA GAC CGG CGG CCC CAG GAC TAC CAC GCC CTC GCG ACA GTC CCG      461
Asn Glu Asp Arg Arg Pro Gln Asp Tyr His Ala Leu Ala Thr Val Pro
 85                  90                  95                 100

CGT CCA GGT CAC GGG GAT TTC ACC TAC CAT GCA AAG TAC CAC ATT CAC      509
Arg Pro Gly His Gly Asp Phe Thr Tyr His Ala Lys Tyr His Ile His
                105                 110                 115

GCG AAA AGC GGG GGC GGT CGG AGC AGC GCG CGG GAG ACT TTG GCG CGC      557
Ala Lys Ser Gly Gly Gly Arg Ser Ser Ala Arg Glu Thr Leu Ala Arg
            120                 125                 130

GTC GCC GCT GGA GCA GTC GTT GAG AAG TGG CTA GGC ATG CAC TAC GGC      605
Val Ala Ala Gly Ala Val Val Glu Lys Trp Leu Gly Met His Tyr Gly
        135                 140                 145

ACC AGC TTC ACA GCT TGG GTC TGT CAG GTT GGT GAT GTC TCT GTG CCC      653
Thr Ser Phe Thr Ala Trp Val Cys Gln Val Gly Asp Val Ser Val Pro
    150                 155                 160

CGA TCG CTC CGA AGA AAG TGG GAG CGG CAG CCG CCA ACT CGC CAA GAC      701
Arg Ser Leu Arg Arg Lys Trp Glu Arg Gln Pro Pro Thr Arg Gln Asp
165                 170                 175                 180

GTC GAT CGC CTT GGC GTG GTC CGC GTG AGC CCA GAT GGA ACC ACA TTT      749
Val Asp Arg Leu Gly Val Val Arg Val Ser Pro Asp Gly Thr Thr Phe
                185                 190                 195

CTC GAC GCG AAC AAC CGC CTT TAC GAC GAG CGA GGA GAG GAA CTC GTC      797
Leu Asp Ala Asn Asn Arg Leu Tyr Asp Glu Arg Gly Glu Glu Leu Val
            200                 205                 210

GAG GAG GAA GAC AAA GCC AGG CGT CGG CTT CTT TTC GGA GTC GAC AAC      845
Glu Glu Glu Asp Lys Ala Arg Arg Arg Leu Leu Phe Gly Val Asp Asn
        215                 220                 225

CCG ACG CCA GGA GAA ACA GTG ATT GAG ACC AGG TGC CCG TGC CCC TCC      893
Pro Thr Pro Gly Glu Thr Val Ile Glu Thr Arg Cys Pro Cys Pro Ser
    230                 235                 240

ACA GCT GTT CGC ATG GCT GTG AAA ATC AAC CAG ACC CGA TCT CTG GGC      941
Thr Ala Val Arg Met Ala Val Lys Ile Asn Gln Thr Arg Ser Leu Gly
245                 250                 255                 260

GAT TCG ATT GGC GGA TGC ATC TCC GGT GCA ATC GTG CGG CCA CCG CTG      989
Asp Ser Ile Gly Gly Cys Ile Ser Gly Ala Ile Val Arg Pro Pro Leu
                265                 270                 275

GGC CTC GGC GAG CCG TGT TTC GAC AAA GTG GAG GCG GAG CTG GCG AAG     1037
Gly Leu Gly Glu Pro Cys Phe Asp Lys Val Glu Ala Glu Leu Ala Lys
            280                 285                 290

GCG ATG ATG TCG CTC CCT GCT ACG AAA GGG TTT GAG ATT GGC CAG GGC     1085
Ala Met Met Ser Leu Pro Ala Thr Lys Gly Phe Glu Ile Gly Gln Gly
        295                 300                 305

TTT GCG AGT GTC ACG TTG CGA GGC AGC GAG CAC AAC GAC CGC TTC ATT     1133
Phe Ala Ser Val Thr Leu Arg Gly Ser Glu His Asn Asp Arg Phe Ile
    310                 315                 320
```

```
CCC TTC GAG AGA GCG TCG TGT TCA TTC TCG GAA TCA GCC GCG AGC ACG    1181
Pro Phe Glu Arg Ala Ser Cys Ser Phe Ser Glu Ser Ala Ala Ser Thr
325                 330                 335                 340

ATC AAG CAT GAA AGA GAT GGG TGT TCA GCT GCT ACA CTC TCA CGG GAG    1229
Ile Lys His Glu Arg Asp Gly Cys Ser Ala Ala Thr Leu Ser Arg Glu
                345                 350                 355

CGA GCG AGT GAC GGT AGA ACA ACT TCT CGA CAT GAA GAG GAG GTG GAA    1277
Arg Ala Ser Asp Gly Arg Thr Thr Ser Arg His Glu Glu Glu Val Glu
            360                 365                 370

AGG GGG CGG GAG CGC ATA CAG CGC GAT ACC CTC CAT GTT ACT GGT GTA    1325
Arg Gly Arg Glu Arg Ile Gln Arg Asp Thr Leu His Val Thr Gly Val
        375                 380                 385

GAT CAG CAA AAC GGC AAC TCC GAA GAT TCA GTT CGA TAC ACT TCC AAA    1373
Asp Gln Gln Asn Gly Asn Ser Glu Asp Ser Val Arg Tyr Thr Ser Lys
    390                 395                 400

TCA GAG GCG TCC ATC ACA AGG CTG TCG GGA AAT GCT GCC TCT GGA GGT    1421
Ser Glu Ala Ser Ile Thr Arg Leu Ser Gly Asn Ala Ala Ser Gly Gly
405                 410                 415                 420

GCT CCA GTC TGC CGC ATT CCA CTA GGC GAG GGA GTA CGG ATC AGG TGT    1469
Ala Pro Val Cys Arg Ile Pro Leu Gly Glu Gly Val Arg Ile Arg Cys
                425                 430                 435

GGA AGC AAC AAC GCT GGT GGA ACG CTC GCA GGC ATT ACA TCA GGA GAG    1517
Gly Ser Asn Asn Ala Gly Gly Thr Leu Ala Gly Ile Thr Ser Gly Glu
                440                 445                 450

AAC ATT TTT TTT CGG GTG GCC TTC AAG CCT GTT TCT TCC ATC GGC TTG    1565
Asn Ile Phe Phe Arg Val Ala Phe Lys Pro Val Ser Ser Ile Gly Leu
            455                 460                 465

GAA CAA GAA ACT GCA GAC TTT GCT GGT GAA ATG AAC CAG CTA GCT GTG    1613
Glu Gln Glu Thr Ala Asp Phe Ala Gly Glu Met Asn Gln Leu Ala Val
        470                 475                 480

AAA GGC CGC CAC GAT CCC TGC GTC CTT CCG CGA GCC CCT CCT CTG GTT    1661
Lys Gly Arg His Asp Pro Cys Val Leu Pro Arg Ala Pro Pro Leu Val
485                 490                 495                 500

GAG AGC ATG GCT GCC CTT GTG ATT GGC GAT CTG TGC CTC CGC CAG CGC    1709
Glu Ser Met Ala Ala Leu Val Ile Gly Asp Leu Cys Leu Arg Gln Arg
                505                 510                 515

GCC CGG GAA GGG CCG CAC CCC CTT CTC GTC CTT CCT CAA CAC AGT GGT    1757
Ala Arg Glu Gly Pro His Pro Leu Leu Val Leu Pro Gln His Ser Gly
                520                 525                 530

TGC CCA TCT TGC TGAGCTCTAC CTTGTTCCAA AAACTTGTGC ATACGGGGTA        1809
Cys Pro Ser Cys
            535

CACCAGGTTC CTCACAAGGA GAATCGTGAG GCGGTGACTG GCCAGCGCCA CAGATTGCTG  1869

TTCATGCACA AGAAAGAAAA CAGCGCATTT CCGCCACAAC CCAGCTGCAT GAAGTTGCTG  1929

GATATCGTTC CGGCGGTGCT CGGCCTTCTT CTCTACGCTC GCGATGATAC GTCGCGAGCT  1989

TCATCAAGCT CCTTTTGCAT TGTTAGTGGC TCCCAACAGA ACCCTTTGTG GAAGGGAATC  2049

TGGTCTCACG CTTGCAGGAG AGAGTTCGCC TTTGTTCACG AAATAACGAA GCCAAGCAGC  2109

TCAGTTGCAT TCAGCCTGCA CACAGTTGCA TTCAGCCTGC ACACTAAACA CGGGCGAAAT  2169

CGTCGCGTGA TATGTAGTTC TTCGGTTGTC ACGGTGATTG TCGTCGTGTT TGAACAACTA  2229

AACGTTTCTA ATGCTGGATC TTAAAAAAAA AAAAAAAAA AAAAAAAAAA AAAAAAAAAA  2289

AAAAAAAAAA AAAAAAAAAA AAA                                         2312
```

(2) INFORMATION FOR SEQ ID NO:2:

(i) SEQUENCE CHARACTERISTICS:

(A) LENGTH: 536 amino acids
(B) TYPE: amino acid
(D) TOPOLOGY: linear (ii) MOLECULE TYPE: protein (xi) SEQUENCE DESCRIPTION: SEQ ID NO:2:

```
Met Ser Ser Tyr Gly Ala Ala Leu Arg Ile His Thr Phe Gly Glu Ser
  1               5                  10                  15

His Gly Ser Ala Val Gly Cys Ile Ile Asp Gly Leu Pro Pro Arg Leu
             20                  25                  30

Pro Leu Ser Val Glu Asp Val Gln Pro Gln Leu Asn Arg Arg Arg Pro
         35                  40                  45

Gly Gln Gly Pro Leu Ser Thr Gln Arg Arg Glu Lys Asp Arg Val Asn
     50                  55                  60

Ile Leu Ser Gly Val Glu Asp Gly Tyr Thr Leu Gly Thr Pro Leu Ala
 65                  70                  75                  80

Met Leu Val Trp Asn Glu Asp Arg Arg Pro Gln Asp Tyr His Ala Leu
                 85                  90                  95

Ala Thr Val Pro Arg Pro Gly His Gly Asp Phe Thr Tyr His Ala Lys
            100                 105                 110

Tyr His Ile His Ala Lys Ser Gly Gly Arg Ser Ser Ala Arg Glu
        115                 120                 125

Thr Leu Ala Arg Val Ala Ala Gly Ala Val Val Glu Lys Trp Leu Gly
130                 135                 140

Met His Tyr Gly Thr Ser Phe Thr Ala Trp Val Cys Gln Val Gly Asp
145                 150                 155                 160

Val Ser Val Pro Arg Ser Leu Arg Arg Lys Trp Glu Arg Gln Pro Pro
                165                 170                 175

Thr Arg Gln Asp Val Asp Arg Leu Gly Val Val Arg Val Ser Pro Asp
            180                 185                 190

Gly Thr Thr Phe Leu Asp Ala Asn Asn Arg Leu Tyr Asp Glu Arg Gly
        195                 200                 205

Glu Glu Leu Val Glu Glu Asp Lys Ala Arg Arg Arg Leu Leu Phe
210                 215                 220

Gly Val Asp Asn Pro Thr Pro Gly Glu Thr Val Ile Glu Thr Arg Cys
225                 230                 235                 240

Pro Cys Pro Ser Thr Ala Val Arg Met Ala Val Lys Ile Asn Gln Thr
                245                 250                 255

Arg Ser Leu Gly Asp Ser Ile Gly Gly Cys Ile Ser Gly Ala Ile Val
            260                 265                 270

Arg Pro Pro Leu Gly Leu Gly Glu Pro Cys Phe Asp Lys Val Glu Ala
        275                 280                 285

Glu Leu Ala Lys Ala Met Met Ser Leu Pro Ala Thr Lys Gly Phe Glu
290                 295                 300

Ile Gly Gln Gly Phe Ala Ser Val Thr Leu Arg Gly Ser Glu His Asn
305                 310                 315                 320

Asp Arg Phe Ile Pro Phe Glu Arg Ala Ser Cys Ser Phe Ser Glu Ser
                325                 330                 335

Ala Ala Ser Thr Ile Lys His Gly Arg Asp Gly Cys Ser Ala Ala Thr
            340                 345                 350

Leu Ser Arg Glu Arg Ala Ser Asp Gly Arg Thr Thr Ser Arg His Glu
        355                 360                 365

Glu Glu Val Glu Arg Gly Arg Glu Arg Ile Gln Arg Asp Thr Leu His
370                 375                 380
```

```
Val Thr Gly Val Asp Gln Gln Asn Gly Asn Ser Glu Asp Ser Val Arg
385                 390                 395                 400

Tyr Thr Ser Lys Ser Glu Ala Ser Ile Thr Arg Leu Ser Gly Asn Ala
            405                 410                 415

Ala Ser Gly Gly Ala Pro Val Cys Arg Ile Pro Leu Gly Glu Gly Val
            420                 425                 430

Arg Ile Arg Cys Gly Ser Asn Asn Ala Gly Gly Thr Leu Ala Gly Ile
            435                 440                 445

Thr Ser Gly Glu Asn Ile Phe Phe Arg Val Ala Phe Lys Pro Val Ser
450                 455                 460

Ser Ile Gly Leu Glu Gln Glu Thr Ala Asp Phe Ala Gly Glu Met Asn
465                 470                 475                 480

Gln Leu Ala Val Lys Gly Arg His Asp Pro Cys Val Leu Pro Arg Ala
            485                 490                 495

Pro Pro Leu Val Glu Ser Met Ala Ala Leu Val Ile Gly Asp Leu Cys
            500                 505                 510

Leu Arg Gln Arg Ala Arg Glu Gly Pro His Pro Leu Leu Val Leu Pro
            515                 520                 525

Gln His Ser Gly Cys Pro Ser Cys
530                 535

(2) INFORMATION FOR SEQ ID NO:3:

(i) SEQUENCE CHARACTERISTICS:
        (A) LENGTH: 1837 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 105..1685

(xi) SEQUENCE DESCRIPTION: SEQ ID NO:3:

CTCGAGTTTT TTTTTTTTTT TTTTTTTGA TACATAATAA TCAAGAGTTC TTTATACTAA      60

CAGACTTATT TAATGTATTA TTTTTGGTAA ACAAAAAAAA CATT ATG AGC ACA TAT     116
                                                 Met Ser Thr Tyr
                                                  1

GGG ACT TTA TTA AAA GTA ACA TCC TAC GGA GAA AGT CAT GGG AAA GCT     164
Gly Thr Leu Leu Lys Val Thr Ser Tyr Gly Glu Ser His Gly Lys Ala
 5                  10                  15                  20

ATT GGG TGT GTG ATC GAT GGG TTT TTA TCC AAT ATA GAA ATA AAT TTT     212
Ile Gly Cys Val Ile Asp Gly Phe Leu Ser Asn Ile Glu Ile Asn Phe
                 25                  30                  35

GAT TTA ATA CAA AAA CAA TTA GAT AGA CGA AGA CCA AAT CAA TCA AAA     260
Asp Leu Ile Gln Lys Gln Leu Asp Arg Arg Arg Pro Asn Gln Ser Lys
             40                  45                  50

CTA ACT AGT AAT AGA AAC GAA AAA GAT AAA CTT GTT ATA CTT TCA GGA     308
Leu Thr Ser Asn Arg Asn Glu Lys Asp Lys Leu Val Ile Leu Ser Gly
         55                  60                  65

TTT GAT GAA AAT AAA ACA TTA GGT ACA CCT ATT ACA TTT TTA ATA TAT     356
Phe Asp Glu Asn Lys Thr Leu Gly Thr Pro Ile Thr Phe Leu Ile Tyr
 70                  75                  80

AAT GAA GAT ATT AAA AAA GAA GAT TAT AAT TCT TTT ATA AAT ATT CCT     404
Asn Glu Asp Ile Lys Lys Glu Asp Tyr Asn Ser Phe Ile Asn Ile Pro
         85                  90                  95                 100

AGA CCA GGA CAT GGA GAT TAT ACC TAT TTT ATG AAA TAT CAT GTT AAA     452
```

```
                Arg Pro Gly His Gly Asp Tyr Thr Tyr Phe Met Lys Tyr His Val Lys
                            105                 110                 115

AAT AAA AGT GGA AGT AGT AGA TTT TCT GGA AGA GAA ACA GCC ACA AGA          500
Asn Lys Ser Gly Ser Ser Arg Phe Ser Gly Arg Glu Thr Ala Thr Arg
            120                 125                 130

GTT GCT GCT GGG GCG TGC ATT GAA CAA TGG CTT TAT AAA TCT TAT AAT          548
Val Ala Ala Gly Ala Cys Ile Glu Gln Trp Leu Tyr Lys Ser Tyr Asn
            135                 140                 145

TGT TCT ATT GTT AGT TAT GTA CAT TCA GTT GGG AAT ATA AAG ATA CCT          596
Cys Ser Ile Val Ser Tyr Val His Ser Val Gly Asn Ile Lys Ile Pro
150                 155                 160

GAA CAA GTC AGC AAA GAA TTG GAA AAT AAA AAT CCA CCC TCA AGA GAT          644
Glu Gln Val Ser Lys Glu Leu Glu Asn Lys Asn Pro Pro Ser Arg Asp
165                 170                 175                 180

TTA GTA GAT TCT TAT GGA ACC GTT AGA TAT AAT GAA AAA GAA AAA ATA          692
Leu Val Asp Ser Tyr Gly Thr Val Arg Tyr Asn Glu Lys Glu Lys Ile
                185                 190                 195

TTT ATG GAT TGT TTT AAT AGA ATA TAT GAT ATG AAT GCT TCT ATG TTA          740
Phe Met Asp Cys Phe Asn Arg Ile Tyr Asp Met Asn Ala Ser Met Leu
                200                 205                 210

AAA ACT GAT GAA TAT AAT AAA AAC ACA TTG ACT ATT CCT TCA ATA GAT          788
Lys Thr Asp Glu Tyr Asn Lys Asn Thr Leu Thr Ile Pro Ser Ile Asp
                215                 220                 225

AAC ACG TAT ATA AAT GTA AAA ACT AAT GAA TGT AAT ATA AAT CAG GTT          836
Asn Thr Tyr Ile Asn Val Lys Thr Asn Glu Cys Asn Ile Asn Gln Val
            230                 235                 240

GAT AAT AAT CAT AAC AAT TAT ATT AAT GAT AAG GAT AAC ACT TTT AAT          884
Asp Asn Asn His Asn Asn Tyr Ile Asn Asp Lys Asp Asn Thr Phe Asn
245                 250                 255                 260

AAT TCT GAA AAA TCG GAT GAA TGG ATT TAT TTA CAA ACA AGA TGT CCA          932
Asn Ser Glu Lys Ser Asp Glu Trp Ile Tyr Leu Gln Thr Arg Cys Pro
                265                 270                 275

CAT CCA TAT ACT GCT GTA CAA ATT TGT TCT TAT ATT TTG AAA CTA AAA          980
His Pro Tyr Thr Ala Val Gln Ile Cys Ser Tyr Ile Leu Lys Leu Lys
                280                 285                 290

AAT AAA GGA GAT AGT GTT GGG GGT ATT GCT ACA TGC ATT ATA CAA AAT         1028
Asn Lys Gly Asp Ser Val Gly Gly Ile Ala Thr Cys Ile Ile Gln Asn
            295                 300                 305

CCT CCT ATA GGT ATT GGA GAA CCT ATT TTT GAC AAA TTG GAA GCT GAG         1076
Pro Pro Ile Gly Ile Gly Glu Pro Ile Phe Asp Lys Leu Glu Ala Glu
            310                 315                 320

CTA GCC AAA ATG ATT TTA TCT ATT CCA CCC GTG AAA GGA ATA GAA TTC         1124
Leu Ala Lys Met Ile Leu Ser Ile Pro Pro Val Lys Gly Ile Glu Phe
325                 330                 335                 340

GGG AGT GGA TTT AAT GGT ACA TAT ATG TTT GGC TCA ATG CAT AAT GAT         1172
Gly Ser Gly Phe Asn Gly Thr Tyr Met Phe Gly Ser Met His Asn Asp
                345                 350                 355

ATC TTC ATA CCT GTA GAA AAT ATG TCT ACA AAA AAA GAA AGT GAT TTA         1220
Ile Phe Ile Pro Val Glu Asn Met Ser Thr Lys Lys Glu Ser Asp Leu
                360                 365                 370

TTA TAT GAT GAT AAA GGT GAA TGT AAA AAT ATG TCT TAT CAT TCA ACG         1268
Leu Tyr Asp Asp Lys Gly Glu Cys Lys Asn Met Ser Tyr His Ser Thr
                375                 380                 385

ATT CAA AAT AAT GAG GAT CAA ATA TTA AAT TCA ACT AAA GGA TTT ATG         1316
Ile Gln Asn Asn Glu Asp Gln Ile Leu Asn Ser Thr Lys Gly Phe Met
                390                 395                 400

CCT CCT AAA AAT GAC AAG AAT TTT AAT AAT ATT GAT GAT TAC AAT GTT         1364
Pro Pro Lys Asn Asp Lys Asn Phe Asn Asn Ile Asp Asp Tyr Asn Val
405                 410                 415                 420
```

```
ACG TTT AAT AAT AAT GAA GAA AAA TTA TTA ATT ACA AAA ACA AAT AAT     1412
Thr Phe Asn Asn Asn Glu Glu Lys Leu Leu Ile Thr Lys Thr Asn Asn
                425                 430                 435

TGT GGT GGG ATT TTA GCT GGC ATT TCA ACA GGA AAC AAT ATT GTT TTT     1460
Cys Gly Gly Ile Leu Ala Gly Ile Ser Thr Gly Asn Asn Ile Val Phe
            440                 445                 450

AGA TCA GCA ATC AAA CCT GTA TCA TCA ATA CAA ATA GAA AAA GAA ACA     1508
Arg Ser Ala Ile Lys Pro Val Ser Ser Ile Gln Ile Glu Lys Glu Thr
                455                 460                 465

AGT GAT TTT TAT GGA AAT ATG TGT AAC TTG AAA GTT CAA GGG AGA CAT     1556
Ser Asp Phe Tyr Gly Asn Met Cys Asn Leu Lys Val Gln Gly Arg His
            470                 475                 480

GAT AGC TGT ATT TTA CCA AGA TTA CCA CCC ATT ATT GAA GCA TCT TCT     1604
Asp Ser Cys Ile Leu Pro Arg Leu Pro Pro Ile Ile Glu Ala Ser Ser
485                 490                 495                 500

TCA ATG GTT ATA GGA GAT TTA ATA TTA CGA CAA ATA TCA AAG TAT GGA     1652
Ser Met Val Ile Gly Asp Leu Ile Leu Arg Gln Ile Ser Lys Tyr Gly
                505                 510                 515

GAT AAA AAG TTG CCA ACA TTG TTT AGG AAT ATG TAACATAATG ATTTTGTAAT   1705
Asp Lys Lys Leu Pro Thr Leu Phe Arg Asn Met
            520                 525

CCTCAATTAA AATGAAAAAT TATAAAATAT ATATTTTATA TATATATATA AAATATATAT   1765

ATATATATAT AAAATATAAA TATATGTATA ATAATTCAAT TTGCGCAATC GATCAAAATA   1825

CATTTCGTCT AC                                                       1837
```

(2) INFORMATION FOR SEQ ID NO:4:

(i) SEQUENCE CHARACTERISTICS:
        (A) LENGTH: 527 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Thr Tyr Gly Thr Leu Leu Lys Val Thr Ser Tyr Gly Glu Ser
1               5                   10                  15

His Gly Lys Ala Ile Gly Cys Val Ile Asp Gly Phe Leu Ser Asn Ile
                20                  25                  30

Glu Ile Asn Phe Asp Leu Ile Gln Lys Gln Leu Asp Arg Arg Arg Pro
            35                  40                  45

Asn Gln Ser Lys Leu Thr Ser Asn Arg Asn Glu Lys Asp Lys Leu Val
        50                  55                  60

Ile Leu Ser Gly Phe Asp Glu Asn Lys Thr Leu Gly Thr Pro Ile Thr
65                  70                  75                  80

Phe Leu Ile Tyr Asn Glu Asp Ile Lys Lys Glu Asp Tyr Asn Ser Phe
                85                  90                  95

Ile Asn Ile Pro Arg Pro Gly His Gly Asp Tyr Thr Tyr Phe Met Lys
            100                 105                 110

Tyr His Val Lys Asn Lys Ser Gly Ser Ser Arg Phe Ser Gly Arg Glu
        115                 120                 125

Thr Ala Thr Arg Val Ala Ala Gly Ala Cys Ile Glu Gln Trp Leu Tyr
    130                 135                 140

Lys Ser Tyr Asn Cys Ser Ile Val Ser Tyr Val His Ser Val Gly Asn
145                 150                 155                 160

Ile Lys Ile Pro Glu Gln Val Ser Lys Glu Leu Glu Asn Lys Asn Pro
                165                 170                 175
```

```
Pro Ser Arg Asp Leu Val Asp Ser Tyr Gly Thr Val Arg Tyr Asn Glu
            180                 185                 190
Lys Glu Lys Ile Phe Met Asp Cys Phe Asn Arg Ile Tyr Asp Met Asn
            195                 200                 205
Ala Ser Met Leu Lys Thr Asp Glu Tyr Asn Lys Asn Thr Leu Thr Ile
            210                 215                 220
Pro Ser Ile Asp Asn Thr Tyr Ile Asn Val Lys Thr Asn Glu Cys Asn
225                 230                 235                 240
Ile Asn Gln Val Asp Asn Asn His Asn Asn Tyr Ile Asn Asp Lys Asp
            245                 250                 255
Asn Thr Phe Asn Asn Ser Glu Lys Ser Asp Glu Trp Ile Tyr Leu Gln
            260                 265                 270
Thr Arg Cys Pro His Pro Tyr Thr Ala Val Gln Ile Cys Ser Tyr Ile
            275                 280                 285
Leu Lys Leu Lys Asn Lys Gly Asp Ser Val Gly Gly Ile Ala Thr Cys
            290                 295                 300
Ile Ile Gln Asn Pro Pro Ile Gly Ile Gly Glu Pro Ile Phe Asp Lys
305                 310                 315                 320
Leu Glu Ala Glu Leu Ala Lys Met Ile Leu Ser Ile Pro Pro Val Lys
            325                 330                 335
Gly Ile Glu Phe Gly Ser Gly Phe Asn Gly Thr Tyr Met Phe Gly Ser
            340                 345                 350
Met His Asn Asp Ile Phe Ile Pro Val Glu Asn Met Ser Thr Lys Lys
            355                 360                 365
Glu Ser Asp Leu Leu Tyr Asp Asp Lys Gly Glu Cys Lys Asn Met Ser
            370                 375                 380
Tyr His Ser Thr Ile Gln Asn Asn Glu Asp Gln Ile Leu Asn Ser Thr
385                 390                 395                 400
Lys Gly Phe Met Pro Pro Lys Asn Asp Lys Asn Phe Asn Asn Ile Asp
            405                 410                 415
Asp Tyr Asn Val Thr Phe Asn Asn Glu Glu Lys Leu Leu Ile Thr
            420                 425                 430
Lys Thr Asn Asn Cys Gly Gly Ile Leu Ala Gly Ile Ser Thr Gly Asn
            435                 440                 445
Asn Ile Val Phe Arg Ser Ala Ile Lys Pro Val Ser Ser Ile Gln Ile
            450                 455                 460
Glu Lys Glu Thr Ser Asp Phe Tyr Gly Asn Met Cys Asn Leu Lys Val
465                 470                 475                 480
Gln Gly Arg His Asp Ser Cys Ile Leu Pro Arg Leu Pro Ile Ile
            485                 490                 495
Glu Ala Ser Ser Ser Met Val Ile Gly Asp Leu Ile Leu Arg Gln Ile
            500                 505                 510
Ser Lys Tyr Gly Asp Lys Lys Leu Pro Thr Leu Phe Arg Asn Met
            515                 520                 525
```

(2) INFORMATION FOR SEQ ID NO:5:

(i) SEQUENCE CHARACTERISTICS:
        (A) LENGTH: 72 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

```
Ile Pro Val Glu Asn Met Ser Thr Lys Lys Glu Ser Asp Leu Leu Tyr
1               5                   10                  15

Asp Asp Lys Gly Glu Cys Lys Asn Met Ser Tyr His Ser Thr Ile Gln
                20                  25                  30

Asn Asn Glu Asp Gln Ile Leu Asn Ser Thr Lys Gly Phe Met Pro Pro
            35                  40                  45

Lys Asn Asp Lys Asn Phe Asn Asn Ile Asp Asp Tyr Asn Val Thr Phe
        50                  55                  60

Asn Asn Asn Glu Glu Lys Leu Leu
65                  70
```

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

TGTCCAAGAT GTTCAGCCT                                                    19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

AGGCTGATCA TCTTGGACA                                                    19

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

TCGGGTCTGG TTGATTTT                                                     18

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

GAGAGAGCGT CGTGTTCAT                                                   19

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

ATGAACACGA CGCTCTCTC                                                19

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

CATGTCGAGA AGTTGTTC                                                 18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

GAACAACTTC TCGACATG                                                 18

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

ACTTGTGCAT ACGGGGTAC                                                19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

GTACCCCGTA TGCACAAGT                                                19

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

TGAATGCAAC TGAACTGC                                              18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

GCAGTTCAGT TGCATTCA                                              18

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:17:

AGCCGTTGGG TGTATAATC                                           19

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:18:

CTACGGCACC AGCTTCAC                                              18

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:19:

CGTCCTTCCT CAACACAGTG                                                    20

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:20:

GTGAAGCTGG TGCCGTAG                                                      18

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:21:

CGCCTCTGAT TTGGAAGTG                                                     19

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:22:

TCTGCCGCAT TCCACTAG                                                      18

(2) INFORMATION FOR SEQ ID NO:23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

GAAGCCAAGC AGTTCAGTT                                                     19

(2) INFORMATION FOR SEQ ID NO:24:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

```
AGCTATTGGG TGGATC                                                    16

(2) INFORMATION FOR SEQ ID NO:25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:25:

TCCATGTCCT GGTCTAGG                                                  18

(2) INFORMATION FOR SEQ ID NO:26:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:26:

ATAAAAACAC ATTGACTATT CCTTC                                          25

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:27:

GGGGATTTTT ATTTTCCAAT TCTTTG                                         26

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:28:

TTGAATCGTT GAATGATAAG AC                                             22

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"
```

-continued (xi) SEQUENCE DESCRIPTION: SEQ ID NO:29:

TTTTAGATCA GCAATCAAAC C                                                    21

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:30:

AACTTTTTAT CTCCATACTT TG                                                   22

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:31:

GAAGGAATAG TCAATGTGTT TTTAT                                                25

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:32:

GTATTTTACC AAGATTACCA CCC                                                  23

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:33:

CCCCCAACAC TATGTCG                                                         17

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:34:

CAGTGGGCAA AATAAAGA                                                                        18

(2) INFORMATION FOR SEQ ID NO:35:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:35:

CCAGTGGGCA AAATAA                                                                          16

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:36:

GGAAGAGAAA CAGCCAC                                                                         17

(2) INFORMATION FOR SEQ ID NO:37:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:37:

TGCTGCTGGG GCGTG                                                                           15

(2) INFORMATION FOR SEQ ID NO:38:

(i) SEQUENCE CHARACTERISTICS:
        (A) LENGTH: 362 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:38:

Met Gly Asn Thr Phe Gly Ser Leu Phe Arg Ile Thr Thr Phe Gly Glu
1               5                   10                  15

Ser His Gly Gly Gly Val Gly Val Ile Ile Asp Gly Cys Pro Pro Arg
            20                  25                  30

Leu Glu Ile Ser Pro Glu Ile Gln Val Asp Leu Asp Arg Arg Arg
        35                  40                  45

Pro Gly Gln Ser Lys Ile Thr Thr Pro Arg Lys Glu Ala Asp Gln Cys
    50                  55                  60

Glu Ile Leu Ser Gly Val Phe Glu Gly Lys Thr Leu Gly Thr Pro Ile

-continued

```
                65                  70                  75                  80

Ala Ile Leu Val Arg Asn Lys Asp Ala Arg Ser Gln Asp Tyr Asn Glu
                85                  90                  95

Met Ala Val Lys Tyr Arg Pro Ser His Ala Asp Ala Thr Tyr Glu Ala
                100                 105                 110

Lys Tyr Gly Ile Arg Asn Trp Gln Gly Gly Arg Ser Ser Ala Arg
                115                 120                 125

Glu Thr Ile Gly Arg Val Ala Ala Gly Ala Ile Ala Lys Lys Ile Leu
                130                 135                 140

Ala Gln Phe Asn Gly Val Glu Ile Val Ala Tyr Val Lys Ser Ile Gln
145                 150                 155                 160

Asp Ile Glu Ala Thr Val Asp Ser Asn Thr Val Thr Leu Glu Gln Val
                165                 170                 175

Glu Ser Asn Ile Val Arg Cys Pro Asp Glu Glu Cys Ala Glu Lys Met
                180                 185                 190

Ile Glu Arg Ile Asp Gln Val Leu Arg Gln Lys Asp Ser Ile Gly Gly
                195                 200                 205

Val Val Glu Cys Ala Ile Arg Asn Ala Pro Lys Gly Leu Gly Glu Pro
                210                 215                 220

Val Phe Asp Lys Leu Glu Ala Asp Leu Ala Lys Ala Met Met Ser Leu
225                 230                 235                 240

Pro Ala Thr Lys Gly Phe Glu Phe Gly Ser Gly Phe Ala Gly Thr Leu
                245                 250                 255

Leu Thr Gly Ser Gln His Asn Asp Glu Tyr Tyr Leu Asp Glu Ala Gly
                260                 265                 270

Glu Trp Arg Thr Arg Thr Asn Arg Ser Gly Gly Val Gln Gly Gly Ile
                275                 280                 285

Ser Asn Gly Glu Pro Ile Ile Met Arg Ile Ala Phe Lys Pro Thr Ala
                290                 295                 300

Thr Ile Gly Gln Glu Gln Lys Thr Val Ser Asn Ile Gly Glu Glu Thr
305                 310                 315                 320

Thr Leu Ala Ala Lys Gly Arg His Asp Pro Cys Val Leu Pro Arg Ala
                325                 330                 335

Val Pro Met Val Glu Ala Met Ala Ala Leu Val Leu Cys Asp His Leu
                340                 345                 350

Leu Arg Phe Gln Ala Gln Cys Lys Thr Leu
                355                 360

(2) INFORMATION FOR SEQ ID NO:39:

(i) SEQUENCE CHARACTERISTICS:
        (A) LENGTH: 431 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:39:

Met Ala Ser Ser Met Leu Thr Lys Gln Phe Leu Gly Ala Pro Phe Ser
1               5                   10                  15

Ser Phe Gly Ser Gly Gln Gln Pro Ser Lys Leu Cys Ser Ser Asn Leu
                20                  25                  30

Arg Phe Pro Thr His Arg Ser Gln Pro Lys Arg Leu Glu Ile Gln Ala
                35                  40                  45

Ala Gly Asn Thr Phe Gly Asn Tyr Phe Arg Val Thr Thr Phe Gly Glu
```

```
              50                  55                  60
Ser His Gly Gly Val Gly Cys Ile Ile Asp Gly Cys Pro Pro Arg
 65                  70                  75                  80

Leu Pro Leu Ser Glu Ser Asp Met Gln Val Glu Leu Asp Arg Arg
                 85                  90                  95

Pro Gly Gln Ser Arg Ile Thr Thr Pro Arg Lys Glu Thr Asp Thr Cys
                100                 105                 110

Lys Ile Ser Ser Gly Thr Ala Asp Gly Leu Thr Thr Gly Ser Pro Ile
                115                 120                 125

Lys Val Glu Val Pro Asn Thr Asp Gln Arg Gly Asn Asp Tyr Ser Glu
                130                 135                 140

Met Ser Leu Ala Tyr Arg Pro Ser His Ala Asp Ala Thr Tyr Asp Phe
145                 150                 155                 160

Lys Tyr Gly Val Arg Ser Val Gln Gly Gly Arg Ser Ser Ala Arg
                165                 170                 175

Glu Thr Ile Gly Arg Val Ala Ala Gly Ala Val Ala Lys Lys Ile Leu
                180                 185                 190

Lys Leu Tyr Ser Gly Thr Glu Ile Leu Ala Tyr Val Ser Gln Val His
                195                 200                 205

Asn Val Val Leu Pro Glu Asp Leu Val Asp Asn Gln Ile Val Thr Leu
210                 215                 220

Glu Gln Ile Glu Ser Asn Ile Val Arg Cys Pro Asn Pro Glu Tyr Ala
225                 230                 235                 240

Glu Lys Met Ile Gly Ala Ile Asp Tyr Val Arg Val Arg Gly Asp Ser
                245                 250                 255

Val Gly Gly Val Val Thr Cys Ile Val Arg Asn Val Pro Arg Gly Leu
                260                 265                 270

Gly Thr Pro Val Phe Asp Lys Leu Glu Ala Glu Leu Ala Lys Ala Cys
                275                 280                 285

Met Ser Leu Pro Ala Thr Lys Gly Phe Glu Phe Gly Ser Gly Phe Ala
                290                 295                 300

Gly Thr Phe Met Thr Gly Ser Glu His Asn Asp Glu Phe Phe Met Asp
305                 310                 315                 320

Glu His Asp Gln Ile Arg Thr Lys Thr Asn Arg Ser Gly Gly Ile Gln
                325                 330                 335

Gly Gly Ile Ser Asn Gly Glu Ile Ile Asn Met Arg Val Ala Phe Lys
                340                 345                 350

Pro Thr Ser Thr Ile Ala Arg Lys Gln His Thr Val Ser Arg Asp Lys
                355                 360                 365

His Glu Thr Glu Leu Ile Ala Arg Gly Arg His Asp Pro Cys Val Val
                370                 375                 380

Pro Arg Ala Val Pro Met Val Glu Ala Met Val Ala Leu Val Leu Val
385                 390                 395                 400

Asp Gln Leu Met Thr Gln Tyr Ala Gln Cys Met Leu Phe Pro Val Asn
                405                 410                 415

Leu Thr Leu Gln Glu Pro Leu Gln Pro Ser Thr Thr Lys Ser Ala
                420                 425                 430

(2) INFORMATION FOR SEQ ID NO:40:

(i) SEQUENCE CHARACTERISTICS:
        (A) LENGTH: 432 amino acids
        (B) TYPE: amino acid
        (C) STRANDEDNESS:
        (D) TOPOLOGY: linear
```

(ii) MOLECULE TYPE: protein (xi) SEQUENCE DESCRIPTION: SEQ ID NO:40:

| Met | Ser | Thr | Phe | Gly | His | Tyr | Phe | Arg | Val | Thr | Thr | Tyr | Gly | Glu | Ser |
|---|---|---|---|---|---|---|---|---|---|---|---|---|---|---|---|
| 1 | | | | 5 | | | | | 10 | | | | | 15 | |

| His | Cys | Lys | Ser | Val | Gly | Cys | Ile | Val | Asp | Gly | Val | Pro | Pro | Gly | Met |
|---|---|---|---|---|---|---|---|---|---|---|---|---|---|---|---|
| | | | 20 | | | | | 25 | | | | | 30 | | |

| Glu | Leu | Thr | Glu | Asp | Asp | Ile | Gln | Pro | Gln | Met | Thr | Arg | Arg | Arg | Pro |
|---|---|---|---|---|---|---|---|---|---|---|---|---|---|---|---|
| | | | 35 | | | | | 40 | | | | | 45 | | |

| Gly | Gln | Ser | Ala | Ile | Thr | Thr | Pro | Arg | Asp | Glu | Lys | Asp | Arg | Val | Ile |
|---|---|---|---|---|---|---|---|---|---|---|---|---|---|---|---|
| | 50 | | | | | 55 | | | | | 60 | | | | |

| Ile | Gln | Ser | Gly | Thr | Glu | Phe | Gly | Val | Thr | Leu | Gly | Thr | Pro | Ile | Gly |
|---|---|---|---|---|---|---|---|---|---|---|---|---|---|---|---|
| 65 | | | | | 70 | | | | | 75 | | | | | 80 |

| Met | Leu | Val | Met | Asn | Glu | Asp | Gln | Pro | Pro | Lys | Asp | Tyr | Gly | Asn | Lys |
|---|---|---|---|---|---|---|---|---|---|---|---|---|---|---|---|
| | | | | 85 | | | | | 90 | | | | | 95 | |

| Thr | Met | Asp | Ile | Tyr | Pro | Arg | Pro | Ser | His | Ala | Asp | Trp | Thr | Tyr | Leu |
|---|---|---|---|---|---|---|---|---|---|---|---|---|---|---|---|
| | | | 100 | | | | | 105 | | | | | 110 | | |

| Glu | Lys | Tyr | Gly | Val | Lys | Ala | Ser | Ser | Gly | Gly | Gly | Arg | Ser | Ser | Ala |
|---|---|---|---|---|---|---|---|---|---|---|---|---|---|---|---|
| | | 115 | | | | | 120 | | | | | 125 | | | |

| Arg | Glu | Thr | Ile | Gly | Arg | Val | Ala | Ala | Gly | Ala | Ile | Ala | Glu | Lys | Tyr |
|---|---|---|---|---|---|---|---|---|---|---|---|---|---|---|---|
| | 130 | | | | | 135 | | | | | 140 | | | | |

| Leu | Lys | Pro | Arg | Tyr | Gly | Val | Glu | Ile | Val | Ala | Phe | Val | Ser | Ser | Val |
|---|---|---|---|---|---|---|---|---|---|---|---|---|---|---|---|
| 145 | | | | | 150 | | | | | 155 | | | | | 160 |

| Gly | Ser | Glu | His | Leu | Phe | Pro | Pro | Thr | Ala | Glu | His | Pro | Ser | Pro | Ser |
|---|---|---|---|---|---|---|---|---|---|---|---|---|---|---|---|
| | | | | 165 | | | | | 170 | | | | | 175 | |

| Thr | Asn | Pro | Glu | Phe | Leu | Lys | Leu | Val | Asn | Ser | Ile | Thr | Arg | Glu | Thr |
|---|---|---|---|---|---|---|---|---|---|---|---|---|---|---|---|
| | | | 180 | | | | | 185 | | | | | 190 | | |

| Val | Asp | Ser | Phe | Leu | Pro | Val | Arg | Cys | Pro | Asp | Ala | Glu | Ala | Asn | Lys |
|---|---|---|---|---|---|---|---|---|---|---|---|---|---|---|---|
| | | 195 | | | | | 200 | | | | | 205 | | | |

| Arg | Met | Glu | Asp | Leu | Ile | Thr | Lys | Phe | Arg | Asp | Asn | His | Asp | Ser | Ile |
|---|---|---|---|---|---|---|---|---|---|---|---|---|---|---|---|
| | 210 | | | | | 215 | | | | | 220 | | | | |

| Gly | Gly | Thr | Val | Thr | Cys | Val | Ile | Arg | Asn | Val | Pro | Ser | Gly | Leu | Gly |
|---|---|---|---|---|---|---|---|---|---|---|---|---|---|---|---|
| 225 | | | | | 230 | | | | | 235 | | | | | 240 |

| Glu | Pro | Ala | Phe | Asp | Lys | Leu | Glu | Ala | Met | Leu | Ala | His | Ala | Met | Leu |
|---|---|---|---|---|---|---|---|---|---|---|---|---|---|---|---|
| | | | | 245 | | | | | 250 | | | | | 255 | |

| Ser | Ile | Pro | Ala | Thr | Lys | Gly | Phe | Glu | Val | Gly | Ser | Gly | Phe | Gly | Gly |
|---|---|---|---|---|---|---|---|---|---|---|---|---|---|---|---|
| | | | 260 | | | | | 265 | | | | | 270 | | |

| Cys | Glu | Val | Pro | Gly | Ser | Ile | His | Asn | Asp | Pro | Phe | Val | Ser | Ala | Glu |
|---|---|---|---|---|---|---|---|---|---|---|---|---|---|---|---|
| | | 275 | | | | | 280 | | | | | 285 | | | |

| Asn | Thr | Glu | Ile | Pro | Pro | Ser | Val | Ala | Ala | Ser | Gly | Ala | Ala | Arg | Asn |
|---|---|---|---|---|---|---|---|---|---|---|---|---|---|---|---|
| | 290 | | | | | 295 | | | | | 300 | | | | |

| Gly | Ile | Pro | Arg | Pro | Lys | Leu | Thr | Thr | Lys | Thr | Asn | Phe | Ser | Gly | Gly |
|---|---|---|---|---|---|---|---|---|---|---|---|---|---|---|---|
| 305 | | | | | 310 | | | | | 315 | | | | | 320 |

| Ile | Gln | Gly | Gly | Ile | Ser | Asn | Gly | Ala | Pro | Ile | Tyr | Phe | Arg | Val | Gly |
|---|---|---|---|---|---|---|---|---|---|---|---|---|---|---|---|
| | | | | 325 | | | | | 330 | | | | | 335 | |

| Phe | Lys | Pro | Ala | Ala | Thr | Ile | Gly | Gln | Glu | Gln | Thr | Thr | Ala | Thr | Tyr |
|---|---|---|---|---|---|---|---|---|---|---|---|---|---|---|---|
| | | | 340 | | | | | 345 | | | | | 350 | | |

| Asp | Gly | Thr | Ser | Glu | Gly | Val | Leu | Ala | Ala | Lys | Gly | Arg | His | Asp | Pro |
|---|---|---|---|---|---|---|---|---|---|---|---|---|---|---|---|
| | | 355 | | | | | 360 | | | | | 365 | | | |

| Ser | Val | Val | Pro | Arg | Ala | Val | Pro | Ile | Val | Glu | Ala | Met | Ala | Ala | Leu |
|---|---|---|---|---|---|---|---|---|---|---|---|---|---|---|---|
| | 370 | | | | | 375 | | | | | 380 | | | | |

| Val | Ile | Met | Asp | Ala | Val | Leu | Ala | His | Glu | Ala | Arg | Val | Thr | Ala | Lys |
|---|---|---|---|---|---|---|---|---|---|---|---|---|---|---|---|
| 385 | | | | | 390 | | | | | 395 | | | | | 400 |

```
Ser Leu Leu Pro Pro Leu Lys Gln Thr Ile Asn Ser Gly Lys Asp Thr
                405                 410                 415

Val Gly Asn Gly Val Ser Glu Asn Val Gln Glu Ser Asp Leu Ala Gln
            420                 425                 430
```

(2) INFORMATION FOR SEQ ID NO:41:

(i) SEQUENCE CHARACTERISTICS:
        (A) LENGTH: 357 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:41:

```
Met Ala Gly Asn Thr Ile Gly Gln Leu Phe Arg Val Thr Thr Phe Gly
1               5                   10                  15

Glu Ser His Gly Ile Ala Leu Gly Cys Ile Val Asp Gly Val Pro Pro
            20                  25                  30

Asn Leu Glu Leu Ser Glu Lys Asp Ile Gln Pro Asp Leu Asp Arg Arg
        35                  40                  45

Lys Pro Gly Thr Ser Arg Tyr Thr Thr Pro Arg Arg Glu Asp Asp Glu
    50                  55                  60

Val Gln Ile Leu Ser Gly Val Phe Glu Gly Lys Thr Thr Gly Thr Ser
65                  70                  75                  80

Ile Gly Met Ile Ile Lys Asn Gly Asp Gln Arg Ser Gln Asp Tyr Gly
                85                  90                  95

Asp Ile Lys Asp Arg Phe Arg Pro Gly His Ala Asp Phe Thr Tyr Gln
                100                 105                 110

Gln Lys Tyr Gly Ile Arg Asp Tyr Arg Gly Gly Gly Arg Ser Ser Ala
            115                 120                 125

Arg Glu Thr Ala Met Arg Val Ala Ala Gly Ala Ile Ala Lys Lys Tyr
        130                 135                 140

Leu Arg Glu His Phe Gly Ile Glu Val Arg Gly Phe Leu Ser Gln Ile
145                 150                 155                 160

Gly Asn Ile Lys Ile Ala Pro Gln Lys Val Gly Gln Ile Asp Trp Glu
                165                 170                 175

Lys Val Asn Ser Asn Pro Phe Phe Cys Pro Asp Glu Ser Ala Val Glu
                180                 185                 190

Lys Phe Asp Glu Leu Ile Arg Glu Leu Lys Lys Glu Gly Asp Ser Ile
            195                 200                 205

Gly Ala Lys Leu Thr Val Ile Ala Glu Asn Val Pro Val Gly Leu Gly
        210                 215                 220

Glu Pro Val Phe Asp Arg Leu Asp Ala Asp Leu Ala His Ala Leu Met
225                 230                 235                 240

Gly Ile Asn Ala Val Lys Gly Val Glu Ile Gly Asp Gly Phe Ala Val
                245                 250                 255

Val Glu Gln Arg Gly Ser Glu His Arg Asp Glu Met Thr Pro Asn Gly
            260                 265                 270

Phe Glu Ser Asn His Ala Gly Gly Ile Leu Gly Gly Ile Ser Ser Gly
        275                 280                 285

Gln Pro Ile Ile Ala Thr Ile Ala Leu Lys Pro Thr Ser Ser Ile Thr
    290                 295                 300

Ile Pro Gly Arg Ser Ile Asn Leu Asn Gly Glu Ala Val Glu Val Val
305                 310                 315                 320
```

Thr Lys Gly Arg His Asp Pro Cys Val Gly Ile Arg Ala Val Pro Ile
                325                 330                 335

Ala Glu Ala Met Val Ala Ile Val Leu Leu Asp His Leu Leu Arg Phe
                340                 345                 350

Lys Ala Gln Cys Lys
        355

(2) INFORMATION FOR SEQ ID NO:42:

(i) SEQUENCE CHARACTERISTICS:
        (A) LENGTH: 376 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:42:

Met Ser Thr Phe Gly Lys Leu Phe Arg Val Thr Thr Tyr Gly Glu Ser
1                   5                   10                  15

His Cys Lys Ser Val Gly Cys Ile Val Asp Gly Val Pro Pro Gly Met
                20                  25                  30

Ser Leu Thr Glu Ala Asp Ile Gln Pro Gln Leu Thr Arg Arg Arg Pro
            35                  40                  45

Gly Gln Ser Lys Leu Ser Thr Pro Arg Asp Glu Lys Asp Arg Val Glu
        50                  55                  60

Ile Gln Ser Gly Thr Glu Phe Gly Lys Thr Leu Gly Thr Pro Ile Ala
65                  70                  75                  80

Met Met Ile Lys Asn Glu Asp Gln Arg Pro His Asp Tyr Ser Asp Met
                85                  90                  95

Asp Lys Phe Pro Arg Pro Ser His Ala Asp Phe Thr Tyr Ser Glu Lys
                100                 105                 110

Tyr Gly Ile Lys Ala Ser Ser Gly Gly Arg Ala Ser Ala Arg Glu
            115                 120                 125

Thr Ile Gly Arg Val Ala Ser Gly Ala Ile Ala Glu Lys Phe Leu Ala
130                 135                 140

Gln Asn Ser Asn Val Glu Ile Val Ala Phe Val Thr Gln Ile Gly Glu
145                 150                 155                 160

Ile Lys Met Asn Arg Asp Ser Phe Asp Pro Glu Phe Gln His Leu Leu
                165                 170                 175

Asn Thr Ile Thr Arg Glu Lys Val Asp Ser Met Gly Pro Ile Arg Cys
            180                 185                 190

Pro Asp Ala Ser Val Ala Gly Leu Met Val Lys Glu Ile Glu Lys Tyr
        195                 200                 205

Arg Gly Asn Lys Asp Ser Ile Gly Gly Val Val Thr Cys Val Val Arg
210                 215                 220

Asn Leu Pro Thr Gly Leu Gly Glu Pro Cys Phe Asp Lys Leu Glu Ala
225                 230                 235                 240

Met Leu Ala His Ala Met Leu Ser Ile Pro Ala Ser Lys Gly Phe Glu
                245                 250                 255

Ile Gly Ser Gly Phe Gln Gly Val Ser Val Pro Gly Ser Lys His Asn
            260                 265                 270

Asp Pro Phe Tyr Phe Glu Lys Glu Thr Asn Arg Leu Arg Thr Lys Thr
        275                 280                 285

Asn Asn Ser Gly Gly Val Gln Gly Gly Ile Ser Asn Gly Glu Asn Ile
290                 295                 300

```
Tyr Phe Ser Val Pro Phe Lys Ser Val Ala Thr Ile Ser Gln Glu Gln
305                 310                 315                 320

Lys Thr Ala Thr Tyr Asp Gly Glu Glu Gly Ile Leu Ala Ala Lys Gly
                325                 330                 335

Arg His Asp Pro Ala Val Thr Pro Arg Ala Ile Pro Ile Val Glu Ala
                340                 345                 350

Met Thr Ala Leu Val Leu Ala Asp Ala Leu Leu Ile Gln Lys Ala Arg
                355                 360                 365

Asp Phe Ser Arg Ser Val Val His
        370                 375
```

(2) INFORMATION FOR SEQ ID NO:43:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Ser Cys Ser Phe Ser Glu Ser Ala Ala Ser Thr Ile Lys His Glu Arg
1               5                   10                  15

Asp Gly Cys Ser Ala Ala Thr Leu Ser Arg Glu Arg Ala Ser Asp Gly
            20                  25                  30

Arg Thr Thr Ser Arg His Glu Glu Val Glu Arg Gly
            35                  40              45
```

(2) INFORMATION FOR SEQ ID NO:44:

(i) SEQUENCE CHARACTERISTICS:
        (A) LENGTH: 82 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

```
Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
            35                  40                  45

Ser Ala Arg Ala Ala Pro Arg His Gln Gln Gln Ala Arg Arg Gly Gly
        50              55                  60

Arg Phe Pro Ser Leu Val Val Cys Ala Ser Ala Gly Met Asn Val Val
65                  70                  75                  80

Phe Val
```